United States Patent
Dupont-Passelaigue et al.

(10) Patent No.: US 7,713,971 B2
(45) Date of Patent: May 11, 2010

(54) 1,2,4-TRIAZINE DERIVATIVES, PREPARATION AND USE THEREOF IN HUMAN THERAPY

(75) Inventors: Elisabeth Dupont-Passelaigue, Castres (FR); Isabelle Leroy, Saix (FR); Jean-François Patoiseau, Castres (FR); Didier Junquero, Castres (FR); Yves Rival, Lagarrigue (FR); André Delhon, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 11/885,630

(22) PCT Filed: Mar. 2, 2006

(86) PCT No.: PCT/FR2006/000469

§ 371 (c)(1),
(2), (4) Date: Nov. 19, 2007

(87) PCT Pub. No.: WO2006/092507

PCT Pub. Date: Sep. 8, 2006

(65) Prior Publication Data

US 2008/0167313 A1 Jul. 10, 2008

(30) Foreign Application Priority Data

Mar. 3, 2005 (FR) ................... 05 02152

(51) Int. Cl.
*C07D 253/065* (2006.01)
*A61K 31/53* (2006.01)
*A61P 3/04* (2006.01)
*A61P 3/06* (2006.01)
*A61P 3/10* (2006.01)
*A61P 9/10* (2006.01)

(52) U.S. Cl. ..................... 514/242; 544/182

(58) Field of Classification Search ............... 544/182; 514/242

See application file for complete search history.

(56) References Cited

U.S. PATENT DOCUMENTS 5,591,743 A 1/1997 Patolseau et al.

FOREIGN PATENT DOCUMENTS

| WO | WO-95/01965 A | 1/1995 |
| WO | WO-02/38553 A2 | 5/2002 |
| WO | WO-02/096894 A | 12/2002 |
| WO | WO-2005/080354 A | 9/2005 |

OTHER PUBLICATIONS

Jones, A. B., Medicinal Research Reviews, vol. 21, No. 6., 540-552, 2001.*

* cited by examiner

*Primary Examiner*—Venkataraman Balasubramanian
(74) *Attorney, Agent, or Firm*—Birch, Stewart, Kolasch & Birch, LLP

(57) ABSTRACT

The invention relates to 3,5-dioxo-(2H,4H)-1,2,4-triazine compounds of formula I

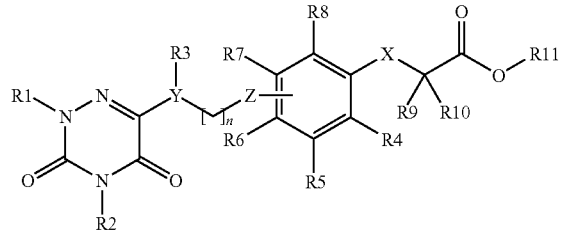

in which the variables are defined herein, as well as additive salts with pharmaceutically acceptable bases and the various enantiomers of compounds having asymmetrical carbons, as well as their mixtures in all proportions, including racemic mixtures in particular.

20 Claims, No Drawings

1,2,4-TRIAZINE DERIVATIVES, PREPARATION AND USE THEREOF IN HUMAN THERAPY

The present invention has as an aim new derivatives of 3,5-dioxo-(2H,4H)-1,2,4-triazine functionalized at 2, 4 and 6 which activate PPAR alpha and/or gamma receptors, their preparation and their application in human therapeutics.

Metabolic syndrome is the result of a peripheral resistance to increased insulin and is characterized by hyperinsulinemia, intolerance to glucose, change in lipid metabolism and arterial hypertension (Grundy, S. M.: Hypertriglyceridemia, insulin resistance, and the metabolic syndrome. *Am. J. Cardiol.* 1999, 83, 25F-29F). Obesity is often associated with these metabolic disorders, and the conjunction of these multiple risk factors favors the development of the atheromatosis at the origin of arterial thrombosis, today the number one cause of mortality in industrialized areas. Peroxisome proliferator-activated receptors (PPAR) belong to the superfamily of transcription factor nuclear receptors. After activation, they form heterodimers with 9-cis retinoic acid receptor (RXR); this complex (PPAR-RXR) is linked specifically with DNA sequences located in the regulatory regions of genes implicated in the metabolism of lipids and carbohydrates (Pineda Torra, I., Gervois, P. and Staels, B.: Peroxisome proliferator-activated receptor alpha in metabolic disease, inflammation, atherosclerosis and aging. *Curr. Opin. Lipidol.* 1999, 10, 151-159. Vamecq, J. and Latruffe, N.: Medical significance of peroxisome proliferator-activated receptors. *Lancet* 1999, 354, 141-148). PPAR activation, on the one hand, restores certain altered metabolic pathways that predispose to atherosclerosis, and on the other reduces the inflammatory events which favor atheroma plaque development and rupture.

The compounds of the present invention are characterized by their original structure, their affinity with respect to alpha and/or gamma PPAR receptors and their pharmacological profile.

The compounds of the invention correspond to the general formula I.

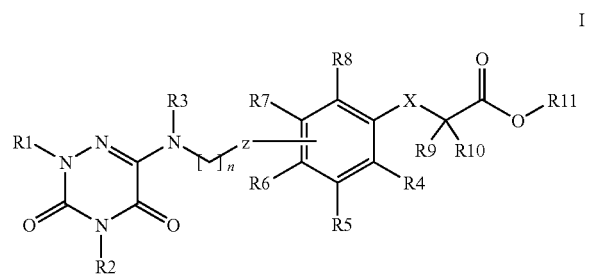

I in which $R_1$ and $R_2$ can be identical or different and represent an alkyl or alkenyl radical, linear or branched, at $C_1$-$C_7$, an alkyl radical at $C_1$-$C_6$ substituted by groups such as trifluoromethyl, cycloalkyl at $C_5$-$C_6$, nitrile, alkoxycarbonylvinyl at $C_1$-$C_4$, hydroxycarbonylvinyl, alkoxycarbonyl at $C_1$-$C_4$, carboxylate, benzyloxy or phenyl (for which the core phenyl is possibly substituted by one or more groups such as alkyl at $C_1$-$C_4$, alkoxy at $C_1$-$C_4$, nitro, halogen or trifluoromethyl), $YR_3$ represents oxygen or $NR_3$ in which $R_3$ represents hydrogen, an alkyl or alkenyl radical, linear or branched at $C_1$-$C_7$, an alkyl radical at $C_1$-$C_6$ substituted by groups such as trifluoromethyl or phenyl (for which the core phenyl is possibly substituted by one or more groups such as alkyl at $C_1$-$C_4$, alkoxy at $C_1$-$C_4$, nitro, halogen or trifluoromethyl), Z represents an oxygen atom or a carbon atom which can be bound in ortho, meta or para position on the phenyl group of formula I, n can range from 0 to 5 when Z=C or from 2 to 4 when Z=O, X represents oxygen or sulfur, $R_4$, $R_5$, $R_6$, $R_7$ and $R_8$ represent hydrogen or fluorine, $R_9$, $R_{10}$ and $R_{11}$ represent hydrogen or an alkyl group, linear or branched, at $C_1$-$C_5$, as well as additive salts with pharmaceutically acceptable bases and the various enantiomers of compounds having asymmetrical carbons, as well as their mixtures in all proportions, including racemic mixtures in particular.

The invention relates, in particular, to the compounds of formula I in which:

$R_1$ and $R_2$ represent, independently one from the other, an alkyl or alkenyl radical, linear or branched, at $C_1$-$C_7$, an alkyl radical at $C_1$-$C_6$ substituted by groups such as trifluoromethyl, cycloalkyl at $C_6$, nitrile, or phenyl (for which the core phenyl is possibly substituted by one or more groups such as alkyl at $C_1$-$C_4$, alkoxy at $C_1$-$C_4$, nitro, halogen or trifluoromethyl), $YR_3$ represents oxygen or $NR_3$ in which $R_3$ represents hydrogen, an alkyl or alkenyl radical, linear or branched, at $C_1$-$C_7$, an alkyl radical at $C_1$-$C_6$ substituted by groups such as trifluoromethyl or phenyl, Z represents an oxygen atom or a carbon atom which can be bound in ortho, meta or para position on the phenyl group of formula I n can range from 0 to 5 when Z=C or from 2 to 4 when Z=O, X represents oxygen or sulfur, $R_4$, $R_5$, $R_6$, $R_7$ and $R_8$ represent hydrogen or fluorine, $R_9$, $R_{10}$ and $R_{11}$ represent hydrogen or an alkyl group, linear or branched, at $C_1$-$C_5$.

The invention relates, more particularly, to the compounds of formula I in which:

$R_1$ and $R_2$ represent independently one from the other, an alkyl or alkenyl radical, linear or branched, at $C_1$-$C_7$, an alkyl radical at $C_1$-$C_6$ substituted by groups such as trifluoromethyl or nitrile, $YR_3$ represents oxygen or $NR_3$ in which $R_3$ represents hydrogen or a linear or branched alkyl radical at $C_1$-$C_7$, Z represents a carbon atom which can be bound in ortho, meta or para position on the phenyl group of formula I, n can range from 0 to 5, X represents oxygen or sulfur, $R_4$, $R_5$, $R_6$, $R_7$ and $R_8$ represent hydrogen or fluorine, $R_9$, $R_{10}$ and $R_{11}$ represents hydrogen or a linear or branched alkyl group at $C_1$-$C_5$, in particular $R_9$ and $R_{10}$ represent a methyl group and $R_{11}$ hydrogen or an ethyl group.

The invention relates still more particularly to the derivatives of 3,5-dioxo-(2H,4H)-1,2,4-triazine of formula I in which:

$R_1$ and $R_2$ represent independently one from the other, an alkyl or alkenyl radical, linear or branched, at $C_1$-$C_7$, possibly substituted at the end of the chain by a trifluoromethyl group, $YR_3$ represents oxygen or $NR_3$ in which $R_3$ represents hydrogen or a linear or branched alkyl radical at $C_1$-$C_7$, Z represents a carbon atom which can be bound in meta or para position on the phenyl group of formula I, n can range from 1 to 5, X represents oxygen or sulfur, $R_4$ to $R_8$ represent hydrogen, $R_9$ and $R_{10}$ represent a methyl radical $R_{11}$ represents hydrogen or an ethyl radical.

The invention encompasses salts of the compounds of general formula I with pharmaceutically acceptable bases, as well as the various enantiomers of compounds possessing asymmetrical carbons, as well as their mixtures in all proportions including racemic mixtures in particular.

Synthesis

The compounds of the present invention can be synthesized by using the synthetic pathways described below or by using synthesis methods known to those skilled in the art.

Method 1

The synthesis of compounds of general formula I is characterized (diagram 1) wherein a derivative of general formula II is condensed

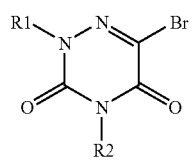
II in which $R_1$ and $R_2$ represent the groups as previously described in formula I with a derivative of general formula III

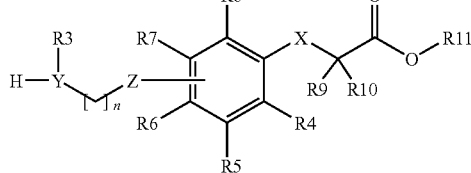
III where $YR_3$, n, Z, X, $R_4$, $R_5$, $R_6$, $R_7$, $R_8$, $R_9$, $R_{10}$ and $R_{11}$ are such as described previously in formula I. This reaction can be carried out in the presence of a base such as triethylamine in n-butanol (when Y=N) or potassium carbonate in dimethylformamide (when $YR_3$=O);

Diagram 1

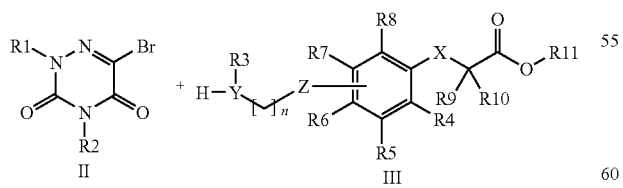

if Y = N, Et$_3$N, nBuOH
if YR3 = O, K$_2$CO$_3$, DMF

-continued

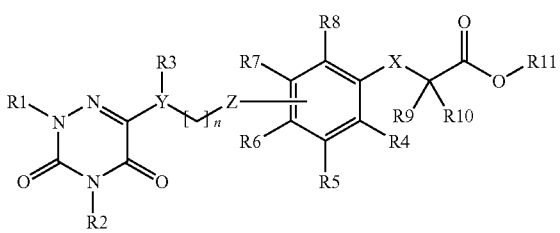

Method 2

This synthesis method for compounds of general formula I for which Z=O (diagram 2) is characterized wherein:

1) a derivative of general formula II is condensed

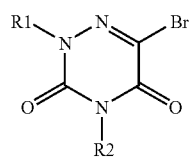
II in which $R_1$ and $R_2$ represent the groups as previously described in formula I with a derivative of general formula IV

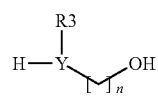
IV in which $R_3Y$ can be equal to NH or O and n is such as described previously in formula I. This reaction can be carried out in the absence of solvent without adding base (in the case where $R_3Y$=NH) or in the presence of a base such as K$_2$CO$_3$ (in the case where $R_3Y$=O).

2) the derivative obtained V is condensed

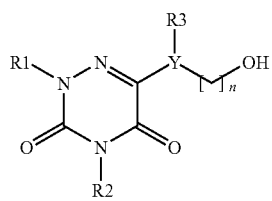
V with a compound of general formula VI

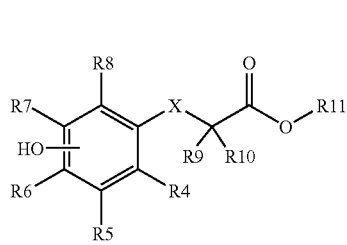

VI where X, $R_4$, $R_5$, $R_6$, $R_7$, $R_8$, $R_9$, $R_{10}$ and $R_{11}$ are as described previously in formula I. This reaction can be carried out under conditions such as those of the Mitsunobu reaction in the presence of triphenylphosphine and diethylazodicarboxylate in THF.

Diagram 2

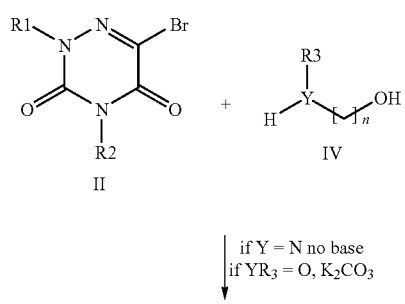

II

IV if Y = N no base
if $YR_3$ = O, $K_2CO_3$

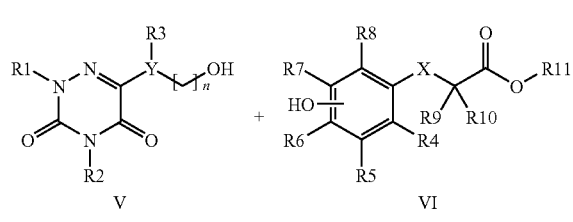

V

VI

DEAD, $PPh_3$, THF

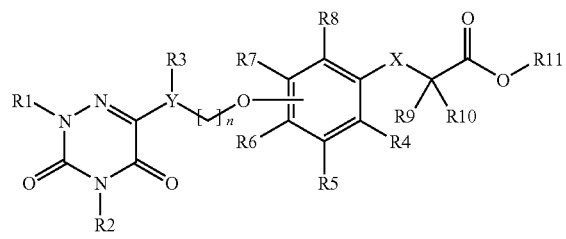

Method 3

This synthesis method for compounds of general formula I for which Z=O (diagram 3) is characterized wherein:

1) the alcohol function of a derivative of general formula VII is protected

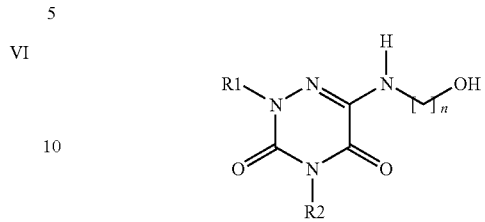

VII in which $R_1$, $R_2$ and n are as described previously in formula I by a protection group such as tert-butyldimethylsilane. This reaction can be carried out under conditions such as THF by using chlorotertbutyldimethylsilane and imidazole.

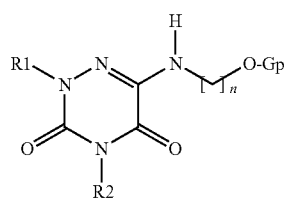

VIII 2) the nitrogen of compound VIII previously obtained is alkylated by a halogenated derivative $R_3Hal$ in which the Hal group represents a halogen such as Cl, Br or I and $R_3$ is as described previously in formula I, under operating conditions such as NaH or tBuOK in DMF.

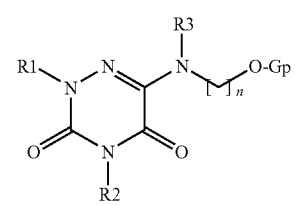

IX 3) the compound IX thus obtained is deprotected under operating conditions such as tetrabutylammonium fluoride in THF.

4) the derivative obtained X is condensed

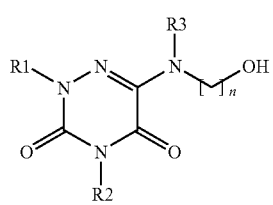

X with a compound of general formula VI

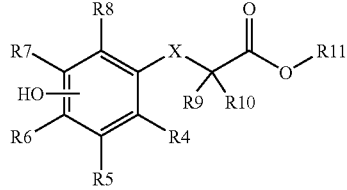

where X, $R_4$, $R_5$, $R_6$, $R_7$, $R_8$, $R_9$, $R_{10}$ and $R_{11}$ are as described previously in formula I. This reaction can be carried out under conditions such as those of the is Mitsunobu reaction in the presence of triphenylphosphine and diethylazodicarboxylate in THF.

Diagram 3

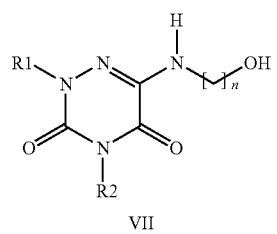
VII if Gp = tBuMe$_2$Si
tBuMe$_2$SiCl, imidazole, THF

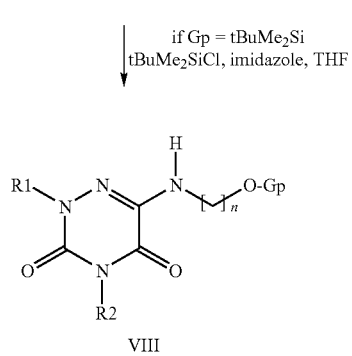
VIII

NaH, DMF, R$_3$Hal

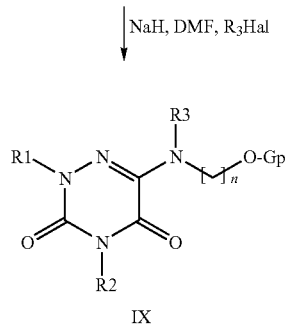
IX if Gp = tBuMe$_2$Si
nBu$_4$N$^+$F$^-$, THF

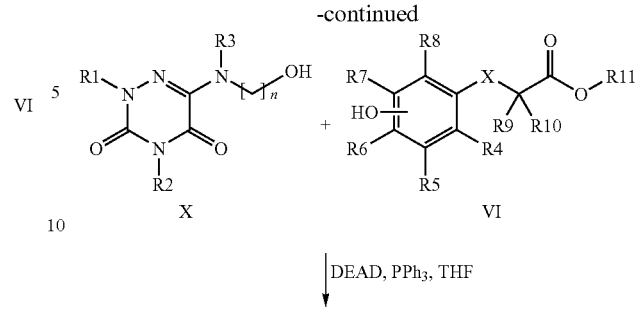

DEAD, PPh$_3$, THF

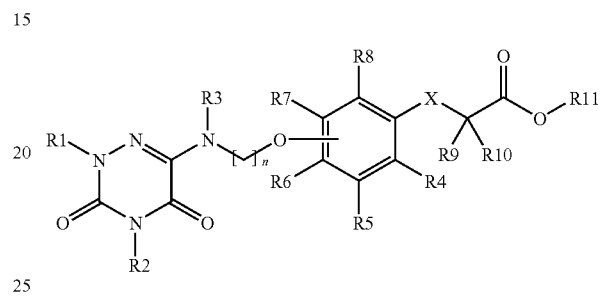

Method 4

This method is implemented when Y=N and Z=C and it is characterized (diagram 4) wherein:

1) a derivative of general formula II is condensed

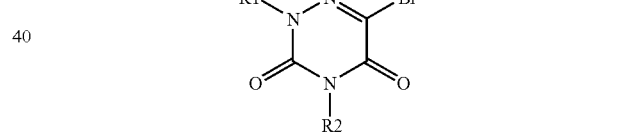

in which $R_1$ and $R_2$ represent the groups as previously described in formula I with a derivative of general formula XI

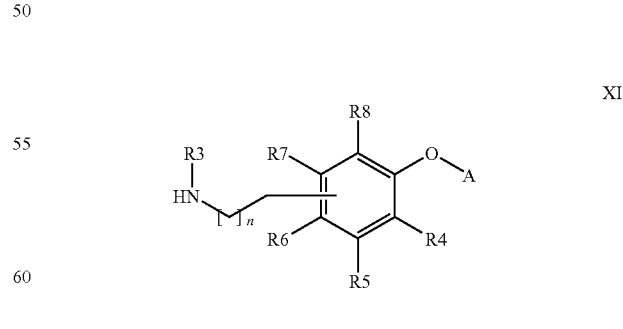

in which n, $R_3$ $R_4$, $R_5$, $R_6$, $R_7$ and $R_8$ are as described previously in formula I and A can be hydrogen or a methyl group. This reaction can be carried out in the presence of a base such as triethylamine in n-butanol.

2) after demethylation (if A=Me, under conditions such as BBr₃ in dichloromethane), the phenol function of derivative XII is alkylated

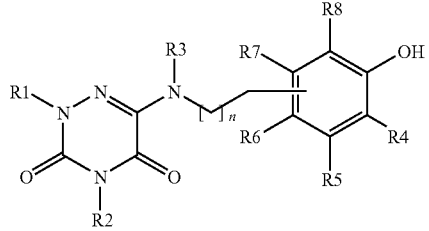

XII by a halogenated derivative of general formula XIII (used as a solvent in the presence of a base such as potassium carbonate)

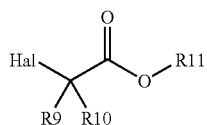

XIII in which the Hal group represents a halogen such as Cl, Br or I, and R₉, R₁₀ and R₁₁ are as previously described in general formula I.

Diagram 4

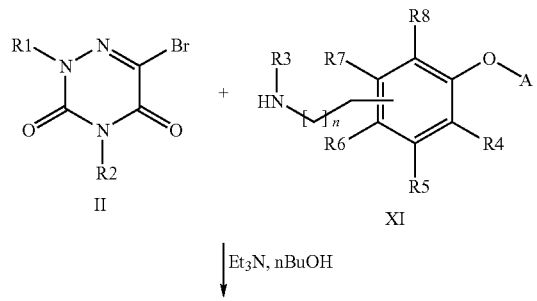

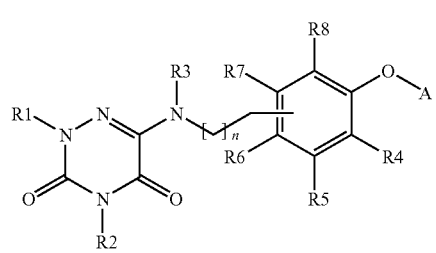

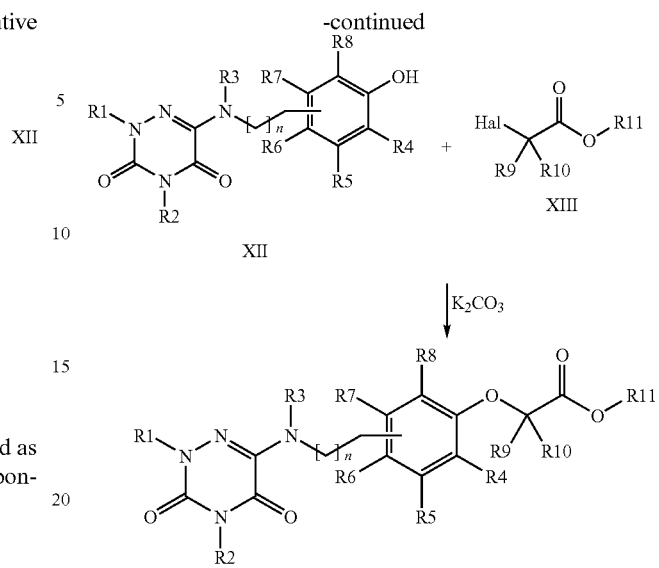

Method 5

This method is implemented when Y=N and Z=C and it is characterized (diagram 5) wherein:

1) a derivative of general formula XIV is alkylated

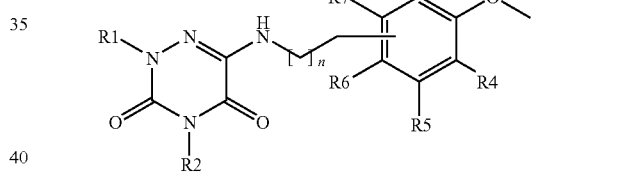

XIV in which R₁, R₂, R₄, R₅, R₆, R₇, R₈ et n are as described previously in formula I with a derivative of formula R₃Hal in which the Hal group represents a halogen such as Cl, Br or I and R₃ is as described previously in formula I, under operating conditions such as NaH or tBuOK in DMF.

2) after demethylation under conditions such as BBr₃ in dichloromethane, the phenol function of the derivative XII thus obtained is alkylated

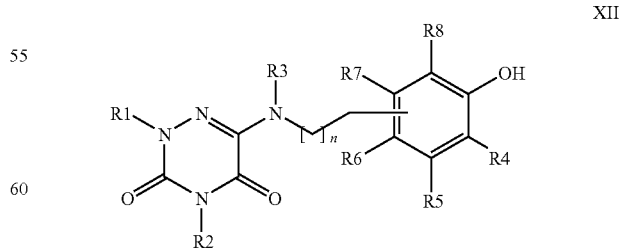

XII by a halogenated derivative of general formula XIII (used as a solvent in the presence of a base such as potassium carbonate)

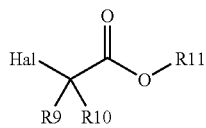

in which the Hal group represents a halogen such as Cl, Br or I, and $R_9$, $R_{10}$ and $R_{11}$ are as previously described in general formula I.

Diagram 5

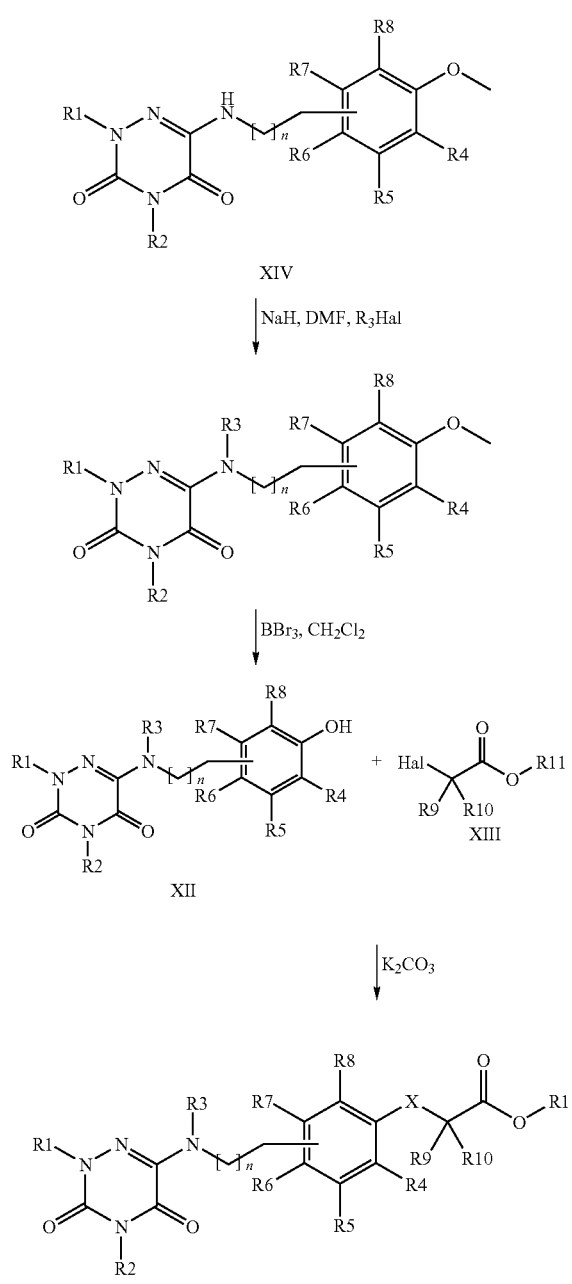

Method 6

This method is characterized (diagram 6) wherein:

1) a derivative of general formula XIV is placed

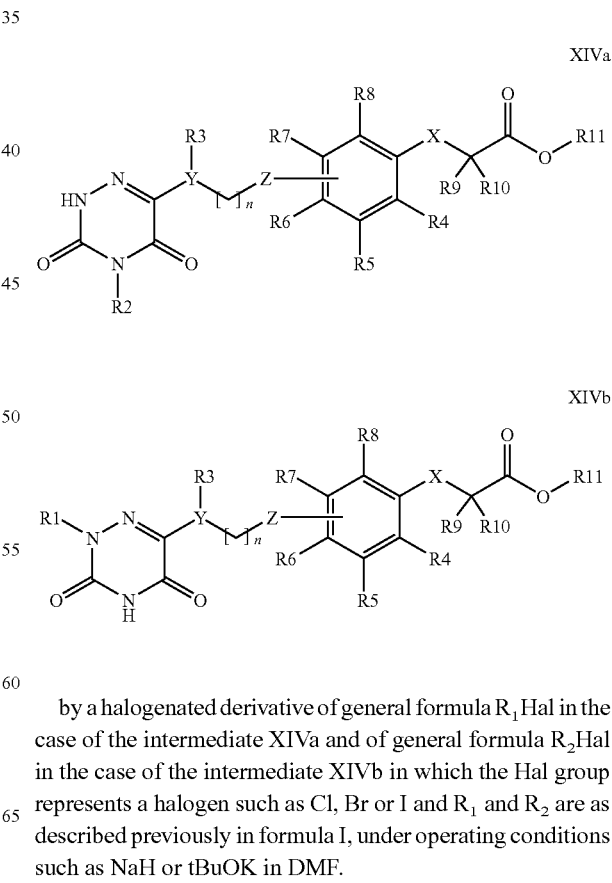

in which $R_1$=$(CH_2)_2CN$ and $R_2$, $R_3$, n, Z, X, $R_4$, $R_5$, $R_6$, $R_7$, $R_8$, $R_9$, $R_{10}$ and $R_{11}$ are as described previously in formula I or $R_2$=$(CH_2)_2CN$ and $R_1$, $R_3$, n, Z, X, $R_4$, $R_5$, $R_6$, $R_7$, $R_8$, $R_9$, $R_{10}$ and $R_{11}$ are as described previously in formula I under operating conditions such as in the presence of a base NaH in DMF.

2) the nitrogen of the triazine of derivative XIVa or XIVb thus obtained is then alkylated by a halogenated derivative of general formula $R_1$Hal in the case of the intermediate XIVa and of general formula $R_2$Hal in the case of the intermediate XIVb in which the Hal group represents a halogen such as Cl, Br or I and $R_1$ and $R_2$ are as described previously in formula I, under operating conditions such as NaH or tBuOK in DMF.

Diagram 6

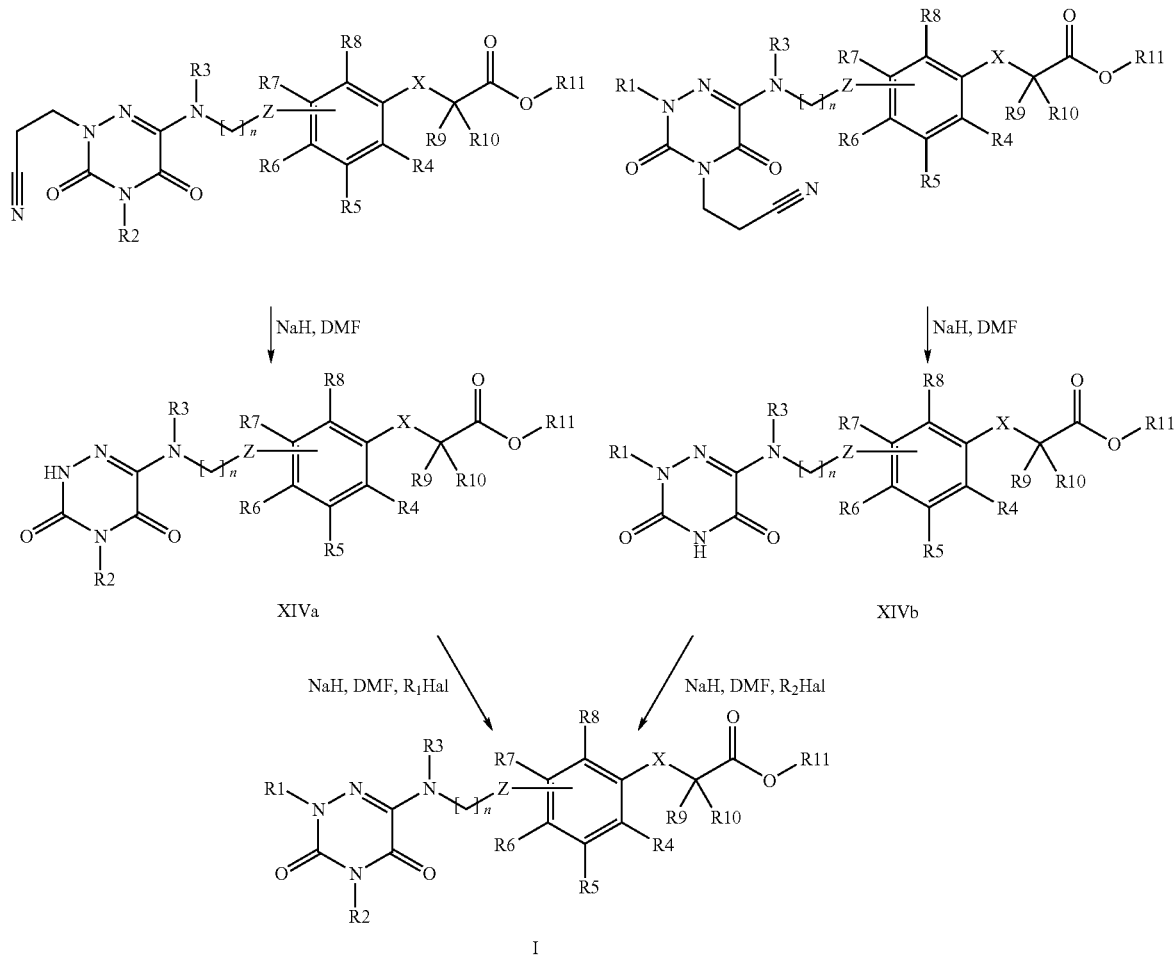

If desired, the intermediate and final compounds can be purified according to one or more purification methods chosen among extraction, filtration, silica gel chromatography, normal or reverse phase preparative HPLC and crystallization.

The raw materials used in the methods described previously are commercially available or easily accessible to those skilled in the art according to methods described in the literature.

The following examples illustrate the invention without limiting its scope.

Elementary analyses and IR and NMR spectra confirm the compounds' structures.

Intermediates

Intermediate 1:

a) 6-Bromo-2H-[1,2,4]triazine-3,5-dione (1a)

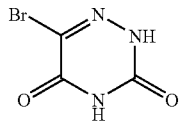

2H-[1,2,4]triazin-3,5-dione (50 g, 442 mmol) is placed in the presence of 60 ml of bromine in 800 ml of water at 60° C. for 10 h. The reaction medium is then slowly added to an ammonia solution until pH=5. It is then extracted in ethyl acetate and the organic phases are dried on MgSO$_4$. After filtration and dry concentration, 1a is isolated in the form of a white solid (79.2 g, yield=93%). TLC silica gel 60 F 254 Merck, CH$_2$Cl$_2$:MeOH 90:10, Rf=0.32.

b) 6-Bromo-2,4-dimethyl-2H-[1,2,4]triazine-3,5-dione (1b)

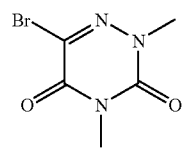

11.8 g (295 mmol) of NaH (60% in paraffin) is placed in suspension at 0° C. in 250 ml of DMF under nitrogen. 25.80 g (135 mmol) of intermediate 1a diluted in 150 ml of DMF is added drop by drop. This solution is then placed at ambient temperature and 18.4 ml (296 mmol) of methyl iodide is added dropwise. After a night of stirring and after dry concentration of the reaction medium, the residue obtained is taken up in water and extracted with ethyl acetate. The organic phases are washed with brine, dried on magnesium sulfate then dry concentrated. The residue obtained, taken up in ether, crystallizes and a first crystal fraction is isolated. The filtrate is dry concentrated the purified by plash chromatograph on silica (heptane:AcOEt 50:50). 24 g of intermediate 1b are thus isolated (81% yield) TLC silica gel 60 F 254 Merck, $CH_2Cl_2$:AcOEt 80:20, Rf=0.59.

c) Intermediates (1c)-(1g)

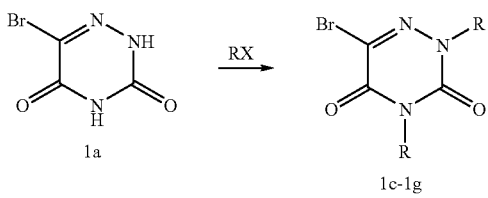

The synthesis of intermediates 1c-1g is carried out starting from 1a according to the procedure described for the synthesis of 1b by using various alkylation agents RX.

Intermediate 2:

a) 6-Bromo-4-methyl-2H-[1,2,4]triazine-3,5-dione (2a)

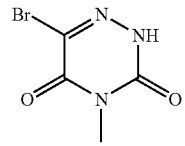

20.3 g (105.7 mmol) of triazine 1a are placed in 150 ml of acetic anhydride at reflux for 4.5 h. After dry concentration of the reaction medium, a precipitate is isolated then recrystallized in ether: 24.3 g of crystals are isolated (yield=98%). 4.5 g (114.2 mmol) of NaH (60% in paraffin) are placed in 50 ml of DMF under nitrogen. A solution of 24.3 g (103.8 mmol) of crystals isolated previously in 150 ml of DMF is added dropwise. The reaction medium is stirred for 45 nm at ambient temperature and then 7 ml (114.2 mmol) of methyl iodide are added; stirring is then continued for 21 h at ambient temperature. After dry concentration, the residue obtained is taken up in $H_2O$ and extracted with ethyl acetate. After drying on $MgSO_4$, the organic phases are evaporated and the clear oil obtained is purified by flash chromatography on silica

TABLE 1 intermediates 1c-1g

| RX | Yield | TLC | State | Intermediates 1c-1g |
|---|---|---|---|---|
| ~~~Br (butyl bromide) | 80% | PE:AcOEt 80:20 Rf = 0.42 | oil | 1c: 6-Bromo-2,4-dibutyl-2H-[1,2,4]triazine-3,5-dione |
| F,F,F-butyl iodide | 95% | PE:AcOEt 80:20 Rf = 0.75 | solid | 1d: 6-Bromo-2,4-bis-(4,4,4-trifluoro-butyl)-2H-[1,2,4]-triazine-3,5-dione |
| heptyl bromide | 95% | PE:AcOEt 90:10 Rf = 0.81 | oil | 1e: 6-Bromo-2,4-diheptyl-2H-[1,2,4]triazine-3,5-dione |
| 3-cyclohexylpropyl bromide | 92% | PE:AcOEt 90:10 Rf = 0.82 | oil | 1f: 6-Bromo-2,4-bis-(3-cyclohexyl-propyl)-2H-[1,2,4]triazine-3,5-dione |
| benzyloxymethyl chloride | 98% | PE:AcOEt 70:30 Rf = 0.62 | oil | 1g: 2,4-Bis-benzyloxymethyl-6-bromo-2H-[1,2,4]triazine-3,5-dione |

TLC: silica gel 60 F 254 Merck, PE = petroleum ether (CH₂Cl₂:AcOEt 90:10). 22.9 g of crystals (yield=89%) are isolated and are placed in 300 ml of ethanol in the presence of 0.6 g of p-toluene sulfonic acid. This mixture is heated at reflux for 4.5 h and then dry concentrated. The residue is taken up in H₂O and extracted with ethyl acetate. After drying and evaporation of the organic phases, 17 g of intermediate 2a is isolated in the form of a solid (yield=89%). TLC silica gel 60 F 254 Merck, CH₂Cl₂:AcOEt 90:10, Rf=0.29.

b) Intermediates (2b)-(2f)

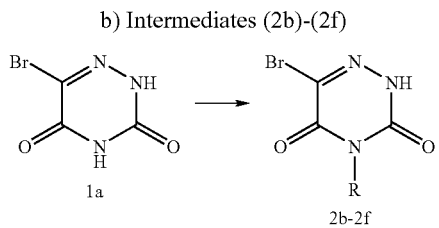

1a 2b-2f

The synthesis of intermediates 2b-2f is carried out starting from 1a according to the procedure described for the synthesis of 2a by using various alkylation agents RX.

the organic phases are dry concentrated. 2.8 g of solid 3a are isolated and then washed with ether (yield=93%). TLC silica gel 60 F 254 Merck, petroleum ether:AcOEt 70:30, Rf=0.18.

b) Intermediates 3b and 3c

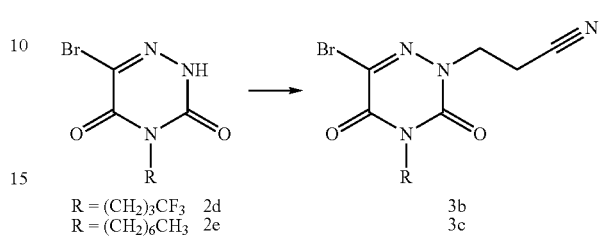

R = (CH₂)₃CF₃  2d
R = (CH₂)₆CH₃  2e 3b
3c

The synthesis of intermediates 3b and 3c is carried out starting from intermediates 2d and 2e, respectively, following the procedure described for the synthesis of 3a.

TABLE 2 intermediates 2b-2f

| RX | Total yield | TLC | State | Intermediates 2b-2f |
|---|---|---|---|---|
| ~~~Br | 73% | PE:AcOEt 80:20 Rf = 0.28 | solid | 2b: 6-Bromo-4-butyl-2H-[1,2,4]triazine-3,5-dione |
| ~~Br (methylallyl) | 60% | PE:AcOEt 80:20 Rf = 0.26 | solid | 2c: 6-Bromo-4-(3-methyl-but-2-enyl)-2H-[1,2,4]triazine-3,5-dione |
| F₃C(CH₂)₃I | 76% | CH₂Cl₂:AcOEt 90:10 Rf = 0.45 | solid | 2d: 6-Bromo-4-(4,4,4'-trifluoro-butyl)-2H-[1,2,4]triazine-3,5-dione |
| ~~~~~~Br | 84% | PE:AcOEt 70:30 Rf = 0.73 | solid | 2e: 6-Bromo-4-heptyl-2H-[1,2,4]triazine-3,5-dione |
| PhCH₂Br | 82% | PE:AcOEt 70:30 Rf = 0.25 | solid | 2f: 4-Benzyl-6-bromo-2H-[1,2,4]triazine-3,5-dione |

TLC: silica gel 60 F 254 Merck, PE = petroleum ether

Intermediate 3:

a) 3-(6-Bromo-4-methyl-3,5-dioxo-4,5-dihydro-3H-[1,2,4]triazin-2-yl)-propionitrile (3a)

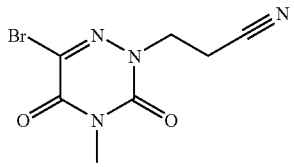

2.4 g (11.6 mmol) of triazine 2a and 7 ml (106 mmol) of acrylonitrile are placed in 24 ml of a solution of pyridine and water (1:1) at reflux for 3 h. After concentration the reaction medium is extracted by AcOEt, and after drying on MgSO₄

TABLE 3 intermediates 3b and 3c

| Starting molecule | Yield | TLC | State | Intermediates 3b-3c |
|---|---|---|---|---|
| 2d | 91% | PE:AcOEt 70:30 Rf = 0.34 | solid | 3b: 3-[6-Bromo-3,5-dioxo-4-(4,4,4-trifluoro-butyl)-4,5-dihydro-3H-[1,2,4]triazin-2-yl]-propionitrile |
| 2e | 95% | CH₂Cl₂:AcOEt 70:30 Rf = 0.51 | solid | 3c: 3-(6-Bromo-4-heptyl-3,5-dioxo-4,5-dihydro-3H-[1,2,4]triazin-2-yl)-propionitrile |

TLC: silica gel 60 F 254 Merck, PE = petroleum ether

Intermediate 4:

d) 6-Bromo-4-methyl-2-(4,4,4-trifluoro-butyl)-2H-[1,2,4]triazine-3,5-dione (4a)

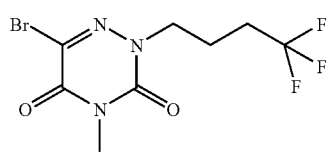

0.85 g (21.3 mmol) of NaH (60% in paraffin) is placed in 10 ml of DMF under nitrogen. A solution of 4 g (19.4 mmol) of intermediate 2a in 40 ml of DMF is added dropwise. The reaction medium is stirred for 1 h at ambient temperature and then 5 g (21.3 mmol) of 1,1,1-trifluoro-4-iodo-butane are added; stirring is then continued for 3 h at ambient temperature. After dry concentration, the residue obtained is taken up in $H_2O$ and extracted with ethyl acetate. After drying on $MgSO_4$, the organic phases are evaporated and the oil obtained is purified by flash chromatography on silica (petroleum ether:AcOEt 80:20). 5.3 g of crystals corresponding to compound 4a are isolated (yield=87%). TLC silica gel 60 F 254 Merck, petroleum ether:AcOEt 70:30, Rf=0.58.

d) 6-Bromo-2-heptyl-4-methyl-2H-[1,2,4]triazine-3,5-dione (4b)

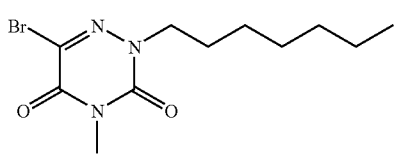

The synthesis of intermediate 4b is carried out starting from 2a according to the procedure described for the synthesis of 4a by using 1-bromoheptane for the alkylation step (yield=91%). TLC silica gel 60 F 254 Merck, petroleum ether:AcOEt 70:30, Rf=0.76.

Intermediate 5:

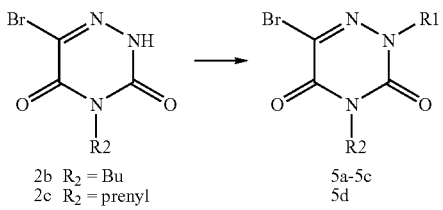

| | | | 2b R$_2$ = Bu | 5a-5c |
| | | | 2c R$_2$ = prenyl | 5d |

The synthesis of intermediates 5a-5d is carried out starting from intermediates 2b and 2c according to the procedure described for the synthesis of 4a by using various halogenated derivatives $R_1X$.

TABLE 4 intermediates 5a-5d

| $R_1X$ | Yield | TLC | State | Intermediates 5a-5c |
|---|---|---|---|---|
| —I | 64% | CH$_2$Cl$_2$:AcOEt 95:5 Rf = 0.75 | solid | 5a: 6-Bromo-4-butyl-2-methyl-2H-[1,2,4]triazine-3,5-dione |
| F$_3$C-CH$_2$CH$_2$CH$_2$-I | 95% | PE:AcOEt 80:20 Rf = 0.61 | oil | 5b: 6-Bromo-4-butyl-2-(4,4,4-trifluoro-butyl)-2H-[1,2,4]triazine-3,5-dione |
| CH$_3$(CH$_2$)$_6$-Br | 72% | PE:AcOEt 80:20 Rf = 0.75 | oil | 5c: 6-Bromo-4-butyl-2-heptyl-2H-[1,2,4]triazine-3,5-dione |
| F$_3$C-CH$_2$CH$_2$CH$_2$-I | 90% | PE:AcOEt 80:20 Rf = 0.58 | oil | 5d: 6-Bromo-4-(3-methyl-but-2-enyl)-2-(4,4,4-trifluoro-butyl)-2H-[1,2,4]triazine-3,5-dione |

TLC: silica gel 60 F 254 Merck, PE = petroleum ether

Intermediate 6:

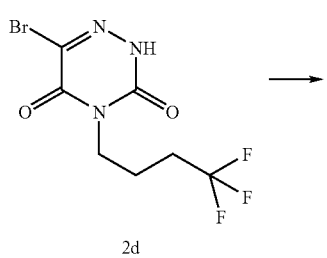

2d

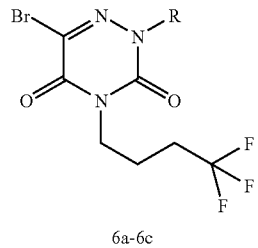

6a-6c

The synthesis of intermediates 6a-6c is carried out starting from intermediate 2d according to the procedure described for the synthesis of 4a by using various halogenated derivatives RX.

TABLE 5 intermediates 6a-6c

| RX | Yield | TLC | State | Intermediates 6a-6b |
|---|---|---|---|---|
| —I | 91% | PE:AcOEt 70:30 Rf = 0.61 | solid | 6a: 6-Bromo-2-methyl-4-(4,4,4-trifluoro-butyl)-2H-[1,2,4]triazine-3,5-dione |
| ~~~~~~Br | 88% | PE:AcOEt 60:40 Rf = 0.53 | oil | 6b: 6-Bromo-2-heptyl-4-(4,4,4-trifluoro-butyl)-2H-[1,2,4]triazine-3,5-dione |
| Cyclohexyl-CH2CH2CH2-Br | 80% | PE:AcOEt 60:40 Rf = 0.43 | oil | 6c: 6-Bromo-2-(3-cyclohexyl-propyl)-4-(4,4,4-trifluoro-butyl)-2H-[1,2,4]triazine-3,5-dione |

TLC: silica gel 60 F 254 Merck, PE = petroleum ether

Intermediate 7:

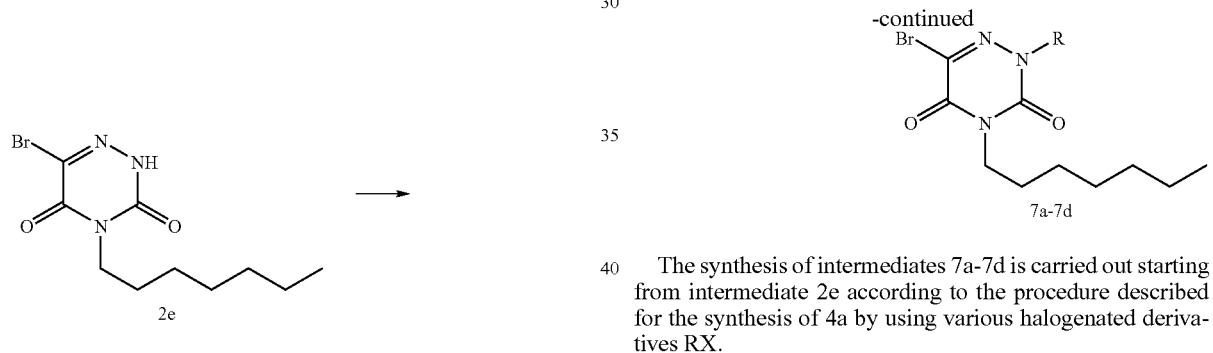

2e → 7a-7d

The synthesis of intermediates 7a-7d is carried out starting from intermediate 2e according to the procedure described for the synthesis of 4a by using various halogenated derivatives RX.

TABLE 6 intermediates 7a-7d

| RX | Yield | TLC | State | Intermediates 7a-7d |
|---|---|---|---|---|
| —I | 92% | CH$_2$Cl$_2$:MeOH 95-5 Rf = 0.65 | oil | 7a: 6-Bromo-4-heptyl-2-methyl-2H-[1,2,4]triazine-3,5-dione |
| CF$_3$-CH$_2$CH$_2$CH$_2$-I | 98% | PE:AcOEt 70:30 Rf = 0.81 | oil | 7b: 6-Bromo-4-heptyl-2-(4,4,4-trifluoro-butyl)-2H-[1,2,4]triazine-3,5-dione |
| PhCH$_2$-Br | 80% | PE:AcOEt 80:20 Rf = 0.60 | oil | 7c: 2-Benzyl-6-bromo-4-heptyl-2H-[1,2,4]triazine-3,5-dione |

TABLE 6-continued intermediates 7a-7d

| RX | Yield | TLC | State | Intermediates 7a-7d |
|---|---|---|---|---|
|  | 78% | PE:AcOEt 80:20 Rf = 0.59 | oil | 7d: 6-Bromo-2-cyclohexylmethyl-4-heptyl-2H-[1,2,4]triazine-3,5-dione |

TLC: silica gel 60 F 254 Merck, PE = petroleum ether

Intermediate 8:

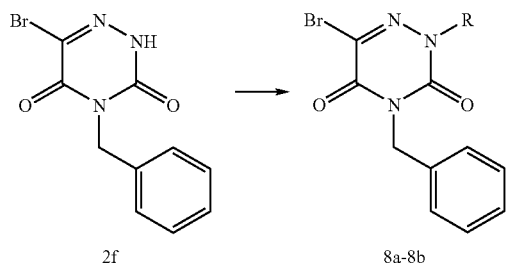

The synthesis of intermediates 8a-8b is carried out starting from intermediate 2f according to the procedure described for the synthesis of 4a by using various halogenated derivatives RX.

3 g (7.3 mmol) of triazine 1d are placed in 1.3 ml of ethanolamine at 130° C. for 5 h. After cooling, 50 ml of water are added to the reaction medium which is then extracted with AcOEt. After drying on $MgSO_4$, the organic phases are dry concentrated and the residue obtained is purified by flash chromatography on silica (petroleum ether:AcOEt 70:30). 1.9 g of oil corresponding to intermediate 9a is thus isolated (66% yield). TLC silica gel 60 F 254. Merck, petroleum ether:AcOEt 70:30, Rf=0.28.

TABLE 7 intermediates 8a-8b

| RX | Yield | TLC | State | Intermediates 8a-8b |
|---|---|---|---|---|
| F F F ~~~I | 93% | PE:AcOEt 80:20 Rf = 0.46 | oil | 8a: 4-Benzyl-6-bromo-2-(4,4,4-trifluoro-butyl)-2H-[1,2,4]triazine-3,5-dione |
| ~~~~~~Br | 98% | PE:AcOEt 80:20 Rf = 0.66 | oil | 8b: 4-Benzyl-6-bromo-2-heptyl-2H-[1,2,4]triazine-3,5-dione |

TLC: silica gel 60 F 254 Merck, PE = petroleum ether

Intermediate 9:

a) 6-(2-Hydroxy-ethylamino)-2,4-bis-(4,4,4-trifluoro-butyl)-2H-[1,2,4]triazine-3,5-dione (9a)

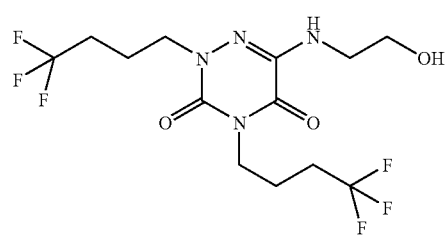

b) Intermediates 9b-9l

The synthesis of intermediates 9b-9l is carried out from the starting compounds listed in table 8 following the procedure described for the synthesis of 9a.

TABLE 8 intermediates 9b-9l

| Starting molecule | Amino alcohol | Yield | TLC | State | Intermediates 9b-9k |
|---|---|---|---|---|---|
| 4b | Ethanol-amine | 77% | $CH_2Cl_2$:AcOEt 60:40<br>Rf = 0.28 | solid | 9b: 2-Heptyl-6-(2-hydroxy-ethylamino)-4-methyl-2H-[1,2,4]triazine-3,5-dione |
| 1e | Ethanol-amine | 67% | PE:AcOEt 70:30<br>Rf = 0.56 | oil | 9c: 2,4-Diheptyl-6-(2-hydroxy ethylamino)-2H-[1,2,4]triazine-3,5-dione |
| 1f | Ethanol-amine | 56% | PE:AcOEt 80:20<br>Rf = 0.18 | oil | 9d: 2,4-Bis-(3-cyclohexyl-propyl)-6-(2-hydroxy-ethyl-amino)-2H-[1,2,4]triazine-3,5-dione |
| 1b | Amino-propanol | 18% | AcOEt<br>Rf = 0.42 | oil | 9e: 6-(3-Hydroxy-propyl-amino)-2,4-dimethyl-2H-[1,2,4]triazine-3,5-dione |
| 4a | Amino-propanol | 44% | PE:AcOEt 70:30<br>Rf = 0.13 | solid | 9f: 6-(3-Hydroxy-propylamino)-4-methyl-2-(4,4,4-trifluoro-butyl)-2H-[1,2,4]triazine-3,5-dione |
| 4b | Amino-propanol | 67% | $CH_2Cl_2$:AcOEt 60:40<br>Rf = 0.32 | solid | 9g: 2-Heptyl-6-(3-hydroxy-propylamino)-4-methyl-2H-[1,2,4]triazine-3,5-dione |
| 6a | Amino-propanol | 45% | PE:AcOEt 80:20<br>Rf = 0.05 | solid | 9h: 6-(3-Hydroxy-propyl-amino)-2-methyl-4-(4,4,4-trifluoro-butyl)-2H-[1,2,4]triazine-3,5-dione |
| 7a | Amino-propanol | 34% | $CH_2Cl_2$:MeOH 90:10<br>Rf = 0.47 | solid | 9i: 4-Heptyl-6-(3-hydroxy-propylamino)-2-methyl-2H-[1,2,4]triazine-3,5-dione |
| 7b | Amino-propanol | 64% | PE:AcOEt 70:30<br>Rf = 0.30 | solid | 9j: 4-Heptyl-6-(3-hydroxy-propylamino)-2-(4,4,4-trifluoro-butyl)-2H-[1,2,4]triazine-3,5-dione |
| 1b | Amino-butanol | 50% | AcOEt<br>Rf = 0.35 | solid | 9k: 6-(4-Hydroxy-butyl-amino)-2,4-dimethyl-2H-[1,2,4]triazine-3,5-dione |
| 7a | Amino-butanol | 21% | $CH_2Cl_2$:MeOH 90:10<br>Rf = 0.45 | solid | 9l: 4-Heptyl-6-(4-hydroxy-butylamino)-2-methyl-2H-[1,2,4]triazine-3,5-dione |

TLC: silica gel 60 F 254 Merck,

PE = petroleum ether c) 2-heptyl-6-[(3-hydroxy-propyl)-(4,4,4-trifluoro-butyl)-amino]-4-methyl-2H-[1,2,4]triazine-3,5-dione (9m)

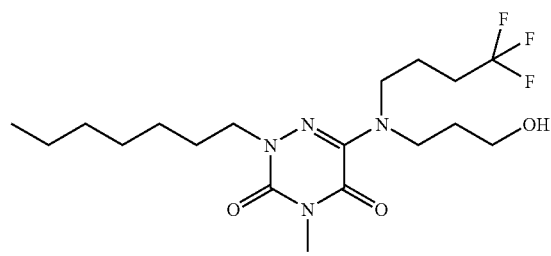

7.3 g (24.2 mmol) of triazine 9g are placed in the presence of tert-butyl-chloro-dimethyl-silane (4 g, 26.5 mmol) in 50 ml of dichloromethane at ambient temperature overnight. The reaction medium is then washed with water followed with brine. After drying on MgSO$_4$, the organic phase is dry concentrated and the residue obtained is purified by flash chromatography on silica (CH$_2$Cl$_2$:AcOEt 95:5). 10 g of oil are isolated (quantitative yield). 4.1 g (10 mmol) of this compound are placed in 40 ml of DMF at 0° C. under nitrogen and then 0.4 g (10 mmol) of NaH (60% in paraffin) is added by fractions; this mixture is then stirred for 10 mn. 2.4 g (10 mmol) of 1,1,1-trifluoro-4-iodo-butane are added and the solution is stirred at ambient temperature for 3 h. 0.5 equivalent of NaH as well as 1,1,1-trifluoro-4-iodo-butane are again added and stirring is continued for 2 h. After dry concentration, the residue is taken up in H$_2$O then extracted with AcOEt. After drying on MgSO$_4$, the organic phases are dry concentrated and the oil obtained is purified by flash chromatography on silica (petroleum ether:AcOEt 90:10). 2 g of compound (yield=40%) are isolated and then diluted in 30 ml of THF; 7.4 ml of a tetrabutylammonium fluoride solution (1 M in THF) is then added dropwise. This mixture is stirred for 2 h at ambient temperature and then 50 ml of water are added and the medium is extracted with AcOEt. After drying on MgSO$_4$, the organic phases are dry concentrated and the oil obtained is purified by flash chromatography on silica (petroleum ether:AcOEt 70:30). 1.5 g of triazine 9m is this isolated in the form of oil (quantitative yield). TLC silica gel 60 F 254 Merck, petroleum ether:AcOEt 90:10, Rf=0.38.

d) Intermediates 9n-9o

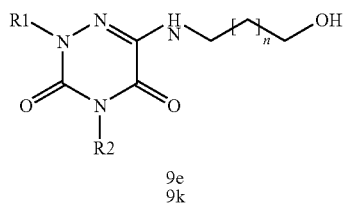

9e
9k

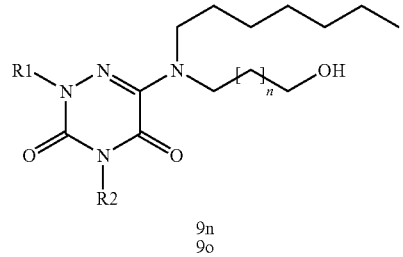

9n
9o

The synthesis of intermediates 9n and 9o is carried out starting from intermediates 9e and 9k, respectively, following the procedure described for the synthesis of 9m using bromo-heptane.

TABLE 9 intermediates 9n-9o

| Starting molecule | Yield | TLC | State | Intermediates 9n-9o |
|---|---|---|---|---|
| 9e | 59% | heptane:AcOEt 50:50 Rf = 0.16 | oil | 9n: 6-[Heptyl-(3-hydroxy-propyl)-amino]-2,4-dimethyl-2H-[1,2,4]triazine-3,5-dione |
| 9k | 59% | heptane:AcOEt 50:50 Rf = 0.24 | oil | 9o: 6-[Heptyl-(4-hydroxy-butyl)-amino]-2,4-dimethyl-2H-[1,2,4]triazine-3,5-dione |

TLC: silica gel 60 F 254 Merck, PE = petroleum ether e) 2-heptyl-6-(2-hydroxy-ethoxy)-4-methyl-2H-[1,2,4]triazine-3,5-dione (9p)

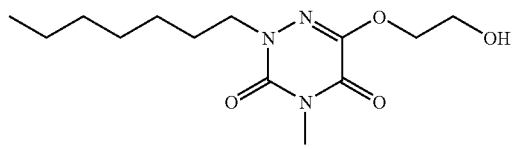

1.5 g (4.9 mmol) of triazine 4b and 0.8 g (5.8 mmol) of K$_2$CO$_3$ are placed in 1.5 ml of ethyleneglycol at 130° C. for 0.5 h. 50 ml of water are added to the reaction medium which is then extracted with AcOEt. After drying on MgSO$_4$, the organic phases are dry concentrated and the residue obtained is purified by flash chromatography on silica (CH$_2$Cl$_2$:AcOEt 70:30). 0.5 g of oil corresponding to intermediate 9p is thus isolated (39% yield). TLC silica gel 60 F 254 Merck, heptane:AcOEt 50:50, Rf=0.08.

f) Intermediates 9q-9s

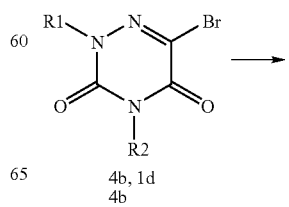

4b, 1d
4b

-continued

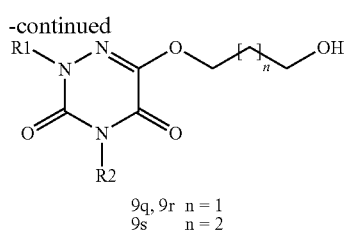

9q, 9r  n = 1
9s      n = 2

The synthesis of intermediates 9q-9s is carried out from starting compounds 4b and 1d according to the procedure described for the synthesis of 9p using various diols.

TABLE 10 intermediates 9q-9s

| Starting molecule | Diol | Yield | TLC | State | Intermediates 9q-9s |
|---|---|---|---|---|---|
| 4b | HO~~~OH | 78% | AcOEt Rf = 0.41 | oil | 9q: 2-Heptyl-6-(3-hydroxy-propoxy)-4-methyl-2H-[1,2,4]triazine-3,5-dione |
| 1d | HO~~~OH | 67% | AcOEt Rf = 0.44 | oil | 9r: 6-(3-Hydroxy-propoxy)-2,4-bis-(4,4,4-trifluoro-butyl)-2H-[1,2,4]triazine-3,5-dione |
| 4b | HO~~~~OH | 70% | AcOEt Rf = 0.31 | oil | 9s: 2-Heptyl-6-(4-hydroxy-butoxy)-4-methyl-2H-[1,2,4]triazine-3,5-dione |

TLC: silica gel 60 F 254 Merck

Intermediate 10:

a) 3-(2-Hydroxy-ethyl)-phenol (10a)

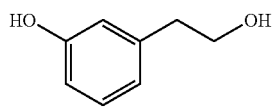

11.3 g of (3-hydroxy-phenyl)-acetic acid (74.2 mmol) are placed in 100 ml of THF at 0° C. under nitrogen. 100 ml of a solution of LiAlH₄ (1 M in THF) is added dropwise at this temperature. The mixture is then placed at 60° C. for 2 h. It is then neutralized slowly with a 6 N HCl solution then extracted with diethyl ether. The organic phases are washed with water, dried on MgSO₄, then dry concentrated. The residue obtained is purified by flash chromatography on silica (CH₂Cl₂:AcOEt 70:30). 9 g of oil corresponding to intermediate 10a are thus isolated (88% yield). TLC silica gel 60 F 254 Merck, CH₂Cl₂:AcOEt 70:30, Rf=0.18.

b) Ethyl 2-(3-hydroxy-phenoxy)-2-methyl-propionate (10b)

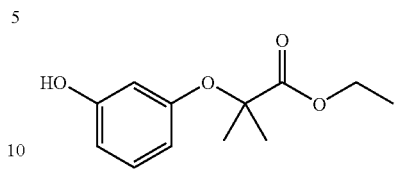

15 g of resorcinol (136 mmol) are added to 120 ml of a solution of sodium (6.3 g, 274 mmol) in ethanol. The mixture is placed at reflux for 1 h then a solution of ethyl bromoisobutyrate (13.2 ml, 90 mmol) in 30 ml of ethanol is added dropwise. Heating is maintained for 3 h then the reaction medium is dry concentrated. The residue obtained is taken up in a solution of water and acetic acid then extracted with AcOEt. The organic phases are washed with water, dried on MgSO₄, then dry concentrated. The residue obtained is purified by flash chromatography on silica (CH₂Cl₂:AcOEt 90:10). 14.4 g of oil corresponding to intermediate 10b are thus isolated (72% yield). TLC silica gel 60 F 254 Merck, CH₂Cl₂:AcOEt 70:30, Rf=0.66.

c) Ethyl 2-(4-hydroxy-phenoxy)-2-methyl-propionate (10c)

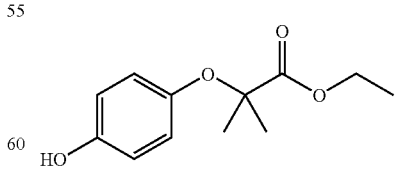

11 g of hydroquinone (100 mmol) in 100 ml of DMF is placed at 80° C. for 2 h. This mixture is cooled at ambient temperature then a solution of ethyl bromoisobutyrate (14.7 ml, 100 mmol) in 30 ml of DMF is added dropwise. The mixture is stirred for 3 h then the reaction medium is dry concentrated. The residue obtained is taken up in a 1 N HCl solution then extracted with AcOEt. The organic phases are washed with water, dried on MgSO₄, then dry concentrated. The residue obtained is purified by flash chromatography on silica (petroleum ether:AcOEt 80:20). 9 g of oil corresponding to intermediate 10c are thus isolated (40% yield). TLC silica gel 60 F 254 Merck, petroleum ether:AcOEt 70:30, Rf=0.50.

d) Ethyl 2-(3-bromo-phenoxy)-2-methyl-propionate (10d)

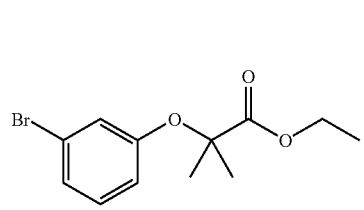

25 g (144.5 mmol) of 3-bromophenol are placed in the presence of K₂CO₃ (21 g, 152 mmol) in 75 ml of ethyl 2-bromoisobutyrate and heated to reflux for 7 h. After elimination of K₂CO₃ by filtration, the reaction medium is dry concentrated. After purification by flash chromatography on silica (petroleum ether:AcOEt 90:10), 37 g of intermediate 10d are collected in the form of clear oil (yield=89%). TLC silica gel 60 F 254 Merck, petroleum ether:AcOEt 90:10, Rf=0.40.

d) Intermediates 10e-10j

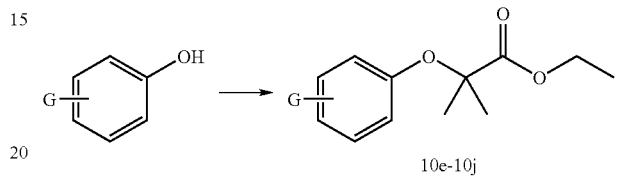

The synthesis of intermediates 10e-10j is carried out from the variously substituted phenols listed in table 8 following the procedure described for the synthesis of 10d.

TABLE 11

| Starting phenol | Yield | TLC | State | Intermediates 10e-10j |
|---|---|---|---|---|
| ![4-bromophenol] | 98% | PE:AcOEt 90:10 Rf = 0.52 | oil | 10e: Ethyl 2-(4-bromo-phenoxy)-2-methyl-propionate |
| ![4-hydroxymethylphenol] | 52% | CH₂Cl₂: AcOEt 80:20 Rf = 0.36 | oil | 10f: Ethyl 2-(4-hydroxymethyl-phenoxy)-2-methyl-propionate |
| ![2-(2-hydroxyethyl)phenol] | 19% | CH₂Cl₂: AcOEt 90:10 Rf = 0.50 | oil | 10g: Ethyl 2-[2-(2-hydroxy-ethyl)-phenoxy]-2-methyl-propionate |
| 10a | 9% | CH₂Cl₂: AcOEt 70:30 Rf = 0.68 | oil | 10h: Ethyl 2-[3-(2-hydroxy-ethyl)-phenoxy]-2-methyl-propionate |
| ![4-(2-hydroxyethyl)phenol] | 61% | CH₂Cl₂: AcOEt 90:10 Rf = 0.21 | oil | 10j: Ethyl 2-[4-(2-hydroxy-ethyl)-phenoxy]-2-methyl-propionate |

TLC: silica gel 60 F 254 Merck, PE = petroleum ether

Intermediate 11:

a) Ethyl 2-(3-bromo-phenylsulfanyl)-2-methyl-propionate (11a)

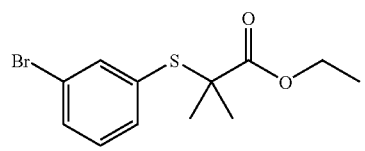

10 g (52.9 mmol) of 3-bromothiophenol are placed in the presence of 9.4 ml (63.5 mmol) of ethyl bromoisobutyrate and 8 g (57.9 mmol) of $K_2CO_3$ in 100 ml of EtOH. This mixture is stirred at reflux for 4 h and then dry concentrated. The residue is taken up in water. After extraction in AcOEt and then drying on $MgSO_4$, the organic phases are dry concentrated. The oil obtained is purified by flash chromatography on silica (petroleum ether:AcOEt 90:10) and 11a is isolated in the form of clear oil (16.8 g, quantitative yield). TLC silica gel 60 F 254 Merck, petroleum ether:AcOEt 90:10, Rf=0.72.

c) Intermediates 11b-11e

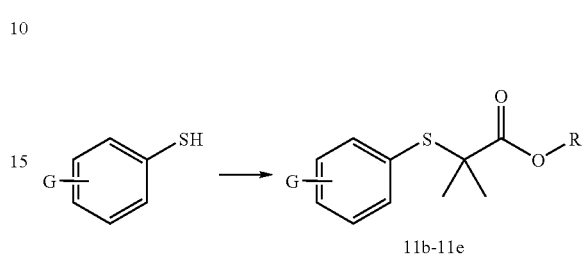

The synthesis of intermediates 11b-11e is carried out starting from variously substituted thiophenols (G) listed in table 12 following the procedure described for the synthesis of 11a using ethyl or tert-butyl bromoisobutyrate.

TABLE 12 intermediates 11b-11e

| Starting thiophenol | | Yield | TLC | State | Intermediates 11b-11e |
|---|---|---|---|---|---|
| Br-C6H4-SH (4-Br) | ethyl bromoisobutyrate | 87% | PE:AcOEt 90:10 Rf = 0.70 | oil | 11b: Ethyl 2-(4-bromo-phenylsulfanyl)-2-methyl-propionate |
| HO-C6H4-SH (3-OH) | ethyl bromoisobutyrate | 74% | Heptane:AcOEt 80:20 Rf = 0.50 | oil | 11c: Ethyl 2-(3-hydroxy-phenylsulfanyl)-2-methyl-propionate |
| HO-C6H4-SH (4-OH) | ethyl bromoisobutyrate | 64% | Heptane:AcOEt 80:20 Rf = 0.20 | oil | 11d: Ethyl 2-(4-hydroxy-phenylsulfanyl)-2-methyl-propionate |
| Br-C6H4-SH (4-Br) | tert-butyl bromoisobutyrate | 98% | PE:AcOEt 90:10 Rf = 0.70 | solid | 11e: Tert-butyl-2-(4-bromo-phenyl-sulfanyl)-2-methyl-propionate |

TLC: silica gel 60 F 254 Merck, PE = petroleum ether

Intermediate 12:

a) Ethyl 2-[3-(3-hydroxy-propyl)-phenoxy]-2-methyl-propionate (12a)

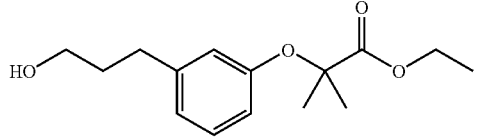

10d (50 g, 175 mmol) is placed in the presence of 2-propynol (12 ml, 210 mmol) in 400 ml of diisopropylamine, under nitrogen. Pd(PPh$_3$)$_2$Cl$_2$ (3.5 g) and CuI (500 mg) are added and the reaction medium is stirred at reflux for 5 h. The precipitate formed in the course of the reaction is filtered on celite and the reaction medium is dry concentrated. The oil obtained is purified by flash chromatography on silica (petroleum ether:AcOEt 80:20). It is then placed in a solution of 250 ml of THF and 150 ml of EtOH in the presence of Pd/C under hydrogen at 6 bar. This mixture is stirred for 24 h. at ambient temperature. After filtration on celite, the reaction medium is dry concentrated and 12a is isolated in the form of a clear oil (32 g, yield=69%). TLC silica gel 60 F 254 Merck, heptane:AcOEt 80:20, Rf=0.56.

b) Intermediates 12b-12e

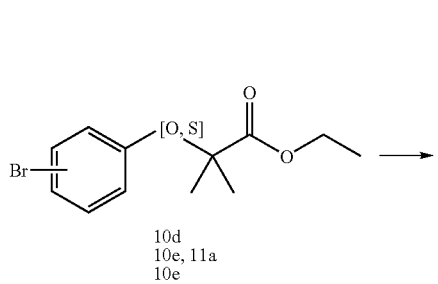

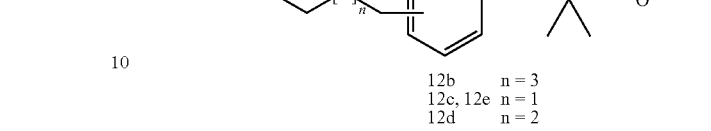

12b   n = 3
12c, 12e   n = 1
12d   n = 2

The synthesis of intermediates 12b-12e is carried out from the starting bromine compounds listed in table 13 following the procedure described for the synthesis of 12a using various alkynols. Note: in the case of a sulfur derivative, a Wilkinson catalyst is used for the hydrogenation step

TABLE 13 intermediates 12b-12e

| Starting molecule | alkynol | Yield | TLC | State | Intermediates 12b-12d |
|---|---|---|---|---|---|
| 10d | HO–⌇–≡ (pentynol) | 76% | Heptane:AcOEt 60-40 Rf = 0.37 | oil | 12b: Ethyl 2-[3-(5-hydroxy-pentyl)-phenoxy]-2-methyl-propionate |
| 10e | HO–≡ (propargyl) | 5% | Heptane:AcOEt 60-40 Rf = 0.33 | oil | 12c: Ethyl 2-[4-(3-hydroxy-propyl)-phenoxy]-2-methyl-propionate |
| 10e | HO–⌇–≡ (butynol) | 55% | PE:AcOEt 80:20 Rf = 0.14 | oil | 12d: Ethyl 2-[4-(4-hydroxy-butyl)-phenoxy]-2-methyl-propionate |
| 11a | HO–≡ (propargyl) | 73% | PE:AcOEt 70:30 Rf = 0.26 | oil | 12e: Ethyl 2-[3-(3-hydroxy-propyl)-phenylsulfanyl]-2-methyl-propionate |

TLC: silica gel 60 F 254 Merck, PE = petroleum ether

Intermediate 13:

a) Ethyl 2-[4-(2-amino-ethyl)-phenoxy]-2-methyl-propionate (13a)

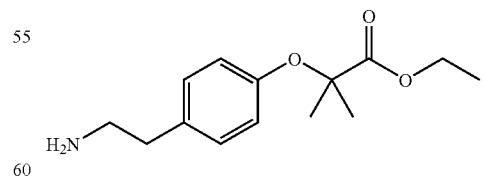

10.1 g (73.6 mmol) of tyramine is placed in the presence of sodium bicarbonate (6.1 g, 72.6 mmol) in a mixture of 100 ml of water and 50 ml of acetone at 0° C. 11.6 ml (81.2 mmol) of benzyl chloroformate is added dropwise at this temperature then the reaction medium is stirred 4 h at ambient temperature. After dry concentration, the residue obtained is taken up in water then extracted with AcOEt. After drying on MgSO₄, the organic phases are dry concentrated and the solid obtained is recrystallized in diethyl ether: 17.2 g of solid is thus obtained (86% yield). They are then placed in 37 ml of ethyl bromoisobutyrate in the presence of 8.8 g (63.7 mmol) of potassium carbonate at 130° C. for 5 h. After filtration, the reaction medium is dry concentrated and the residue obtained is purified by flash chromatography on silica (petroleum ether:AcOEt 70:30). 22.7 g of clear oil are obtained (yield=93%). This oil is then placed in 200 ml of EtOH in the presence of palladium on carbon under, hydrogen at 3 bar and then this solution is stirred for 3 h at ambient temperature. After filtration on celite, the reaction medium is dry concentrated and 14.7 g of intermediate 13a is thus isolated in the form of an oil (quantitative yield). TLC silica gel 60 F 254 Merck, CH₂Cl₂:MeOH 90:10, Rf=0.11.

b) Ethyl 2-[3-(2-amino-ethyl)-phenoxy]-2-methyl-propionate (13b)

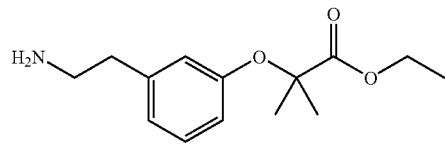

10d (14 g, 49 mmol) is placed in the presence of N-vinylphthalimide (11 g, 63 mmol) and 27 ml (194 mmol) of triethylamine in 160 ml of DMF. Pd(OAc)₂ (0.3 g) and P(oTol)₃ (0.4 g) are added and the reaction medium is stirred for 10 h at 110° C. The reaction medium is dry concentrated and the residue obtained is taken up in water and extracted with AcOEt. After drying on MgSO₄, the organic phases are dry concentrated and the oil isolated is purified by flash chromatography on silica (heptane:AcOEt 90:10). 11.5 g of oil is obtained (62% yield) then placed in a solution of 70 ml of THF and 70 ml of EtOH in the presence of Pd/C under hydrogen at 6 bar. This mixture is stirred for 72 h at ambient temperature. After filtration on celite, the reaction medium is dry concentrated and the residue obtained is purified by flash chromatography on silica (petroleum ether:AcOEt 80:20). 10.9 g of clear oil are obtained (yield=94%). This oil is then placed in 140 ml of EtOH in the presence of 3.5 ml of hydrazine hydrate then this solution is heated at reflux for 4 h. After filtration of the insolubles, the reaction medium is dry concentrated and then the residue obtained is purified by flash chromatography on silica (CH₂Cl₂:MeOH:NH₄OH 90:9:1). 5.7 g of intermediate 13b are thus isolated in the form of an oil (yield=80%). TLC silica gel 60 F 254 Merck, CH₂Cl₂:MeOH:NH₄OH 90:9:1, Rf=0.28.

c) Intermediates 13c-13i

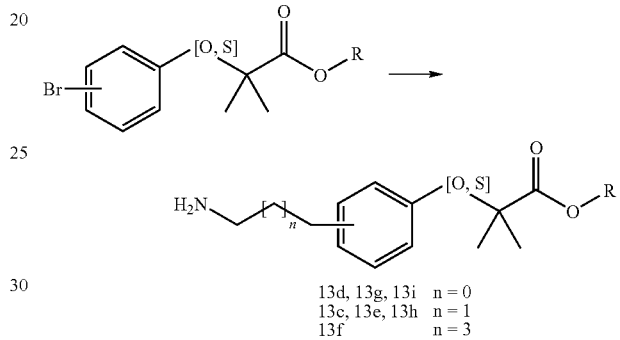

13d, 13g, 13i  n = 0
13c, 13e, 13h  n = 1
13f            n = 3

The synthesis of intermediates 13c-13i is carried out from the starting bromine compounds listed in table 14 following the procedure described for the synthesis of 13b using variously N-alkylated phthalimides. (Note: in the case of a sulfur derivative, a Wilkinson catalyst is used for the hydrogenation step

TABLE 14 intermediates 13b-13i

| Starting molecule | N-substituted phthalimide | Total Yield | TLC Form | State | Intermediates 13c-13h |
|---|---|---|---|---|---|
| 10d | N-allylphthalimide | 80% | CH₂Cl₂:MeOH 90:10 Rf = 0.12 | oil | 13c: Ethyl 2-[3-(3-amino-propyl)-phenoxy]-2-methyl-propionate |
| 11a | N-vinylphthalimide | 66% | CH₂Cl₂:MeOH:NH₄OH 90:9:1 Rf = 0.20 | oil | 13d: Ethyl 2-[3-(2-amino-ethyl)-phenyl-sulfanyl]-2-methyl-propionate |
| 11a | N-allylphthalimide | 70% | CH₂Cl₂:MeOH:NH₄OH 90:9:1 Rf = 0.30 | oil | 13e: Ethyl 2-[3-(3-amino-propyl)-phenylsulfanyl]-2-methyl-propionate |
| 11a | N-but-3-enyl-phthalimide | 38% | CH₂Cl₂:MeOH:NH₄OH 90:9:1 Rf = 0.27 | oil | 13f: Ethyl 2-[3-(4-amino-butyl)-phenyl-sulfanyl]-2-methyl-propionate |
| 11b | N-vinylphthalimide | 41% | CH₂Cl₂:MeOH:NH₄OH 90:9:1 Rf = 0.28 | oil | 13g: Ethyl 2-[4-(2-amino-ethyl)-phenyl-sulfanyl]-2-methyl-propionate |

TABLE 14-continued intermediates 13b-13i

| Starting molecule | N-substituted phthalimide | Total Yield | TLC Form | State | Intermediates 13c-13h |
|---|---|---|---|---|---|
| 11b | N-allylphthalimide | 38% | CH$_2$Cl$_2$:MeOH:NH$_4$OH 90:9:1 Rf = 0.23 | oil | 13h: Ethyl 2-[4-(3-amino-propyl)-phenylsulfanyl]-2-methyl-propionate |
| 11e | N-vinylphthalimide | 63% | CH$_2$Cl$_2$:MeOH 90:10 Rf = 0.18 | oil | 13i: Tert-butyl 2-[4-(2-amino-ethyl)-phenylsulfanyl]-2-methyl-propionate |

TLC: silica gel 60 F 254 Merck b) Intermediates 13j-13n

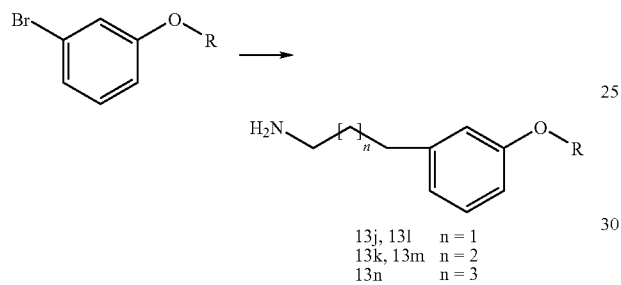

| | |
|---|---|
| 13j, 13l | n = 1 |
| 13k, 13m | n = 2 |
| 13n | n = 3 |

The synthesis of intermediates 13j-13n is carried out from the starting bromine compounds listed in table 15 following the procedures described for the synthesis of 13b using variously N-alkylated phthalimides.

TABLE 15 intermediates 13j-13n

| Starting molecule | | N-substituted phthalimide | Yield | TLC | State | Intermediates 13i-13n |
|---|---|---|---|---|---|---|
| Br—⟨phenyl⟩—OH | | N-allylphthalimide | 47% | CH$_2$Cl$_2$:MeOH:NH$_4$OH 80:18:2 Rf = 0.25 | solid | 13j: 3-(3-Amino-propyl)-phenol |
| Br—⟨phenyl⟩—OH | | N-but-3-enylphthalimide | 49% | CH$_2$Cl$_2$:MeOH:NH$_4$OH 80:18:2 Rf = 0.24 | oil | 13k: 3-(4-Amino-butyl)-phenol |
| Br—⟨phenyl⟩—O— | | N-allylphthalimide | 59% | CH$_2$Cl$_2$:MeOH:NH$_4$OH 80:18:2 Rf = 0.20 | oil | 13l: 3-(3-Methoxy-phenyl)-propylamine |
| Br—⟨phenyl⟩—O— | | N-but-3-enylphthalimide | 77% | CH$_2$Cl$_2$:MeOH:NH$_4$OH 80:18:2 Rf = 0.28 | oil | 13m: 4-(3-Methoxy-phenyl)-butylamine |

TABLE 15-continued intermediates 13j-13n

| Starting molecule | N-substituted phthalimide | Yield | TLC | State | Intermediates 13i-13n |
|---|---|---|---|---|---|
| 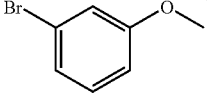 | N-pent-4-enyl-phthalimide | 24% | $CH_2Cl_2$:MeOH:$NH_4OH$ 90:9:1<br>Rf = 0.45 | oil | 13n: 5-(3-Methoxy-phenyl)-pentylamine |

TLC: silica gel 60 F 254 Merck

Intermediate 14:

a) Ethyl 2-[4-(2-heptylamino-ethyl)-phenoxy]-2-methyl-propionate (14a)

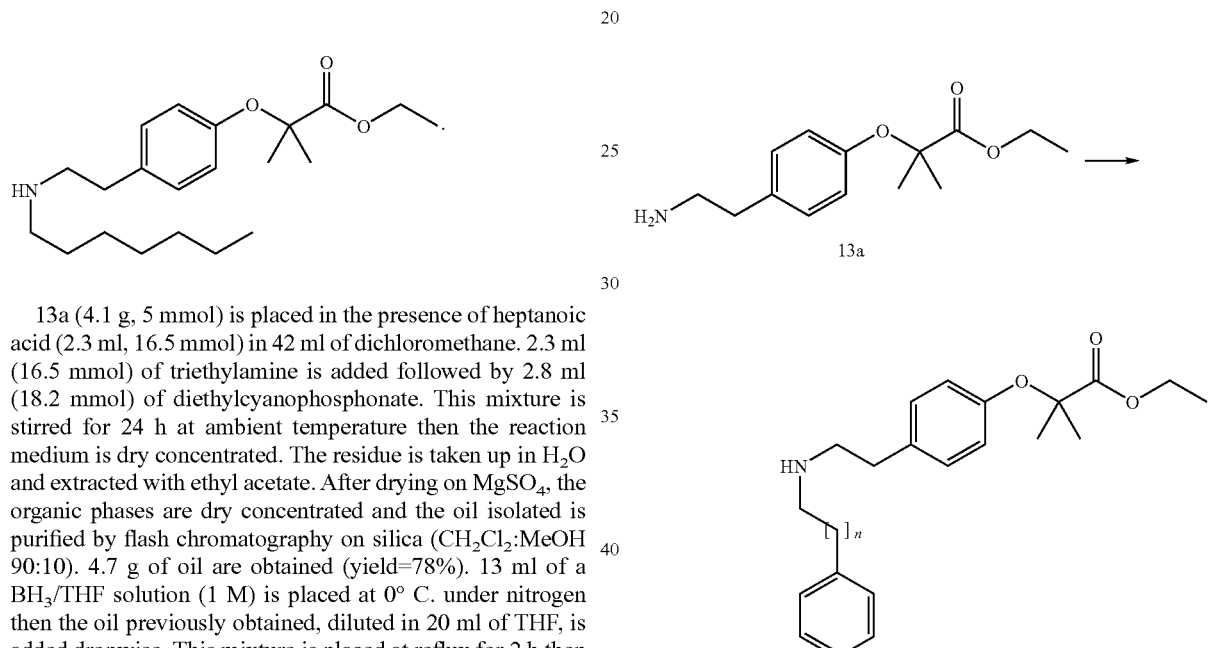

13a (4.1 g, 5 mmol) is placed in the presence of heptanoic acid (2.3 ml, 16.5 mmol) in 42 ml of dichloromethane. 2.3 ml (16.5 mmol) of triethylamine is added followed by 2.8 ml (18.2 mmol) of diethylcyanophosphonate. This mixture is stirred for 24 h at ambient temperature then the reaction medium is dry concentrated. The residue is taken up in $H_2O$ and extracted with ethyl acetate. After drying on $MgSO_4$, the organic phases are dry concentrated and the oil isolated is purified by flash chromatography on silica ($CH_2Cl_2$:MeOH 90:10). 4.7 g of oil are obtained (yield=78%). 13 ml of a $BH_3$/THF solution (1 M) is placed at 0° C. under nitrogen then the oil previously obtained, diluted in 20 ml of THF, is added dropwise. This mixture is placed at reflux for 2 h then neutralized by 10 ml of EtOH/HCl (1.5 N). The solution is again placed at reflux for 1 h then dry concentrated. The residue obtained is taken up in a saturated sodium bicarbonate solution then extracted with dichloromethane. After drying on $MgSO_4$, the organic phases are dry concentrated and the oil isolated is purified by flash chromatography on silica ($CH_2Cl_2$:MeOH 90:10). 1.6 g of intermediate 14a is thus isolated in the form of an oil (yield=73%). TLC silica gel 60 F 254 Merck, $CH_2Cl_2$:MeOH:$NH_4OH$ 90:9:1, Rf=0.50.

b) Intermediates 14b-14c

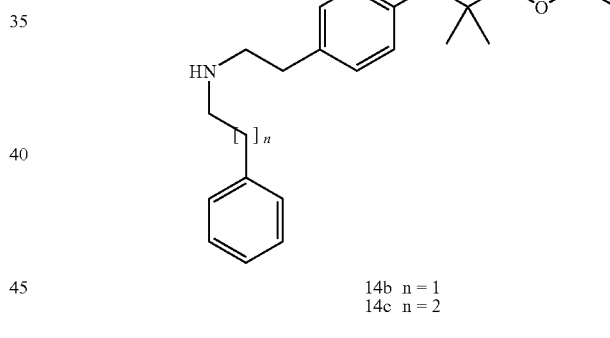

14b n = 1
14c n = 2

The synthesis of intermediates 14b-14c is carried out starting from intermediate 13a according to the procedure described for the synthesis of 14a using various carboxylic acids.

TABLE 16 intermediates 14b-14c

| Carboxylic acid | Total yield | Eluent | Form | Intermediates 14b-14c |
|---|---|---|---|---|
| 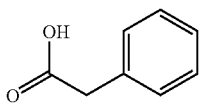 | 78% | $CH_2Cl_2$:MeOH 90:10<br>Rf = 0.37 | oil | 14b: Ethyl 2-methyl-2-[4-(2-phenethylamino-ethyl)-phenoxy]-propionate |

TABLE 16-continued intermediates 14b-14c

| Carboxylic acid | Total yield | Eluent | Form | Intermediates 14b-14c |
|---|---|---|---|---|
| 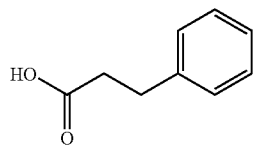 | 65% | CH$_2$Cl$_2$:MeOH 90:10 Rf = 0.44 | oil | 14c: Ethyl 2-methyl-2-{4-[2-(3-phenyl-propylamino)-ethyl]-phenoxy}-propionate |

TLC: silica gel 60 F 254 Merck

EXAMPLES

Example 1

Ethyl 2-{2-[2-(4-butyl-2-methyl-3,5-dioxo-2,3,4,5-tetrahydro-[1,2,4]triazin-6-yloxy)-ethyl]-phenoxy}-2-methyl-propionate (1)

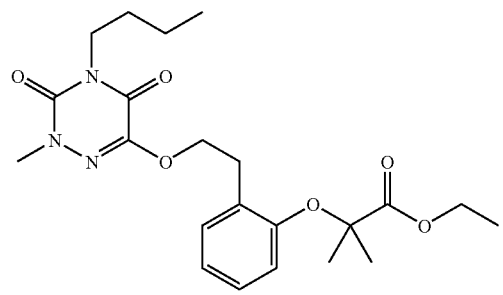

Compound 1 is prepared according to synthesis method 1:1 g (4 mmol) of derivative 10g and 1 g (3.8 mmol) of triazine 5a are placed in 3 ml of DMF in the presence of 0.5 g (3.7 mmol) of K$_2$CO$_3$. This mixture is stirred at 120° C. for 7 h. After filtration and dry concentration of the reaction medium, the residue obtained is purified by flash chromatography on silica (CH$_2$Cl$_2$:AcOEt 98:2). 1.2 g of white crystals are isolated (yield=74%).

TLC silica gel 60 F 254 Merck, CH$_2$Cl$_2$:AcOEt 95:5, Rf=0.40. F=76° C.

RMN $^1$H (CDCl$_3$): 0.94 ppm (t, 3H, J=7.4 Hz), 1.20 ppm (t, 3H, J=7.2 Hz), 1.39 ppm (m, 2H, J=7.5 ppm), 1.63 ppm (m, 8H), 3.16 ppm (t, 0.2H, J=7.6 Hz), 3.50 ppm (s, 3H), 3.95 ppm (t, 2H, J=7.6 Hz), 4.22 ppm (q, 2H, J=7.0 Hz), 4.37 ppm (t, 2H, J=7.6 Hz), 7.00 ppm (m, 4H).

Example 2

Ethyl 2-{3-[2-(2-heptyl-4-methyl-3,5-dioxo-2,3,4,5-tetrahydro-[1,2,4]triazin-6-yloxy)-ethyl]-phenoxy}-2-methyl-propionate (2)

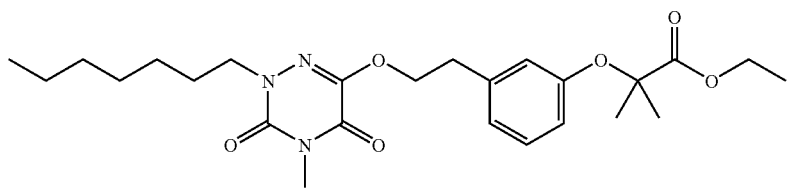

Compound 2 (oil) is prepared from triazine 4b and from intermediate 10h according to synthesis method 1.
TLC silica gel 60 F 254 Merck, CH$_2$Cl$_2$:AcOEt 90:10, Rf=0.62.

Example 3

Ethyl 2-methyl-2-(3-{2-[2-methyl-3,5-dioxo-4-(4,4,4-trifluoro-butyl)-2,3,4,5-tetrahydro-[1,2,4]triazin-6-yloxy]-ethyl}-phenoxy)-propionate (3)

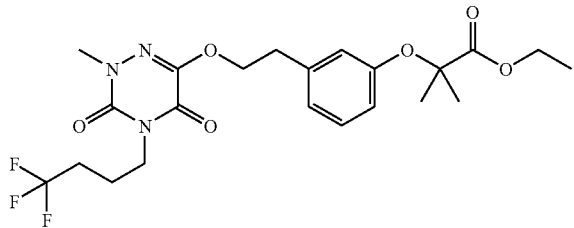

Compound 3 (oil) is prepared from triazine 6a and from intermediate 10h according to synthesis method 1.
TLC silica gel 60 F 254 Merck, CH$_2$Cl$_2$:AcOEt 90:10, Rf=0.57.

Example 4

Ethyl 2-methyl-2-(3-{3-[4-methyl-3,5-dioxo-2-(4,4,4-trifluoro-butyl)-2,3,4,5-tetrahydro-[1,2,4]triazin-6-yloxy]-propyl}-phenoxy)-propionate (4)

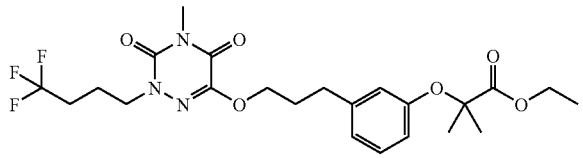

Compound 4 (oil) is prepared from triazine 4a and from intermediate 12a according to synthesis method 1.
TLC silica gel 60 F 254. Merck, petroleum ether:AcOEt 70:30, Rf=0.30.

Example 5

Ethyl 2-{3-[3-(2-heptyl-4-methyl-3,5-dioxo-2,3,4,5-tetrahydro-[1,2,4]triazin-6-yloxy)-propyl]-phenoxy}-2-methyl-propionate (5)

Compound 5 (oil) is prepared from triazine 4b and from intermediate 12a according to synthesis method 1.
TLC silica gel 60 F 254 Merck, petroleum ether:AcOEt 70:30, Rf=0.52.

Example 6

Ethyl 2-methyl-2-(3-{3-[2-methyl-3,5-dioxo-4-(4,4,4-trifluoro-butyl)-2,3,4,5-tetrahydro-[1,2,4]triazin-6-yloxy]-propyl}-phenoxy)-propionate (6)

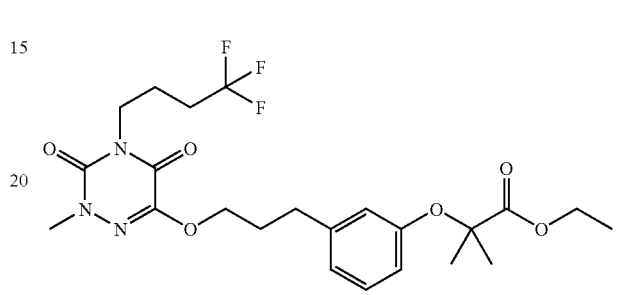

Compound 6 (oil) is prepared from triazine 6a and from intermediate 12a according to synthesis method 1.
TLC silica gel 60 F 254 Merck, petroleum ether:AcOEt 70:30, Rf=0.46.

Example 7

Ethyl 2-{3-[3-(4-heptyl-2-methyl-3,5-dioxo-2,3,4,5-tetrahydro-[1,2,4]triazin-6-yloxy)-propyl]-phenoxy}-2-methyl-propionate (7)

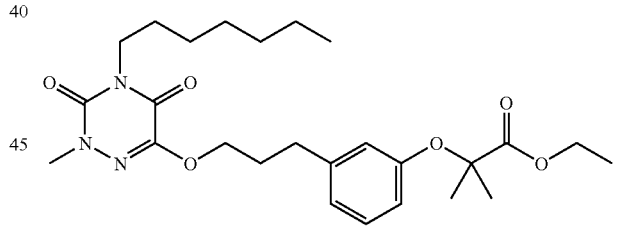

Compound 7 (oil) is prepared from triazine 7a and from intermediate 12a according to synthesis method 1.
TLC silica gel 60 F 254 Merck, petroleum ether:AcOEt 70:30, Rf=0.61.

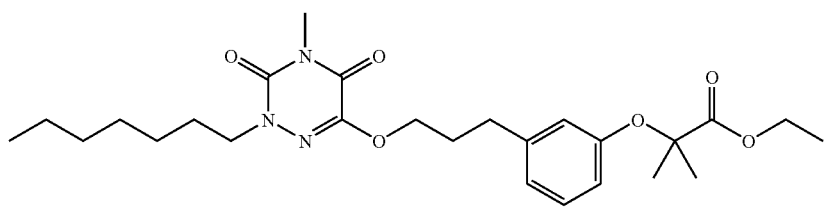

Example 8

Ethyl 2-(3-{3-[4-heptyl-3,5-dioxo-2-(4,4,4-trifluoro-butyl)-2,3,4,5-tetrahydro-[1,2,4]triazin-6-yloxy]-propyl}-phenoxy)-2-methyl-propionate (8)

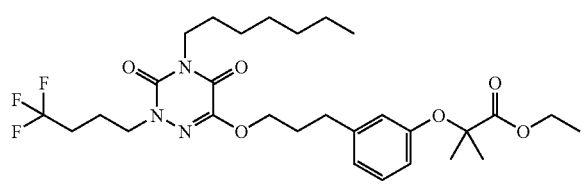

Compound 8 (oil) is prepared from triazine 7b and from intermediate 12a according to synthesis method 1.
TLC silica gel 60 F 254 Merck, petroleum ether:AcOEt 70:30, Rf=0.53.

Example 9

Ethyl 2-methyl-2-(3-{5-[4-methyl-3,5-dioxo-2-(4,4,4-trifluoro-butyl)-2,3,4,5-tetrahydro-[1,2,4]triazin-6-yloxy]-pentyl}-phenoxy)-propionate (9)

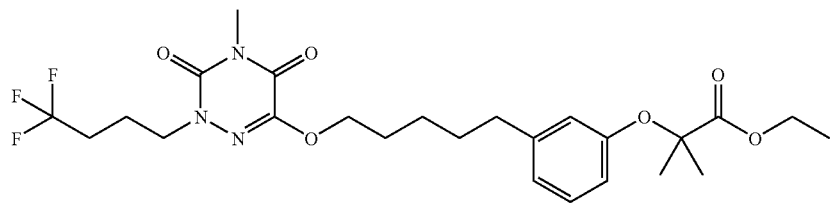

Compound 9 (oil) is prepared from triazine 4a and from intermediate 12b according to synthesis method 1.
TLC silica gel 60 F 254 Merck, petroleum ether:AcOEt 80:20, Rf=0.34.

Example 10

Ethyl 2-{3-[5-(2-heptyl-4-methyl-3,5-dioxo-2,3,4,5-tetrahydro-[1,2,4]triazin-6-yloxy)-pentyl]-phenoxy}-2-methyl-propionate (10)

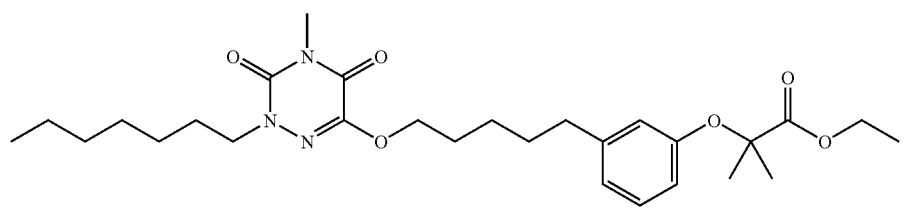

Compound 10 (oil) is prepared from triazine 4b and from intermediate 12b according to synthesis method 1.
TLC silica gel 60 F 254 Merck, petroleum ether:AcOEt 70:30, Rf=0.54.

Example 11

Ethyl 2-{3-[5-(4-butyl-2-methyl-3,5-dioxo-2,3,4,5-tetrahydro-[1,2,4]triazin-6-yloxy)-pentyl]-phenoxy}-2-methyl-propionate (11)

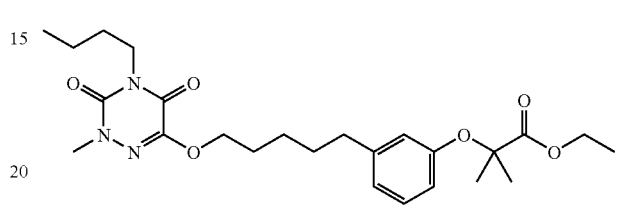

Compound 11 (oil) is prepared from triazine 5a and from intermediate 12b according to synthesis method 1.
TLC silica gel 60. F 254 Merck, petroleum ether:AcOEt 80:20, Rf=0.29.

Example 12

2-{3-[5-(4-Butyl-2-methyl-3,5-dioxo-2,3,4,5-tetrahydro-[1,2,4]triazin-6-yloxy)-pentyl]-phenoxy}-2-methyl-propionic Acid (12)

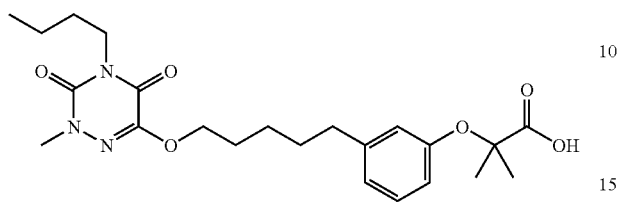

Compound 12 (oil) is prepared by hydrolysis of compound 11 (HCl 12 N, reflux, 16 h, 62%).
TLC silica gel 60 F 254 Merck, $CH_2Cl_2$:MeOH 90:10, Rf=0.43.

Example 13

Ethyl 2-{3-[5-(2,4-dibutyl-3,5-dioxo-2,3,4,5-tetrahydro-[1,2,4]triazin-6-yloxy)-pentyl]-phenoxy}-2-methyl-propionate (13)

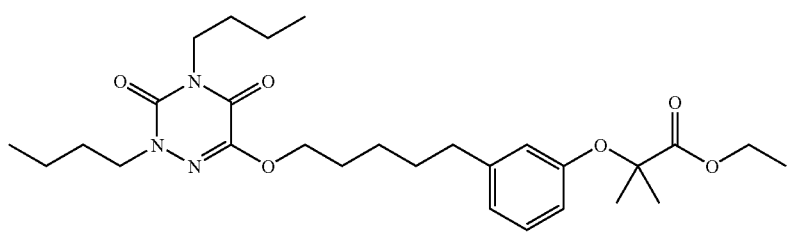

Compound 13 (oil) is prepared from triazine 1c and from intermediate 12b according to synthesis method 1.
TLC silica gel 60 F 254 Merck, petroleum ether:AcOEt 80:20, Rf=0.63.

Example 14

Ethyl 2-(3-{5-[4-Butyl-3,5-dioxo-2-(4,4,4-trifluorobutyl)-2,3,4,5-tetrahydro-[1,2,4]triazin-6-yloxy]-pentyl}-phenoxy)-2-methyl-propionate (14)

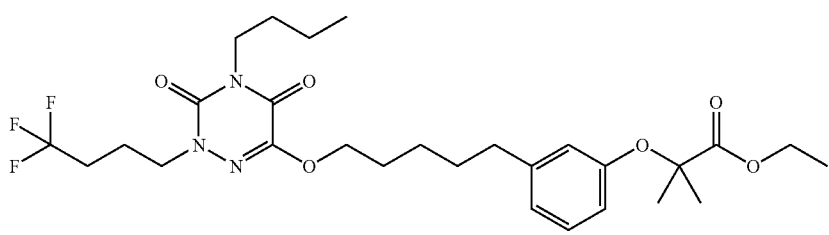

Compound 14 (oil) is prepared from triazine 5b and from intermediate 12b according to synthesis method 1.

TLC silica gel 60 F 254 Merck, petroleum ether:AcOEt 80:20, Rf=0.35.

Example 15

Ethyl 2-{3-[5-(4-butyl-2-heptyl-3,5-dioxo-2,3,4,5-tetrahydro-[1,2,4]triazin-6-yloxy)-pentyl]-phenoxy}-2-methyl-propionate (15)

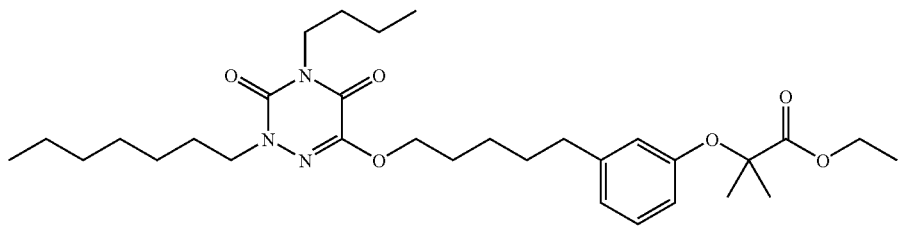

Compound 15 (oil) is prepared from triazine 5c and from intermediate 12b according to synthesis method 1.

TLC silica gel 60 F 254 Merck, petroleum ether:AcOEt 80:20, Rf=0.53.

Example 16

Ethyl 2-methyl-2-(3-{5-[2-methyl-3,5-dioxo-4-(4,4,4-trifluoro-butyl)-2,3,4,5-tetrahydro-[1,2,4]triazin-6-yloxy]-pentyl}-phenoxy)-propionate (16)

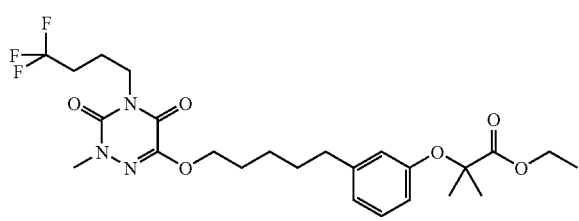

Compound 16 (oil) is prepared from triazine 6a and from intermediate 12b according to synthesis method 1.

TLC silica gel 60 F 254 Merck, petroleum ether:AcOEt 80:20, Rf=0.33.

Example 17

Ethyl 2-{3-[5-(4-heptyl-2-methyl-3,5-dioxo-2,3,4,5-tetrahydro-[1,2,4]triazin-6-yloxy)-pentyl]-phenoxy}-2-methyl-propionate (17)

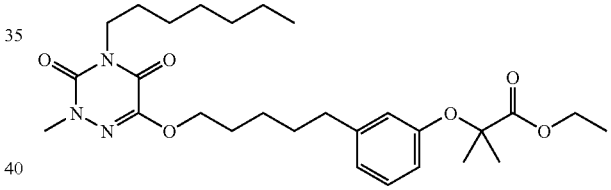

Compound 17 (oil) is prepared from triazine 7a and from intermediate 12b according to synthesis method 1.

TLC silica gel 60 F 254 Merck, petroleum ether:AcOEt 80:20, Rf=0.36.

Example 18

Ethyl 2-(3-{5-[4-heptyl-3,5-dioxo-2-(4,4,4-trifluoro-butyl)-2,3,4,5-tetrahydro-[1,2,4]triazin-6-yloxy]-pentyl}-phenoxy)-2-methyl-propionate (18)

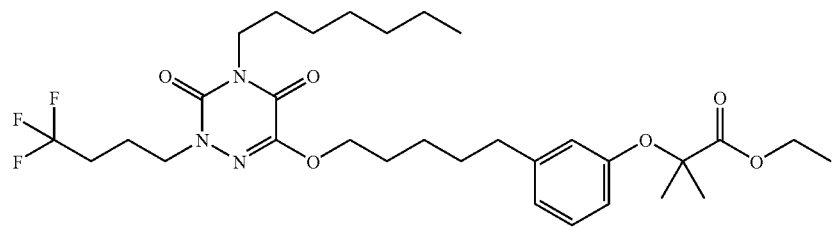

Compound 18 (oil) is prepared from triazine 7b and from intermediate 12b according to synthesis method 1.

TLC silica gel 60 F 254 Merck, heptane:AcOEt 70:30, Rf=0.35.

Example 19

Ethyl 2-{3-[5-(2-benzyl-4-heptyl-3,5-dioxo-2,3,4,5-tetrahydro-[1,2,4]triazin-6-yloxy)-pentyl]-phenoxy}-2-methyl-propionate (19)

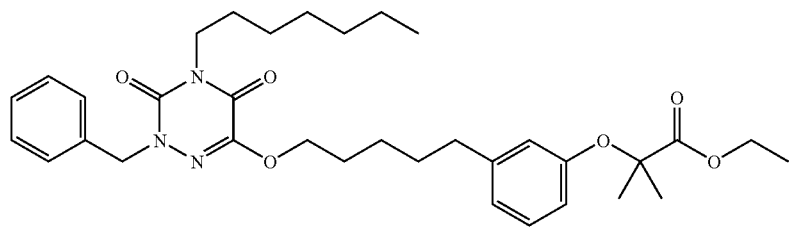

Compound 19 (oil) is prepared from triazine 7c and from intermediate 12b according to synthesis method 1.

TLC silica gel 60 F 254 Merck, petroleum ether:AcOEt 80:20, Rf=0.51.

Example 20

Ethyl 2-[4-(2-heptyl-4-methyl-3,5-dioxo-2,3,4,5-tetrahydro-[1,2,4]triazin-6-yloxymethyl)-phenoxy]-2-methyl-propionate (20)

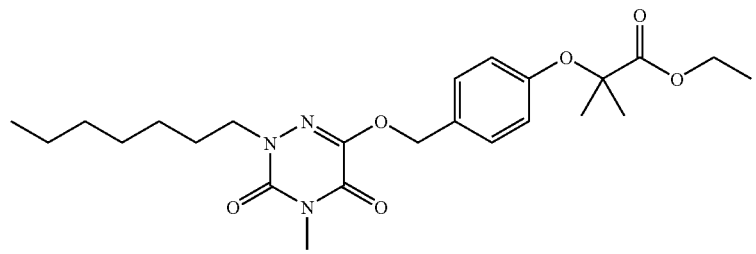

Compound 20 (oil) is prepared from triazine 4b and from intermediate 10f according to synthesis method 1.

TLC silica gel 60 F 254 Merck, petroleum ether:AcOEt 80:20, Rf=0.28.

Example 21

Ethyl 2-methyl-2-{4-[2-methyl-3,5-dioxo-4-(4,4,4-trifluoro-butyl)-2,3,4,5-tetrahydro-[1,2,4]triazin-6-yloxymethyl]-phenoxy}-propionate (21)

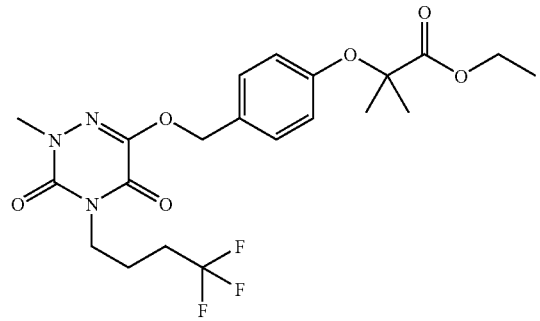

Compound 21 (oil) is prepared from triazine 6a and from intermediate 10f according to synthesis method 1.

TLC silica gel 60 F 254 Merck, petroleum ether:AcOEt 60:40, Rf=0.46.

Example 22

Ethyl 2-[4-(4-heptyl-2-methyl-3,5-dioxo-2,3,4,5-tetrahydro-[1,2,4]triazin-6-yloxymethyl)-phenoxy]-2-methyl-propionate (22)

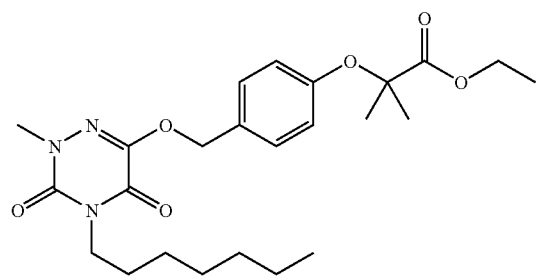

Compound 22 (oil) is prepared from triazine 7a and from intermediate 10f according to synthesis method 1.

TLC silica gel 60 F 254 Merck, petroleum ether:AcOEt 80:20, Rf=0.34.

Example 23

Ethyl 2-{4-[4-heptyl-3,5-dioxo-2-(4,4,4-trifluoro-butyl)-2,3,4,5-tetrahydro-[1,2,4]triazin-6-yloxymethyl]-phenoxy}-2-methyl-propionate (23)

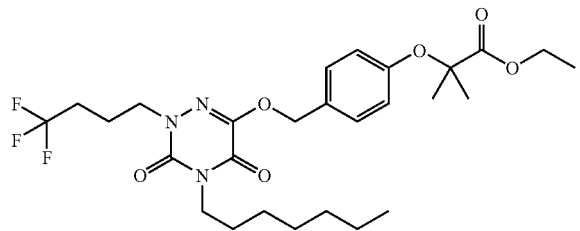

Compound 23 (oil) is prepared from triazine 7b and from intermediate 10f according to synthesis method 1.

TLC silica gel 60 F 254 Merck, petroleum ether:AcOEt 90:10, Rf=0.61.

Example 24

Ethyl 2-methyl-2-(4-{2-[4-methyl-3,5-dioxo-2-(4,4,4-trifluoro-butyl)-2,3,4,5-tetrahydro-[1,2,4]triazin-6-yloxy]-ethyl}-phenoxy)-propionate (24)

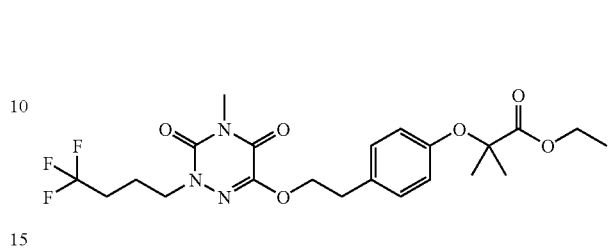

Compound 24 (oil) is prepared from triazine 4a and from intermediate 10j according to synthesis method 1.

TLC silica gel 60 F 254 Merck, $CH_2Cl_2$:AcOEt 90:10, Rf=0.45.

Example 25

Ethyl 2-{4-[2-(2-heptyl-4-methyl-3,5-dioxo-2,3,4,5-tetrahydro-[1,2,4]triazin-6-yloxy)-ethyl]-phenoxy}-2-methyl-propionate (25)

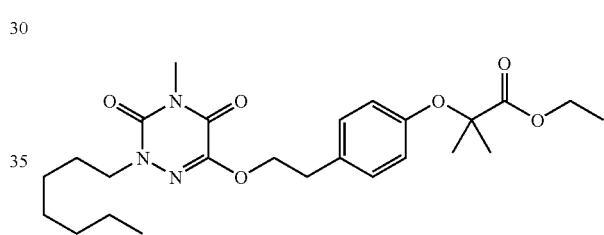

Compound 25 (oil) is prepared from triazine 4b and from intermediate 10j according to synthesis method 1.

TLC silica gel 60 F 254 Merck, petroleum ether:AcOEt 80:20, Rf=0.45.

Example 26

Ethyl 2-{4-[2-(4-heptyl-2-methyl-3,5-dioxo-2,3,4,5-tetrahydro-[1,2,4]triazin-6-yloxy)-ethyl]-phenoxy}-2-methyl-propionate (26)

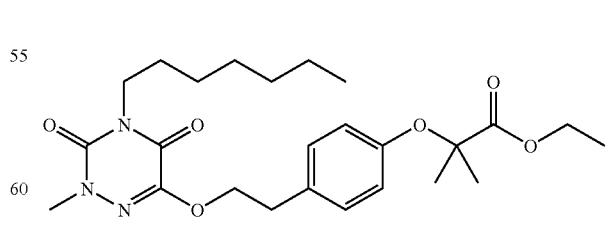

Compound 26 (oil) is prepared from triazine 7a and from intermediate 10j according to synthesis method 1.

TLC silica gel 60 F 254 Merck, petroleum ether:AcOEt 70:30, Rf=0.46.

Example 27

Ethyl 2-{4-[3-(2-heptyl-4-methyl-3,5-dioxo-2,3,4,5-tetrahydro-[1,2,4]triazin-6-yloxy)-propyl]-phenoxy}-2-methyl-propionate (27)

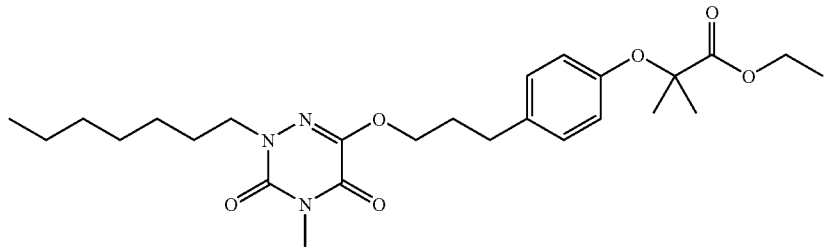

Compound 27 (oil) is prepared from triazine 4b and from intermediate 12c according to synthesis method 1.
TLC silica gel 60 F 254 Merck, petroleum ether:AcOEt 70:30, Rf=0.33.

Example 28

Ethyl 2-methyl-2-(4-{4-[4-methyl-3,5-dioxo-2-(4,4,4-trifluoro-butyl)-2,3,4,5-tetrahydro-[1,2,4]triazin-6-yloxy]-butyl}-phenoxy)-propionate (28)

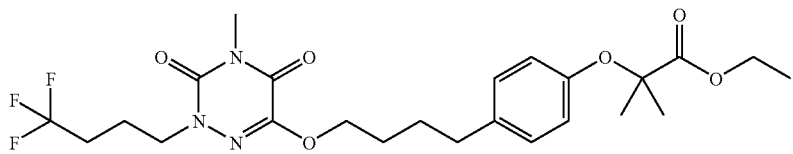

Compound 28 (oil) is prepared from triazine 4a and from intermediate 12d according to synthesis method 1.
TLC silica, gel 60 F 254 Merck, petroleum ether:AcOEt 70:30, Rf=0.31.

Example 29

Ethyl 2-{4-[4-(2-heptyl-4-methyl-3,5-dioxo-2,3,4,5-tetrahydro-[1,2,4]triazin-6-yloxy)-butyl]-phenoxy}-2-methyl-propionate (29)

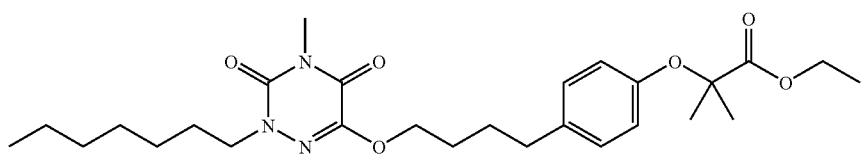

Compound 29 (oil) is prepared from triazine 4b and from intermediate 12d according to synthesis method 1.

TLC silica gel 60 F 254 Merck, petroleum ether:AcOEt 70:30, Rf=0.49.

Example 30

Ethyl 2-methyl-2-(4-{4-[2-methyl-3,5-dioxo-4-(4,4,4-trifluoro-butyl)-2,3,4,5-tetrahydro-[1,2,4]triazin-6-yloxy]-butyl}-phenoxy)-propionate (30)

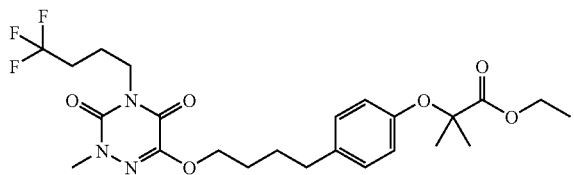

Compound 30 (oil) is prepared from triazine 6a and from intermediate 12d according to synthesis method 1.

TLC silica gel 60 F 254 Merck, petroleum ether AcOEt 70:30, Rf=0.35.

Example 31

Ethyl 2-(4-{4-[4-heptyl-3,5-dioxo-2-(4,4,4-trifluoro-butyl)-2,3,4,5-tetrahydro-[1,2,4]triazin-6-yloxy]-butyl}-phenoxy)-2-methyl-propionate (31)

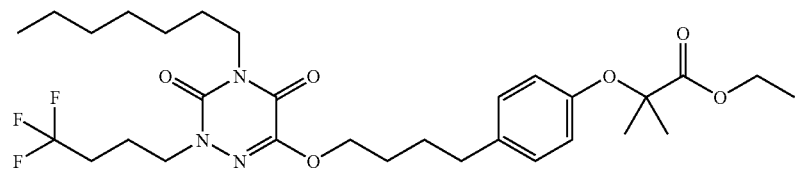

Compound 31 (oil) is prepared from triazine 7b' and from intermediate 12d according to synthesis method 1.

TLC silica gel 60 F 254 Merck, petroleum ether:AcOEt 80:20, Rf=0.51.

Example 32

Ethyl 2-{3-[3-(2-heptyl-4-methyl-3,5-dioxo-2,3,4,5-tetrahydro-[1,2,4]triazin-6-yloxy)-propyl]-phenylsulfanyl}-2-methyl-propionate (32)

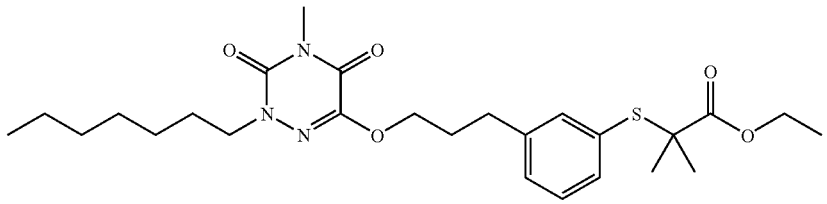

Compound 32 (oil) is prepared from triazine 4b and from intermediate 12e according to synthesis method 1.

TLC silica gel 60 F 254 Merck, petroleum ether:AcOEt 80:20, Rf=0.37.

Example 33

Ethyl 2-{3-[3-(2-heptyl-4-methyl-3,5-dioxo-2,3,4,5-tetrahydro-[1,2,4]triazin-6-yloxy)-propoxy]-phenoxy}-2-methyl-propionate (33)

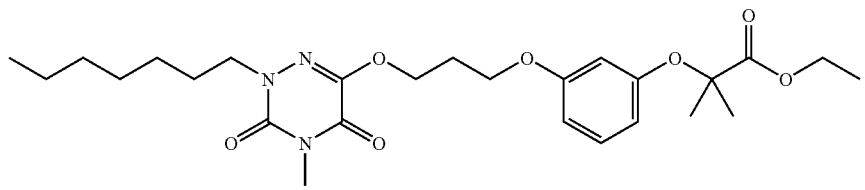

Compound 33 is prepared according to synthesis method 2: 1.1 g (3.7 mmol) of triazine 9q, 0.83 g (3.7 mmol) of ester 10b and 1.25 g (4.7 mmol) of PPh$_3$ are placed in 30 ml of THF at 40° C. 0.74 ml (4.7 mmol) of DEAD diluted in 10 ml of THF is added dropwise and the mixture is stirred for 1 h at 40° C. Afterwards, the reaction medium is dry concentrated and the residue obtained is purified by flash chromatography on neutral alumina (heptane:AcOEt 80:20). 0.8 g of compound 33 is isolated in the form of clear oil (yield=43%).

TLC silica gel 60 F 254 Merck, heptane:AcOEt 50:50, Rf=0.30.

Example 34

Ethyl 2-{3-[3-(2-heptyl-4-methyl-3,5-dioxo-2,3,4,5-tetrahydro-[1,2,4]triazin-6-yloxy)-propoxy]-phenyl-sulfanyl}-2-methyl-propionate (34)

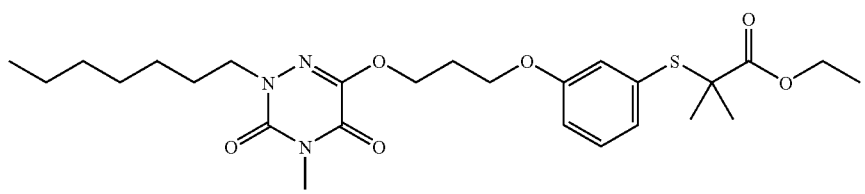

Compound 34 (oil) is prepared from triazine 9q and from intermediate 11c according to synthesis method 2.

TLC silica gel 60 F 254 Merck, heptane:AcOEt 50:50, Rf=0.33.

Example 35

Ethyl 2-(3-{3-[3,5-dioxo-2,4-bis-(4,4,4-trifluoro-butyl)-2,3,4,5-tetrahydro-[1,2,4]triazin-6-yloxy]-propoxy}-phenoxy)-2-methyl-propionate (35)

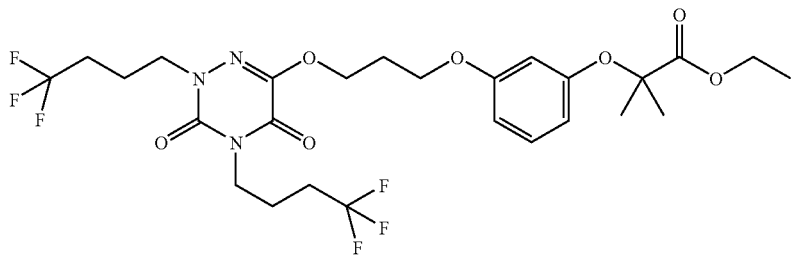

Compound 35 (oil) is prepared from triazine 9r and from intermediate 10b according to synthesis method 2.

TLC silica gel 60 F 254 Merck, heptane:AcOEt 50:50, Rf=0.50.

Example 36

Ethyl 2-{3-[4-(2-heptyl-4-methyl-3,5-dioxo-2,3,4,5-tetrahydro-[1,2,4]triazin-6-yloxy)-butoxy]-phenoxy}-2-methyl-propionate (36)

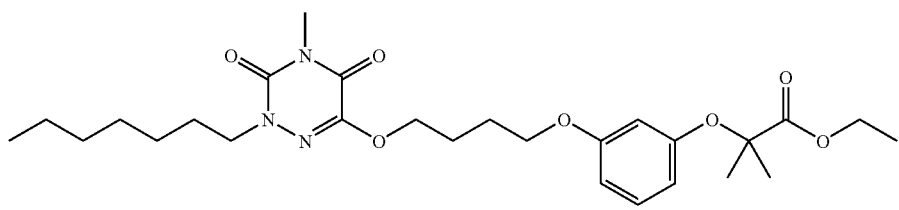

Compound 36 (oil) is prepared from triazine 9s and from intermediate 10b according to synthesis method 2.

TLC silica gel 60 F 254 Merck, heptane:AcOEt 50:50, Rf=0.34.

Example 37

Ethyl 2-{3-[4-(2-heptyl-4-methyl-3,5-dioxo-2,3,4,5-tetrahydro-[1,2,4]triazin-6-yloxy)-butoxy]-phenyl-sulfanyl}-2-methyl-propionate (37)

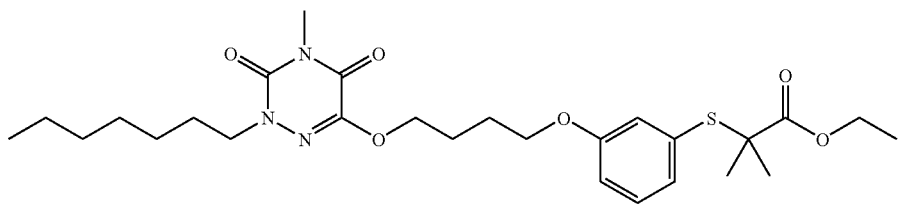

Compound 37 (oil) is prepared from triazine 9s and from intermediate 11c according to synthesis method 2.

TLC silica gel 60 F 254 Merck, heptane:AcOEt 50:50, Rf=0.37.

Example 38

Ethyl 2-{4-[2-(2-heptyl-4-methyl-3,5-dioxo-2,3,4,5-tetrahydro-[1,2,4]triazin-6-yloxy)-ethoxy]-phenyl-sulfanyl}-2-methyl-propionate (38)

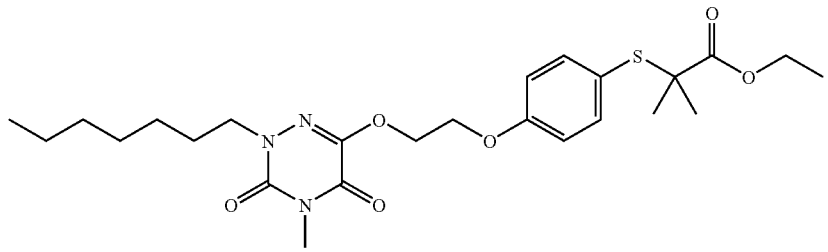

Compound 38 (oil) is prepared from triazine 9p and from intermediate 11d according to synthesis method 2.

TLC silica gel 60 F 254 Merck, heptane:AcOEt 50:50, Rf=0.33.

Example 39

Ethyl 2-(4-{3-[3,5-dioxo-2,4-bis-(4,4,4-trifluoro-butyl)-2,3,4,5-tetrahydro-[1,2,4]triazin-6-yloxy]-propoxy}-phenoxy)-2-methyl-propionate (39)

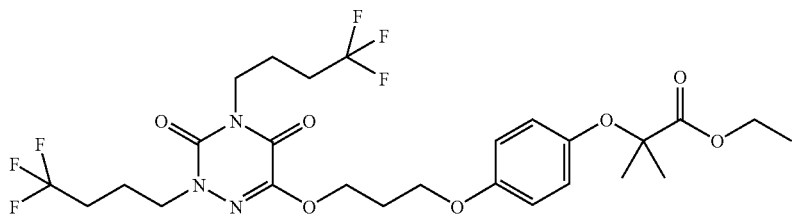

Compound 39 (oil) is prepared from triazine 9r and from intermediate 10c according to synthesis method 2.

TLC silica gel 60 F 254 Merck, heptane:AcOEt 50:50, Rf=0.50.

Example 40

Ethyl 2-{4-[2-(2-heptyl-4-methyl-3,5-dioxo-2,3,4,5-tetrahydro-[1,2,4]triazin-6-ylamino)-ethoxy]-phenoxy}-2-methyl-propionate (40)

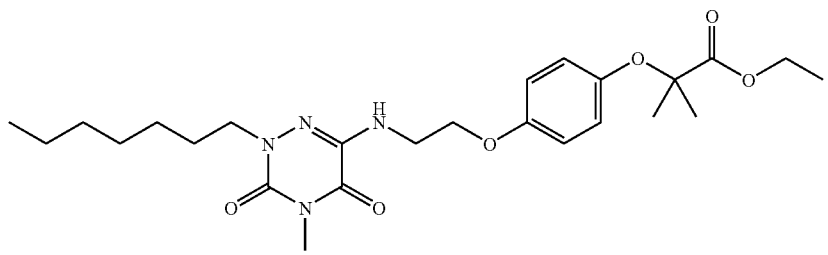

Compound 40 (oil) is prepared from triazine 9b and from intermediate 10c according to synthesis method 2.

TLC silica gel 60 F 254 Merck, petroleum ether:AcOEt 80:20, Rf=0.29.

Example 41

Ethyl 2-(4-{2-[3,5-dioxo-2,4-bis-(4,4,4-trifluoro-butyl)-2,3,4,5-tetrahydro-[1,2,4]triazin-6-ylamino]-ethoxy}-phenoxy)-2-methyl-propionate (41)

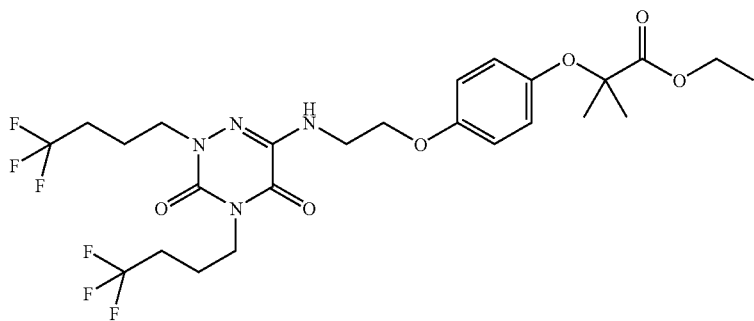

Compound 41 (oil) is prepared from triazine 9a and from intermediate 10c according to synthesis method 2.

TLC silica gel 60 F 254 Merck, petroleum ether:AcOEt 80:20, Rf=0.50.

Example 42

Ethyl 2-{4-[2-(2,4-diheptyl-3,5-dioxo-2,3,4,5-tetrahydro-[1,2,4]triazin-6-ylamino)-ethoxy]-phenoxy}-2-methyl-propionate (42)

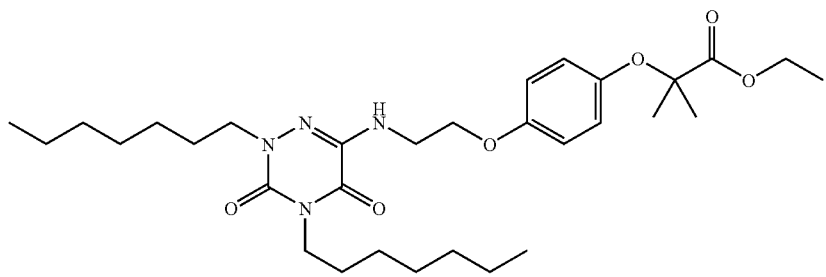

Compound 42 (oil) is prepared from triazine 9c and from intermediate 10c according to synthesis method 2.

TLC silica gel 60 F 254 Merck, petroleum ether:AcOEt 80:20, Rf=0.85.

Example 43

Ethyl 2-(4-{2-[2,4-bis-(3-cyclohexylpropyl)-3,5-dioxo-2,3,4,5-tetrahydro-[1,2,4]triazin-6-ylamino]-ethoxy}-phenoxy)-2-methyl-propionate (43)

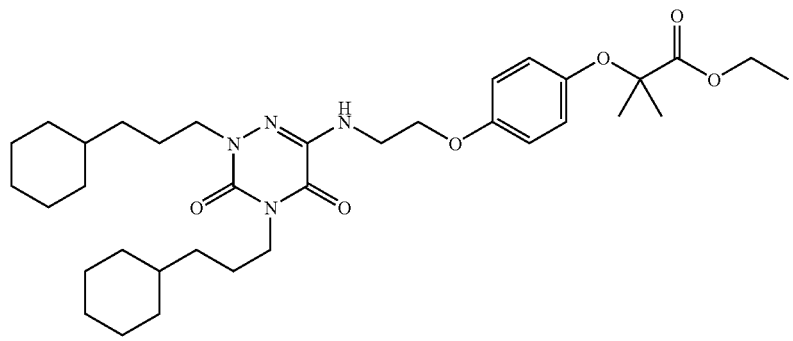

Compound 43 (oil) is prepared from triazine 9d and from intermediate 10c according to synthesis method 2.

TLC silica gel 60 F 254 Merck, heptane:AcOEt 80:20, Rf=0.85.

Example 44

Ethyl 2-methyl-2-(4-{3-[4-methyl-3,5-dioxo-2-(4,4,4-trifluoro-butyl)-2,3,4,5-tetrahydro-[1,2,4]triazin-6-ylamino]-propoxy}-phenoxy)-propionate (44)

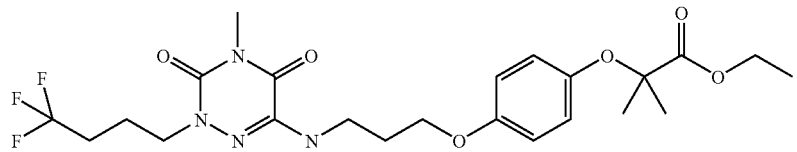

Compound 44 (oil) is prepared from triazine 9f and from intermediate 10c according to synthesis method 2.

TLC silica gel 60 F 254 Merck, petroleum ether:AcOEt 70:30, Rf=0.36.

Example 45

Ethyl 2-{4-[3-(2-heptyl-4-methyl-3,5-dioxo-2,3,4,5-tetrahydro-[1,2,4]triazin-6-ylamino)-propoxy]-phenoxy}-2-methyl-propionate (45)

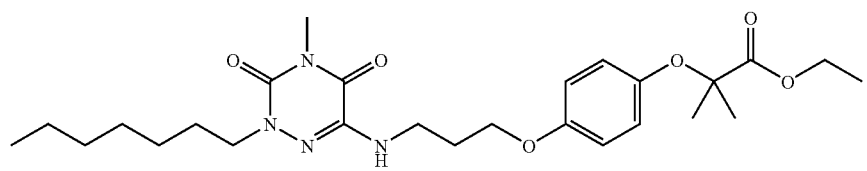

Compound 45 (oil) is prepared from triazine 9g and from intermediate 10c according to synthesis method 2.

TLC silica gel 60 F 254 Merck, petroleum ether:AcOEt 70:30, Rf=0.48.

Example 46

Ethyl 2-methyl-2-(4-{3-[2-methyl-3,5-dioxo-4-(4,4,4-trifluoro-butyl)-2,3,4,5-tetrahydro-[1,2,4]triazin-6-ylamino]-propoxy}-phenoxy)-propionate (46)

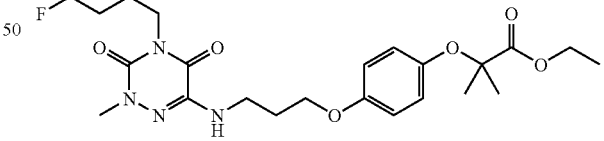

Compound 46 (solid) is prepared from triazine 9h and from intermediate 10c according to synthesis method 2.

TLC silica gel 60 F 254 Merck, petroleum ether:AcOEt 70:30, Rf=0.37. F=116° C.

Example 47

Ethyl 2-{4-[3-(4-heptyl-4-methyl-3,5-dioxo-2,3,4,5-tetrahydro-[1,2,4]triazin-6-ylamino)-propoxy]-phenoxy}-2-methyl-propionate (47)

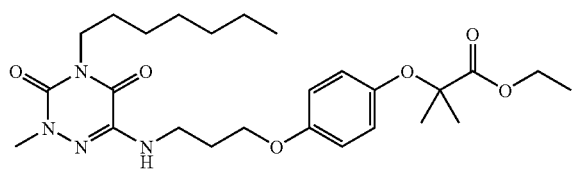

Compound 47 (oil) is prepared from triazine 9i and from intermediate 10c according to synthesis method 2.

TLC silica gel 60 F 254 Merck, petroleum ether:AcOEt 80:20, Rf=0.30.

Example 48

Ethyl 2-(4-{3-[4-heptyl-3,5-dioxo-2-(4,4,4-trifluoro-butyl)-2,3,4,5-tetrahydro-[1,2,4]triazin-6-ylamino]-propoxy}-phenoxy)-2-methyl-propionate (48)

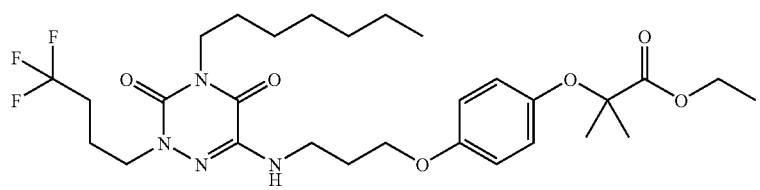

Compound 48 (oil) is prepared from triazine 9j and from intermediate 10c according to synthesis method 2.

TLC silica gel 60 F 254 Merck, petroleum ether:AcOEt 80:20, Rf=0.50.

Example 49

Ethyl 2-{4-[3-(4-heptyl-2-methyl-3,5-dioxo-2,3,4,5-tetrahydro-[1,2,4]triazin-6-ylamino)-propoxy]-phenylsulfanyl}-2-methyl-propionate (49)

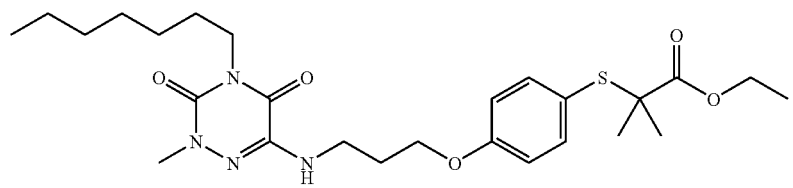

Compound 49 (oil) is prepared from triazine 9i and from intermediate 11d according to synthesis method 2.

TLC silica gel 60 F 254 Merck, petroleum ether:AcOEt 80:20, Rf=0.46.

Example 50

Ethyl 2-{4-[4-(4-heptyl-2-methyl-3,5-dioxo-2,3,4,5-tetrahydro-[1,2,4]triazin-6-ylamino)-butoxy]-phenoxy}-2-methyl-propionate (50)

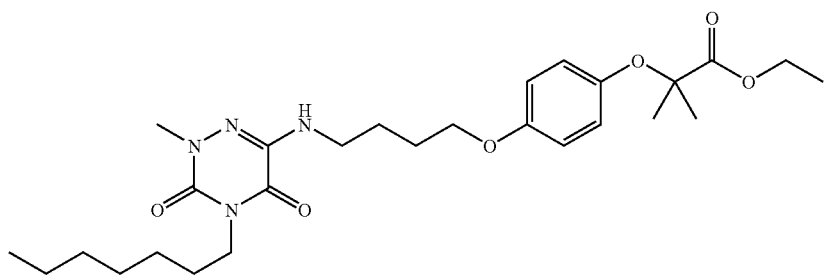

Compound 50 (oil) is prepared from triazine 9i and from intermediate 10c according to synthesis method 2.

TLC silica gel 60. F 254 Merck, petroleum ether:AcOEt 80:20, Rf=0.50.

Example 51

Ethyl 2-(3-{3-[(2-heptyl-4-methyl-3,5-dioxo-2,3,4,5-tetrahydro-[1,2,4]triazin-6-yl)-(4,4,4-trifluoro-butyl)-amino]-propoxy}-phenoxy)-2-methyl-propionate (51)

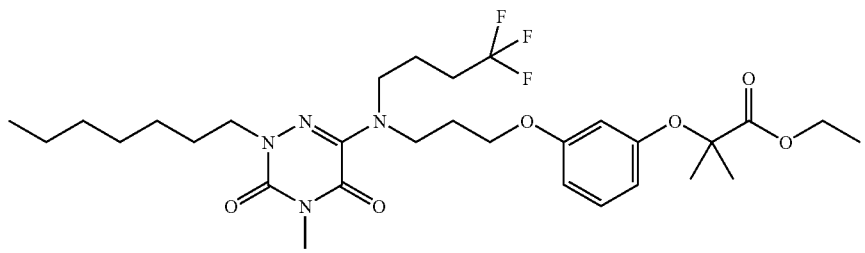

Compound 51 (oil) is prepared from triazine 9m and from intermediate 10b according to synthesis method 3 using Mitsunobu coupling conditions such as those described for example 33.

TLC silica gel 60 F 254 Merck, petroleum ether:AcOEt 90:10, Rf=0.56.

Example 52

Ethyl 2-(3-{3-[(2,4-Dimethyl-3,5-dioxo-2,3,4,5-tetrahydro-[1,2,4]triazin-6-yl)-heptyl-amino]-propoxy}-phenylsulfanyl)-2-methyl-propionate (52)

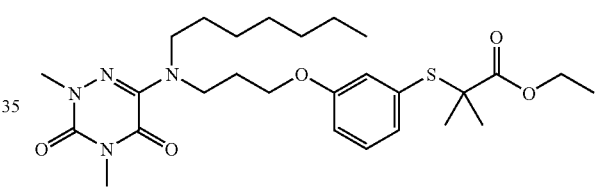

Compound 52 (oil) is prepared from triazine 9n and from intermediate 11c according to synthesis method 3 using coupling conditions such as those described for example 33.

TLC silica gel 60 F 254 Merck, heptane:AcOEt 70:30, Rf=0.22.

Example 53

Ethyl 2-(4-{3-[(2,4-Dimethyl-3,5-dioxo-2,3,4,5-tetrahydro-[1,2,4]triazin-6-yl)-heptyl-amino]-propoxy}-phenylsulfanyl)-2-methyl-propionate (53)

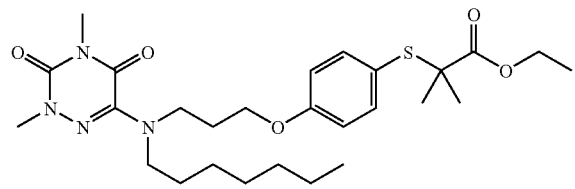

Compound 53 (oil) is prepared from triazine 9n and from intermediate 11d according to synthesis method 3 using coupling conditions such as those described for example 33.

TLC silica gel 60 F 254 Merck, heptane:AcOEt 80:20, Rf=0.45.

Example 54

Ethyl 2-(3-{4-[(2,4-Dimethyl-3,5-dioxo-2,3,4,5-tetrahydro-[1,2,4]triazin-6-yl)-heptyl-amino]-butoxy}-phenylsulfanyl)-2-methyl-propionate (54)

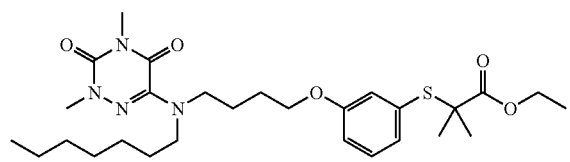

Compound 54 (oil) is prepared from triazine 9o and from intermediate 11c according to synthesis method 3 using coupling conditions such as those described for example 33.

TLC silica gel 60 F 254 Merck, heptane:AcOEt 70:30, Rf=0.25.

Example 55

Ethyl 2-(2-{2-[3,5-Dioxo-2,4-bis-(4,4,4-trifluoro-butyl)-2,3,4,5-tetrahydro-[1,2,4]triazin-6-ylamino]-ethyl}-phenoxy)-2-methyl-propionate (55)

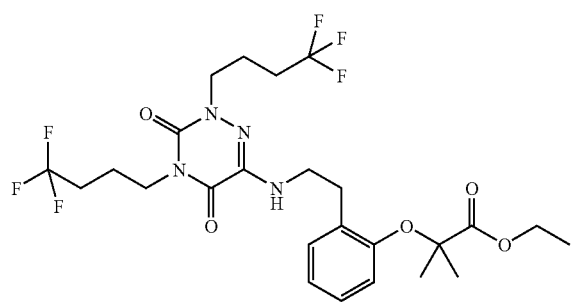

Compound 55 is prepared according to synthesis method 4: 6.6 g (16.1 mmol) of triazine 1d, 2 g (13.4 mmol) of 2 (2-methoxy-phenyl)-ethylamine and 4.7 ml (33.9 mmol) of triethylamine are placed in 20 ml of n-butanol at 120° C. for 28 h. After dry concentration of the reaction medium, the residue obtained is taken up in H₂O and extracted with AcOEt. The organic phases are dried on MgSO₄, then dry concentrated. The oil obtained is purified by flash chromatography on silica (petroleum ether:AcOEt 90:10). 3.1 g of intermediate are isolated in the form of an oil (yield=48%) which are then placed in 30 ml of CH₂Cl₂ at 0° C. under nitrogen. A solution of BBr₃ (12.8 ml at 1 M in CH₂Cl₂) is added dropwise and the reaction medium is stirred for 3.5 h at ambient temperature. It is then placed at 0° C. and acidified by a 0.1 N HCl solution until pH=1. The organic phase is decanted and then washed with 100 ml of water. After drying on MgSO₄, it is dry concentrated and the residue obtained is purified by flash chromatography on silica (CH₂Cl₂:AcOEt 95:5). 1.9 g of the corresponding phenol is isolated yield=65%) which is then placed in 2 ml of DMF in the presence of 1.9 ml (12.5 mmol) of ethyl bromoisobutyrate and 0.6 g (4.3 mmol) of K₂CO₃. The reaction medium is heated at 130° C. for 22 h then filtered and dry concentrated. The oil obtained is purified by flash chromatography on silica (CH₂Cl₂:AcOEt 98:2). 0.8 g of compound 55 (yield=34%) is isolated in the form of an oil.

TLC silica gel 60 F 254 Merck, CH₂Cl₂:AcOEt 95:5, Rf=0.66.

Example 56

Ethyl 2-methyl-2-(3-{2-[4-methyl-3,5-dioxo-2-(4,4,4-trifluoro-butyl)-2,3,4,5-tetrahydro-[1,2,4]triazin-6-ylamino]-ethyl}-phenoxy)-propionate (56)

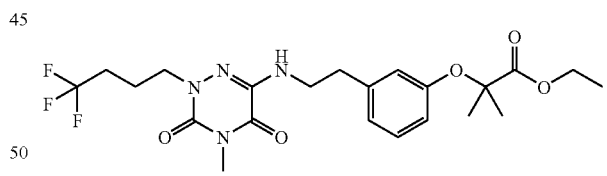

Compound 56 is prepared according to synthesis method 1: 1.1 g (4.4 mmol) of derivative 13b and 1 g (3.7 mmol) of triazine 4a are placed in 10 ml of nBuOH in the presence of 1.3 ml (9.3 mmol) of triethylamine. This mixture is stirred at 120° C. for 24 h. After dry concentration of the reaction medium, the residue obtained is taken up in H₂O and extracted with AcOEt. The organic phases are dried on MgSO₄, then dry concentrated. The oil obtained is purified by flash chromatography on silica (petroleum ether:AcOEt 90:10). 0.4 g of compound 56 is isolated in the form of an oil (yield=27%).

TLC silica gel 60 F 254 Merck, petroleum ether:AcOEt 80:20, Rf=0.19.

Example 57

Ethyl 2-{3-[2-(2-heptyl-4-methyl-3,5-dioxo-2,3,4,5-tetrahydro-[1,2,4]triazin-6-ylamino)-ethyl]-phenoxy}-2-methyl-propionate (57)

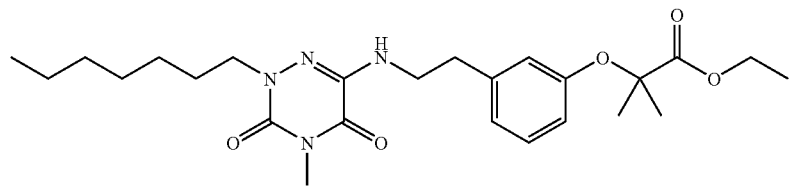

Compound 57 (oil) is prepared from triazine 4b and from intermediate 13b according to synthesis method 1.

TLC silica gel 60 F 254 Merck, petroleum ether:AcOEt 70:30, Rf=0.44.

Example 58

Ethyl 2-methyl-2-(3-{2-[2-methyl-3,5-dioxo-4-(4,4,4-trifluoro-butyl)-2,3,4,5-tetrahydro-[1,2,4]triazin-6-ylamino]-ethyl}-phenoxy)-propionate (58)

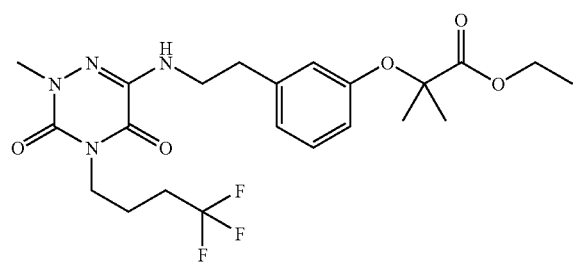

Compound 58 (oil) is prepared from triazine 6a and from intermediate 13b according to synthesis method 1.

TLC silica gel 60 F 254 Merck, petroleum ether:AcOEt 80:20, Rf=0.33.

Example 59

Ethyl 2-{3-[2-(4-heptyl-2-methyl-3,5-dioxo-2,3,4,5-tetrahydro-[1,2,4]triazin-6-ylamino)-ethyl]-phenoxy}-2-methyl-propionate (59)

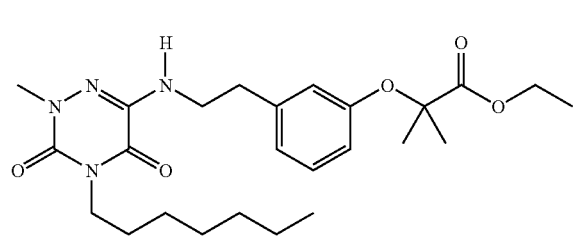

Compound 59 (oil) is prepared from triazine 7a and from intermediate 13b according to synthesis method 1.

TLC silica gel 60 F 254 Merck, petroleum ether:AcOEt 80:20, Rf=0.50.

Example 60

Ethyl 2-(3-{2-[4-heptyl-3,5-dioxo-2-(4,4,4-trifluoro-butyl)-2,3,4,5-tetrahydro-[1,2,4]triazin-6-ylamino]-ethyl}-phenoxy)-2-methyl-propionate (60)

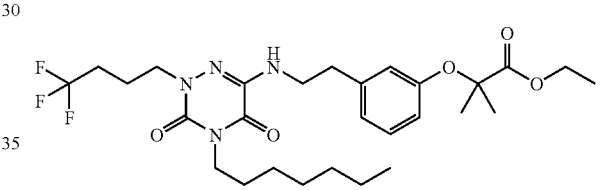

Compound 60 (oil) is prepared from triazine 7b and from intermediate 13b according to synthesis method 1.

TLC silica gel 60 F 254. Merck, petroleum ether:AcOEt 90:10, Rf=0.22.

Example 61

Ethyl 2-{3-[2-(4-heptyl-2-methyl-3,5-dioxo-2,3,4,5-tetrahydro-[1,2,4]triazin-6-ylamino)-ethyl]-phenylsulfanyl}-2-methyl-propionate (61)

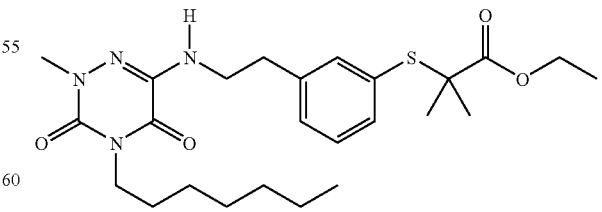

Compound 61 (oil) is prepared from triazine 7a and from intermediate 13d according to synthesis method 1.

TLC silica gel 60 F 254 Merck, petroleum ether:AcOEt 70:30, Rf=0.61.

Example 62

Ethyl 2-methyl-2-(3-{3-[4-methyl-3,5-dioxo-2-(4,4,4-trifluoro-butyl)-2,3,4,5-tetrahydro-[1,2,4]triazin-6-ylamino]-propyl}-phenoxy)-propionate (62)

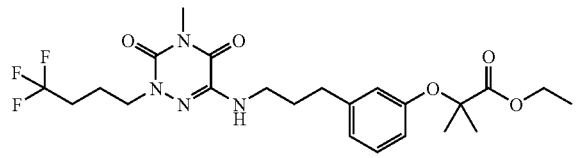

Compound 62 (oil) is prepared from triazine 4a and from intermediate 13j according to synthesis method 4.

TLC silica gel 60 F 254 Merck, CH$_2$Cl$_2$:AcOEt 90:10, Rf=0.60.

Example 63

Ethyl 2-(3-{3-[2-(2-cyano-ethyl)-4-methyl-3,5-dioxo-2,3,4,5-tetrahydro-[1,2,4]triazin-6-ylamino]-propyl}-phenoxy)-2-methyl-propionate (63)

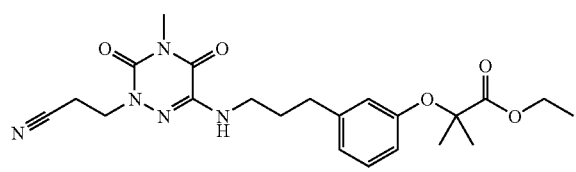

Compound 63 (oil) is prepared from triazine 3a and from intermediate 13j according to synthesis method 4.

TLC silica gel 60 F 254 Merck, petroleum ether:AcOEt 80:20, Rf=0.44.

Example 64

Ethyl 2-{3-[3-(2-heptyl-4-methyl-3,5-dioxo-2,3,4,5-tetrahydro-[1,2,4]triazin-6-ylamino)-propyl]-phenoxy}-2-methyl-propionate (64)

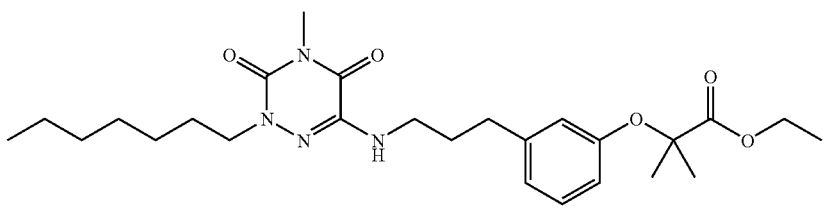

Compound 64 (oil) is prepared from triazine 4b and from intermediate 13j according to synthesis method 4.

TLC silica gel 60 F 254 Merck, petroleum ether:AcOEt 80:20, Rf=0.20.

Example 65

Ethyl 2-methyl-2-(3-{3-[2-methyl-3,5-dioxo-4-(4,4,4-trifluoro-butyl)-2,3,4,5-tetrahydro-[1,2,4]triazin-6-ylamino]-propyl}-phenoxy)-propionate (65).

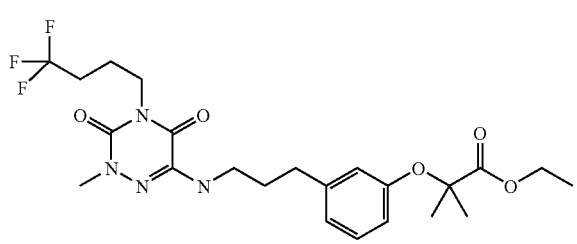

Compound 65 (oil) is prepared from triazine 6a and from intermediate 13j according to synthesis method 4.

TLC silica gel 60 F 254 Merck, CH$_2$Cl$_2$:AcOEt 90:10, Rf=0.78.

Example 66

Ethyl 2-(3-{3-[3,5-dioxo-2,4-bis-(4,4,4-trifluoro-butyl)-2,3,4,5-tetrahydro-[1,2,4]triazin-6-ylamino]-propyl}-phenoxy)-2-methyl-propionate (66)

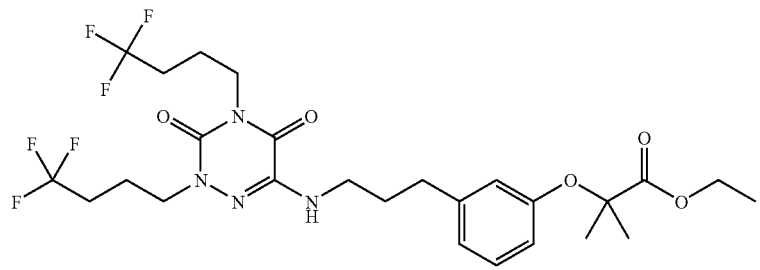

Compound 66 (oil) is prepared from triazine 1d and from intermediate 13l according to synthesis method 4.

TLC silica gel 60 F 254 Merck, petroleum ether:AcOEt 70:30, Rf=0.49.

Example 67

Ethyl 2-{3-[3-(4-heptyl-2-methyl-3,5-dioxo-2,3,4,5-tetrahydro-[1,2,4]triazin-6-ylamino)-propyl]-phenoxy}-2-methyl-propionate (67)

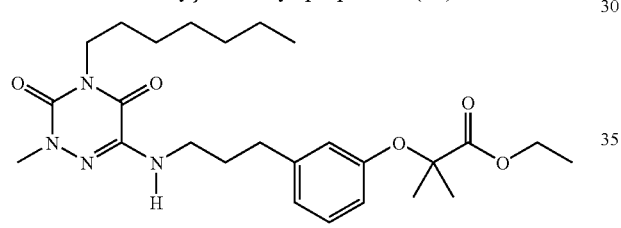

Compound 67 (oil) is prepared from triazine 7a and from intermediate 13c according to synthesis method 1.

TLC silica gel 60 F 254 Merck, petroleum ether:AcOEt 80:20, Rf=0.50.

Example 68

Ethyl 2-(3-{3-[4-heptyl-3,5-dioxo-2-(4,4,4-trifluoro-butyl)-2,3,4,5-tetrahydro-[1,2,4]triazin-6-ylamino]-propyl}-phenoxy)-2-methyl-propionate (68)

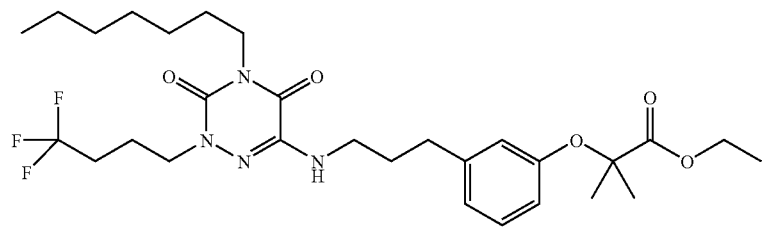

Compound 68 (oil) is prepared from triazine 7b and from intermediate 13j according to synthesis method 4.

TLC silica gel 60 F 254 Merck, petroleum ether:AcOEt 80:20, Rf=0.63.

Example 69

Ethyl 2-{3-[3-(2,4-diheptyl-3,5-dioxo-2,3,4,5-tetrahydro-[1,2,4]triazin-6-ylamino)-propyl]-phenoxy}-2-methyl-propionate (69)

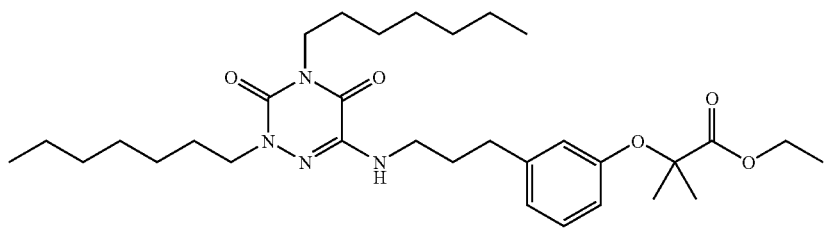

Compound 69 (oil) is prepared from triazine 1e and from intermediate 13j according to synthesis method 4.
TLC silica gel 60 F 254 Merck, petroleum ether:AcOEt 80:20, Rf=0.53.

Example 70

Ethyl 2-{3-[3-(2-benzyl-4-heptyl-3,5-dioxo-2,3,4,5-tetrahydro-[1,2,4]triazin-6-ylamino)-propyl]-phenoxy}-2-methyl-propionate (70)

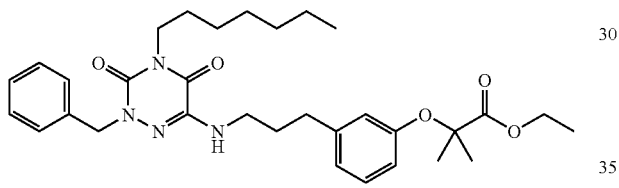

Compound 70 (oil) is prepared from triazine 7c and from intermediate 13j according to synthesis method 4.
TLC silica gel 60 F 254 Merck, petroleum ether:AcOEt 80:20, Rf=0.47.

Example 71

Ethyl 2-(3-{3-[4-benzyl-3,5-dioxo-2-(4,4,4-trifluoro-butyl)-2,3,4,5-tetrahydro-[1,2,4]triazin-6-ylamino]-propyl}-phenoxy)-2-methyl-propionate (71)

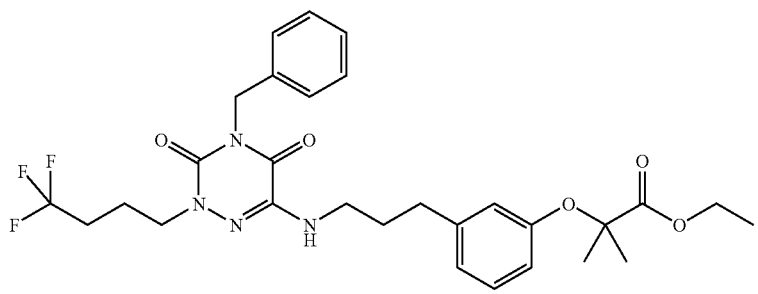

Compound 71 (oil) is prepared from triazine 8a and from intermediate 13j according to synthesis method 4.
TLC silica gel 60 F 254 Merck, petroleum ether:AcOEt 80:20, Rf=0.30.

Example 72

Ethyl 2-{3-[3-(4-Benzyl-2-heptyl-3,5-dioxo-2,3,4,5-tetrahydro-[1,2,4]triazin-6-ylamino)-propyl]-phenoxy}-2-methyl-propionate (72)

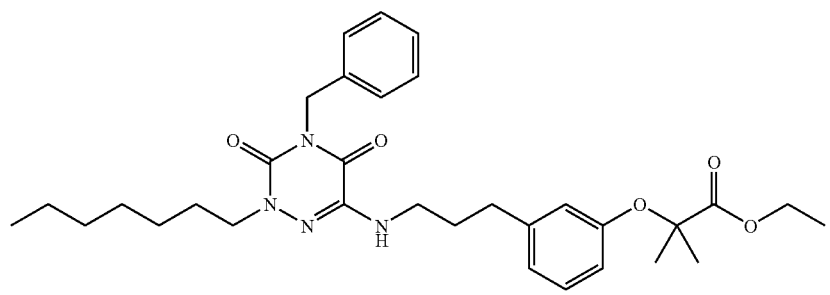

Compound 72 (oil) is prepared from triazine 8b and from intermediate 13j according to synthesis method 4.
TLC silica gel 60 F 254 Merck, petroleum ether:AcOEt 80:20, Rf=0.42.

Example 73

Ethyl 2-{4-[3-(4-heptyl-2-methyl-3,5-dioxo-2,3,4,5-tetrahydro-[1,2,4]triazin-6-ylamino)-propyl]-phenylsulfanyl}-2-methyl-propionate (73)

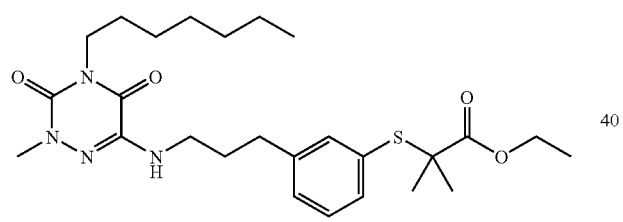

Compound 73 (oil) is prepared from triazine 7a and from intermediate 13e according to synthesis method 1.
TLC silica gel 60 F 254 Merck, petroleum ether:AcOEt 80:20, Rf=0.58.

Example 74

Ethyl 2-methyl-2-(3-{4-[4-methyl-3,5-dioxo-2-(4,4,4-trifluoro-butyl)-2,3,4,5-tetrahydro-[1,2,4]triazin-6-ylamino]-butyl}-phenoxy)-propionate (74)

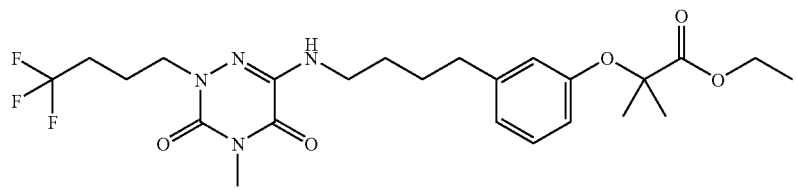

Compound 74 (oil) is prepared from triazine 4a and from intermediate 13m according to synthesis method 4.

TLC silica gel 60 F 254 Merck, petroleum ether:AcOEt 80:20, Rf=0.21.

Example 75

Ethyl 2-{3-[4-(2-heptyl-4-methyl-3,5-dioxo-2,3,4,5-tetrahydro-[1,2,4]triazin-6-ylamino)-butyl]-phenoxy}-2-methyl-propionate (75)

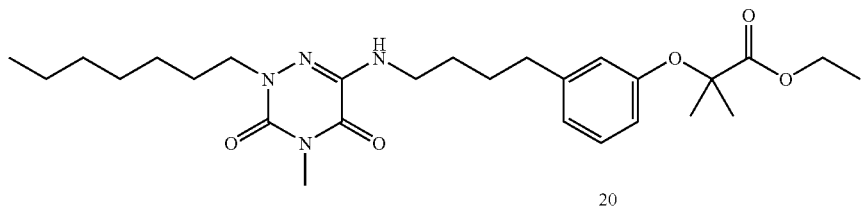

Compound 75 (oil) is prepared from triazine 4b and from intermediate 13m according to synthesis method 4.

TLC silica gel 60 F 254 Merck, petroleum ether:AcOEt 80:20, Rf=0.44.

Example 76

Ethyl 2-methyl-2-(3-{4-[4-(3-methyl-but-2-enyl)-3,5-dioxo-2-(4,4,4-trifluoro-butyl)-2,3,4,5-tetrahydro-[1,2,4]triazin-6-ylamino]-butyl}-phenoxy)-propionate (76)

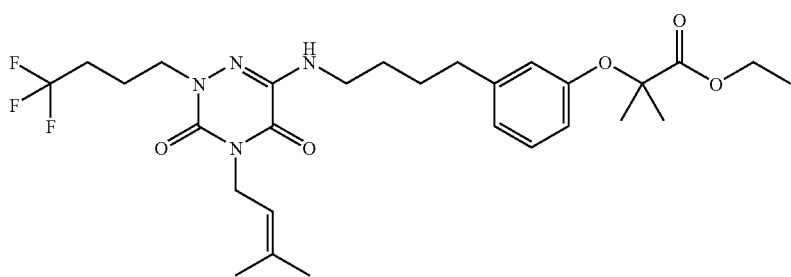

Compound 76 (oil) is prepared from triazine 5d and from intermediate 13m according to synthesis method 4.

TLC silica gel 60 F 254 Merck, petroleum ether:AcOEt 80:20, Rf=0.50.

Example 77

Ethyl 2-methyl-2-(3-{4-[2-methyl-3,5-dioxo-4-(4,4,4-trifluoro-butyl)-2,3,4,5-tetrahydro-[1,2,4]triazin-6-ylamino]-butyl}-phenoxy)-propionate (77)

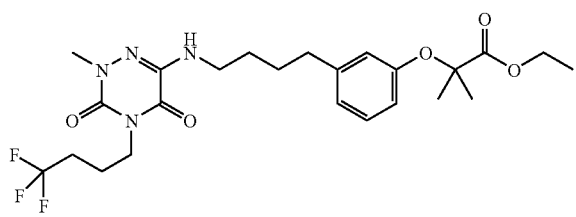

Compound 77 (oil) is prepared from triazine 6a and from intermediate 13k according to synthesis method 4.

TLC silica gel 60 F 254 Merck, petroleum ether:AcOEt 80:20, Rf=0.35.

Example 78

Tert-butyl 2-methyl-2-(3-{4-[2-methyl-3,5-dioxo-4-(4,4,4-trifluoro-butyl)-2,3,4,5-tetrahydro-[1,2,4]triazin-6-ylamino]-butyl}-phenoxy)-propionate (78)

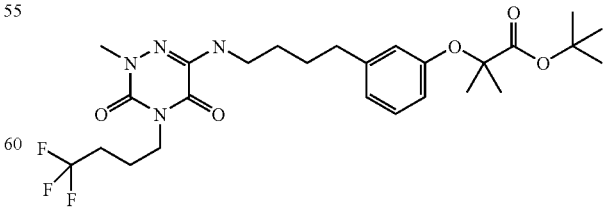

Compound 78 (oil) is prepared from triazine 6a and from intermediate 13m according to synthesis method 4 using tert-butyl bromoisobutyrate in the last step.

TLC silica gel 60 F 254 Merck, heptane:AcOEt 60:40, Rf=0.35.

Example 79

2-Methyl-2-(3-{4-[2-methyl-3,5-dioxo-4-(4,4,4-trifluoro-butyl)-2,3,4,5-tetrahydro-[1,2,4]triazin-6-ylamino]-butyl}-phenoxy)-propionic Acid (79)

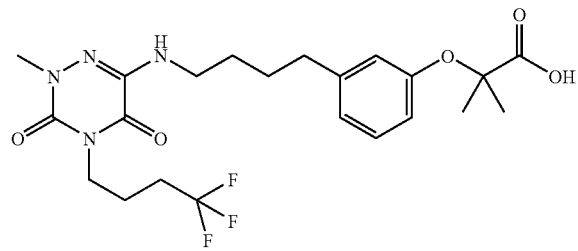

After the hydrolysis of compound 78 (trifluoroacetic acid/CH$_2$Cl$_2$, yield=61%), compound 79 is isolated in the form of a solid.

TLC silica gel 60 F 254 Merck, CH$_2$Cl$_2$:MeOH 90:10, Rf=0.73. F=116° C.

Example 80

Ethyl 2-(3-{4-[3,5-dioxo-2,4-bis-(4,4,4-trifluoro-butyl)-2,3,4,5-tetrahydro-[1,2,4]triazin-6-ylamino]-butyl}-phenoxy)-2-methyl-propionate (80)

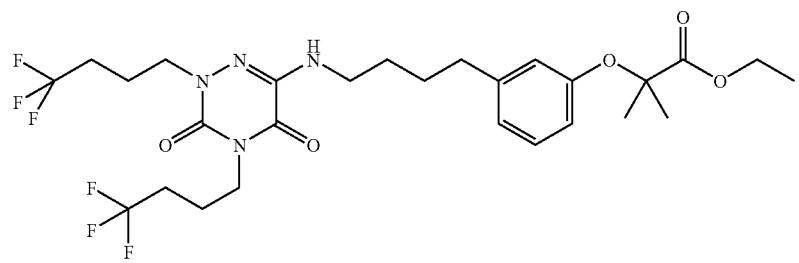

Compound 80 (oil) is prepared from triazine 1d and from intermediate 13m according to synthesis method 4.
TLC silica gel 60 F 254 Merck, petroleum ether:AcOEt 80:20, Rf=0.32.

Example 81

Ethyl 2-(3-{4-[2-(2-cyano-ethyl)-3,5-dioxo-4-(4,4,4-trifluoro-butyl)-2,3,4,5-tetrahydro-[1,2,4]triazin-6-ylamino]-butyl}-phenoxy)-2-methyl-propionate (81)

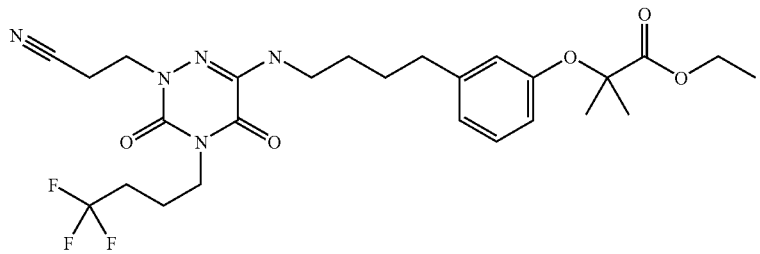

Compound 81 (oil) is prepared from triazine 3b and from intermediate 13k according to synthesis method 4.

TLC silica gel 60 F 254 Merck, petroleum ether:AcOEt 70:30, Rf=0.20.

Example 82

Ethyl 2-(3-{4-[2-heptyl-3,5-dioxo-4-(4,4,4-trifluoro-butyl)-2,3,4,5-tetrahydro-[1,2,4]triazin-6-ylamino]-butyl}-phenoxy)-2-methyl-propionate (82)

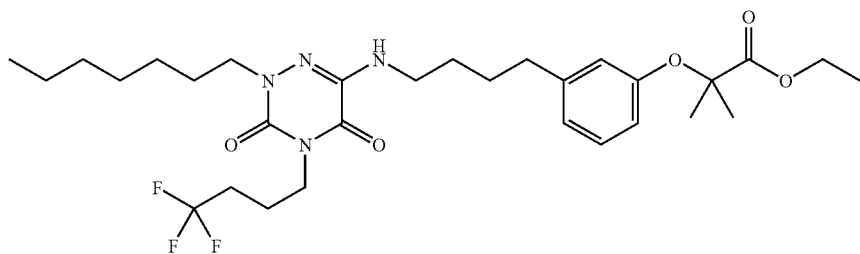

Compound 82 (oil) is prepared from triazine 6b and from intermediate 13k according to synthesis method 4.

TLC silica gel 60 F 254 Merck, petroleum ether:AcOEt 80:20, Rf=0.37.

Example 83

Tert-butyl 2-(3-{4-[2-heptyl-3,5-dioxo-4-(4,4,4-trifluoro-butyl)-2,3,4,5-tetrahydro-[1,2,4]triazin-6-ylamino]-butyl}-phenoxy)-2-methyl-propionate (83)

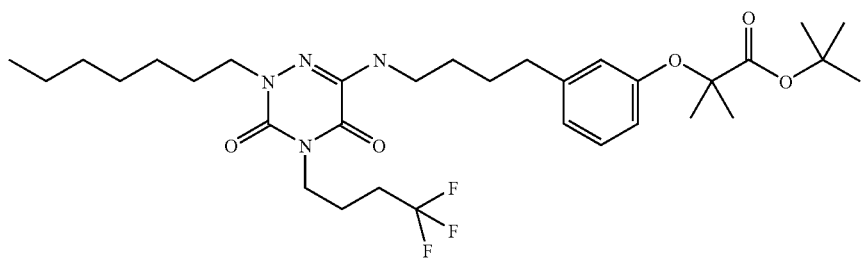

Compound 83 (oil) is prepared from triazine 6b and from intermediate 13m according to synthesis method 4 using tert-butyl bromoisobutyrate in the last step.

TLC silica gel 60 F 254 Merck, heptane:AcOEt 60:40, Rf=0.43.

Example 84

2-(3-{4-[2-Heptyl-3,5-dioxo-4-(4,4,4-trifluoro-butyl)-2,3,4,5-tetrahydro-[1,2,4]triazin-6-ylamino]-butyl}-phenoxy)-2-methyl-propionic Acid (84)

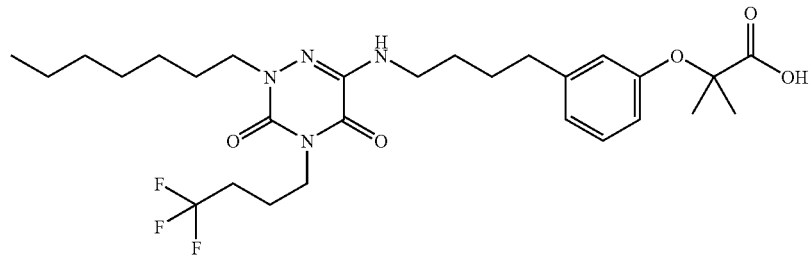

After the hydrolysis of compound 83 (trifluoroacetic acid/CH$_2$Cl$_2$, yield=76%), compound 84 is isolated in the form of an oil.

TLC silica gel 60 F 254 Merck, CH$_2$Cl$_2$:MeOH 95:5, Rf=0.39.

Example 85

Ethyl 2-(3-{4-[4-heptyl-3,5-dioxo-2-(4,4,4-trifluoro-butyl)-2,3,4,5-tetrahydro-[1,2,4]triazin-6-ylamino]-butyl}-phenoxy)-2-methyl-propionate (85)

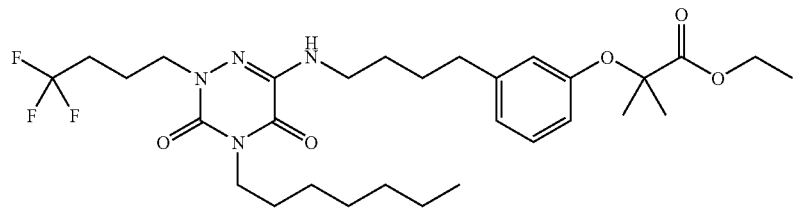

Compound 85 (oil) is prepared from triazine 7b and from intermediate 13m according to synthesis method 4.

TLC silica gel 60 F 254 Merck, petroleum ether:AcOEt 80:20, Rf=0.75.

Example 86

Ethyl 2-(3-{4-[2-(2-cyano-ethyl)-4-heptyl-3,5-dioxo-2,3,4,5-tetrahydro-[1,2,4]triazin-6-ylamino]-butyl}-phenoxy)-2-methyl-propionate (86)

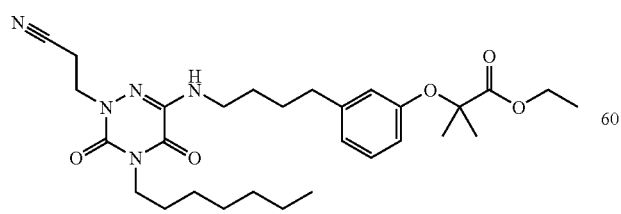

Compound 86 (oil) is prepared from triazine 3c and from intermediate 13m according to synthesis method 4.

TLC silica gel 60 F 254. Merck, petroleum ether:AcOEt 70:30, Rf=0.51.

Example 87

Ethyl 4-(6-{4-[3-(1-ethoxycarbonyl-1-methyl-ethoxy)-phenyl]-butylamino}-4-heptyl-3,5-dioxo-4,5-dihydro-3H-[1,2,4]triazin-2-yl)-but-2-enonate (87)

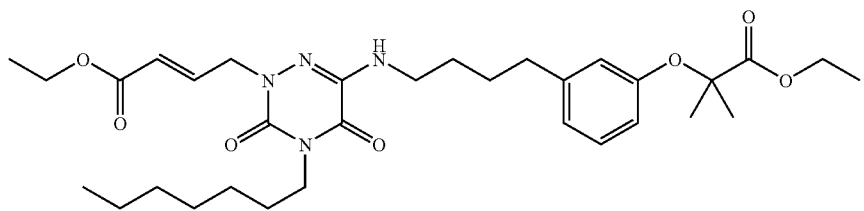

Compound 87 (oil) is prepared according to synthesis method 6: 0.2 g (5 mmol) of NaH (60% in paraffin) is placed in suspension in 10 ml of DMF at 0° C. under nitrogen. 1.4 g (2.6 mmol) of compound 86 diluted in 4 ml of DMF is added dropwise. The mixture is stirred for 4.5 h at ambient temperature then dry concentrated. The residue is taken up in H₂O and extracted with AcOEt. The organic phases are dried on MgSO₄, then dry concentrated. The oil obtained is purified by flash chromatography on silica (CH₂Cl₂:AcOEt 90:10) and 0.8 g of solid is isolated (yield=63%). 78 mg (1.9 mmol) of NaH (60% in paraffin) is placed in suspension in 15 ml of DMF at 0° C. under nitrogen. The solid previously isolated (0.8 g, 1.6 mmol) diluted in 5 ml of DMF is added dropwise then this mixture is stirred for 1 h at ambient temperature.

0.29 ml (2.1 mmol) of ethyl 4-bromo-but-2-enoate is added and then stirring is continued for 9 h. After dry concentration, the residue obtained is taken up in H₂O and extracted with AcOEt. The organic phases are dried on MgSO₄, then dry concentrated. The oil obtained is purified by flash chromatography on silica (petroleum ether:AcOEt 80:20). 0.6 g of compound 87 is isolated in the form of an oil (yield=56%).

TLC silica gel 60 F 254 Merck, petroleum ether:AcOEt 80:20, Rf=0.33.

Example 88

Ethyl 2-{3-[4-(2,4-diheptyl-3,5-dioxo-2,3,4,5-tetrahydro-[1,2,4]triazin-6-ylamino)-butyl]-phenoxy}-2-methyl-propionate (88)

Compound 88 (oil) is prepared from triazine 1e and from intermediate 13k according to synthesis method 4.

TLC silica gel 60 F 254 Merck, petroleum ether:AcOEt 80:20, Rf=0.53.

Example 89

Ethyl 2-{3-[4-(2-benzyl-4-heptyl-3,5-dioxo-2,3,4,5-tetrahydro-[1,2,4]triazin-6-ylamino)-butyl]-phenoxy}-2-methyl-propionate (89)

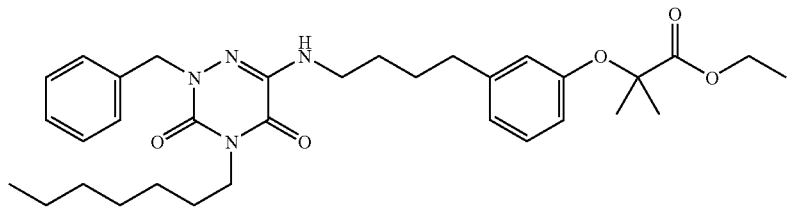

Compound 89 (solid) is prepared from triazine 7c and from intermediate 13k according to synthesis method 4.

TLC silica gel 60 F 254 Merck, petroleum ether:AcOEt 80:20, Rf=0.37. F=58° C.

Example 90

Ethyl 2-(3-{3-[4-benzyl-3,5-dioxo-2-(4,4,4-trifluoro-butyl)-2,3,4,5-tetrahydro-[1,2,4]triazin-6-ylamino]-butyl}-phenoxy)-2-methyl-propionate (90)

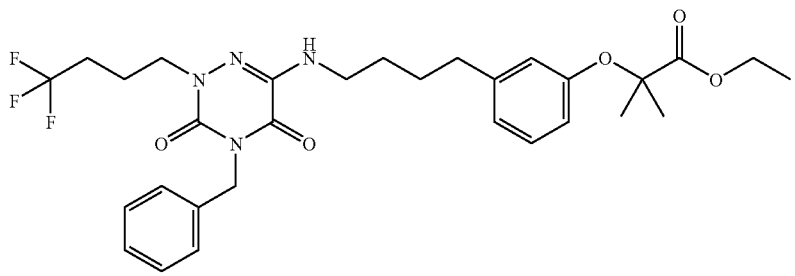

Compound 90 (oil) is prepared from triazine 8a and from intermediate 13k according to synthesis method 4.

TLC silica gel 60 F 254 Merck, petroleum ether:AcOEt 80:20, Rf=0.46.

Example 91

Ethyl 2-{3-[4-(4-benzyl-2-heptyl-3,5-dioxo-2,3,4,5-tetrahydro-[1,2,4]triazin-6-ylamino)-butyl]-phenoxy}-2-methyl-propionate (91)

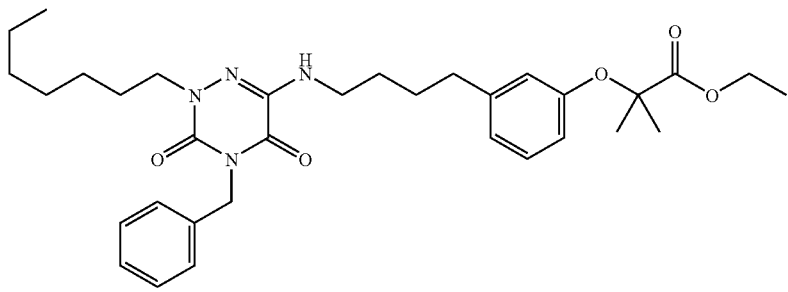

Compound 91 (oil) is prepared from triazine 8b and from intermediate 13k according to synthesis method 4.

TLC silica gel 60 F 254 Merck, petroleum ether:AcOEt 80:20, Rf=0.60.

Example 92

Ethyl 2-(3-{5-[3,5-dioxo-2,4-bis-(4,4,4-trifluoro-butyl)-2,3,4,5-tetrahydro-[1,2,4]triazin-6-ylamino]-pentyl}-phenoxy)-2-methyl-propionate (92)

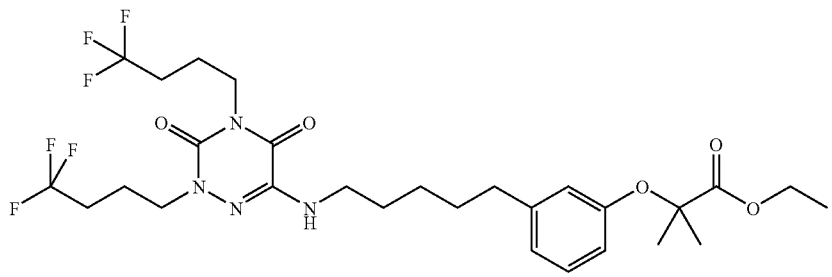

Compound 92 (oil) is prepared from triazine 1d and from intermediate 13n according to synthesis method 4.

TLC silica gel 60 F 254 Merck, petroleum ether:AcOEt 80:20, Rf=0.45.

Example 93

Ethyl 2-methyl-2-(3-{4-[4-methyl-3,5-dioxo-2-(4,4,4-trifluoro-butyl)-2,3,4,5-tetrahydro-[1,2,4]triazin-6-ylamino]-butyl}-phenylsulfanyl)-propionate (93)

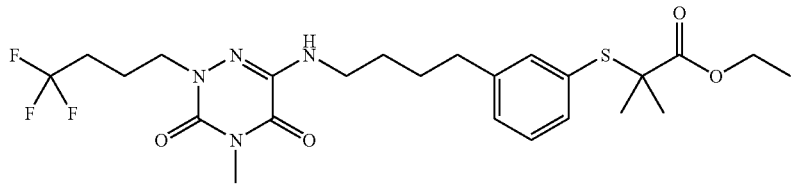

Compound 93 (oil) is prepared from triazine 4a and from intermediate 13f according to synthesis method 1.

TLC silica gel 60 F 254 Merck, petroleum ether:AcOEt 80:20; Rf=0.45.

Example 94

Ethyl 2-{3-[4-(2-heptyl-4-methyl-3,5-dioxo-2,3,4,5-tetrahydro-[1,2,4]triazin-6-ylamino)-butyl]-phenyl-sulfanyl}-2-methyl-propionate (94)

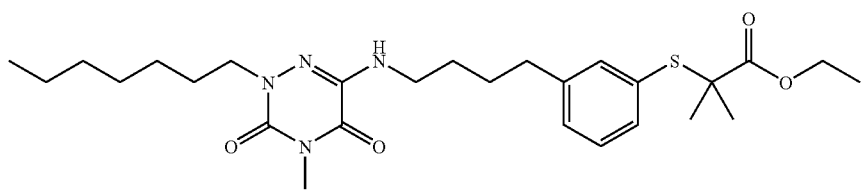

Compound 94 (oil) is prepared from triazine 4b and from intermediate 13f according to synthesis method 1.

TLC silica gel 60 F 254 Merck, petroleum ether:AcOEt 80:20, Rf=0.26.

Example 95

Ethyl 2-methyl-2-(3-{4-[2-methyl-3,5-dioxo-4-(4,4,4-trifluoro-butyl)-2,3,4,5-tetrahydro-[1,2,4]triazin-6-ylamino]-butyl)}-phenylsulfanyl)-propionate (95)

Compound 95 (oil) is prepared from triazine 6a and from intermediate 13f according to synthesis method 1.

TLC silica gel 60 F 2.54 Merck, petroleum ether:AcOEt 80:20, Rf=0.34.

Example 96

2-Methyl-2-(3-{4-[2-methyl-3,5-dioxo-4-(4,4,4-trifluoro-butyl)-2,3,4,5-tetrahydro-[1,2,4]triazin-6-ylamino]-butyl}-phenylsulfanyl)-propionic Acid (96)

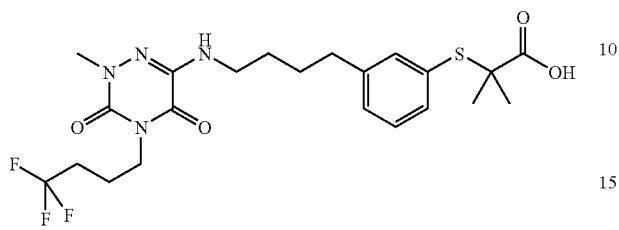

After the hydrolysis of compound 95 (BBr$_3$/CH$_2$Cl$_2$, yield=49%), compound 96 is isolated in the form of a solid.
TLC silica gel 60 F 254 Merck, CH$_2$Cl$_2$:AcOEt 80:20, Rf=0.24. F=106° C.

Example 97

Ethyl 2-(3-{4-[4-heptyl-3,5-dioxo-2-(4,4,4-trifluoro-butyl)-2,3,4,5-tetrahydro-[1,2,4]triazin-6-ylamino]-butyl}-phenylsulfanyl)-2-methyl-propionate (97)

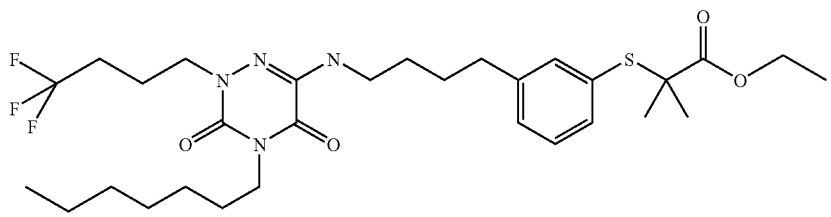

Compound 97 (oil) is prepared from triazine 7b and from intermediate 13f according to synthesis method 1.
TLC silica gel 60 F 254 Merck, petroleum ether:AcOEt 80:20, Rf=0.74.

Example 98

Ethyl 2-{3-[4-(2,4-diheptyl-3,5-dioxo-2,3,4,5-tetrahydro-[1,2,4]triazin-6-ylamino)-butyl]-phenylsulfanyl}-2-methyl-propionate (98)

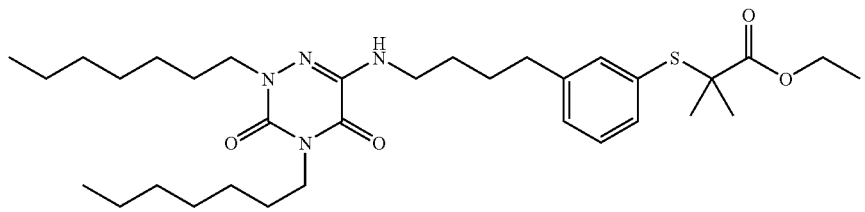

Compound 98 (oil) is prepared from triazine 1e and from intermediate 13f according to synthesis method 1.
TLC silica gel 60 F 254 Merck, petroleum ether:AcOEt 80:20, Rf=0.53.

Example 99

Ethyl 2-{3-[4-(2-benzyl-4-heptyl-3,5-dioxo-2,3,4,5-tetrahydro-[1,2,4]triazin-6-ylamino)-butyl]-phenyl-sulfanyl}-2-methyl-propionate (99)

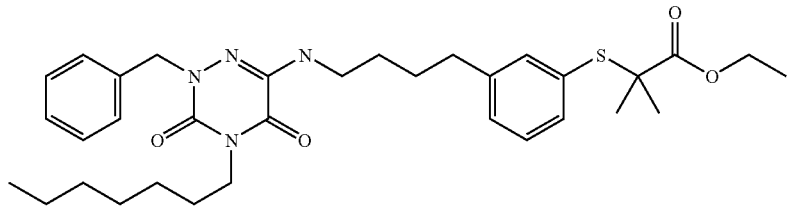

Compound 99 (oil) is prepared from triazine 7c and from intermediate 13f according to synthesis method 1.

TLC silica gel 60 F 254 Merck, petroleum ether:AcOEt 80:20, Rf=0.43.

Example 100

Ethyl 2-(3-{4-[4-Benzyl-3,5-dioxo-2-(4,4,4-trifluoro-butyl)-2,3,4,5-tetrahydro-[1,2,4]triazin-6-ylamino]-butyl}-phenylsulfanyl)-2-methyl-propionate (100)

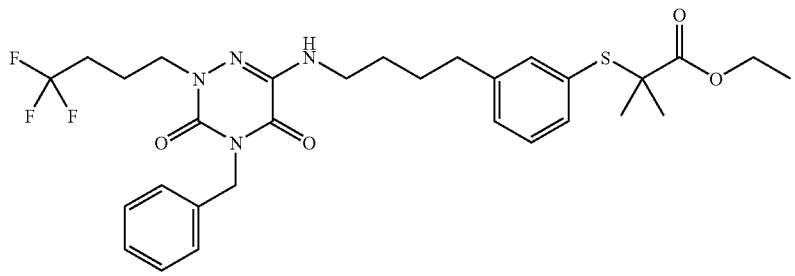

Compound 100 (oil) is prepared from triazine 8a and from intermediate 13f according to synthesis method 1.

TLC silica gel 60 F 254 Merck, petroleum ether:AcOEt 80:20, Rf=0.27.

Example 101

Ethyl 2-{3-[4-(4-benzyl-2-heptyl-3,5-dioxo-2,3,4,5-tetrahydro-[1,2,4]triazin-6-ylamino)-butyl]-phenyl-sulfanyl}-2-methyl-propionate (101)

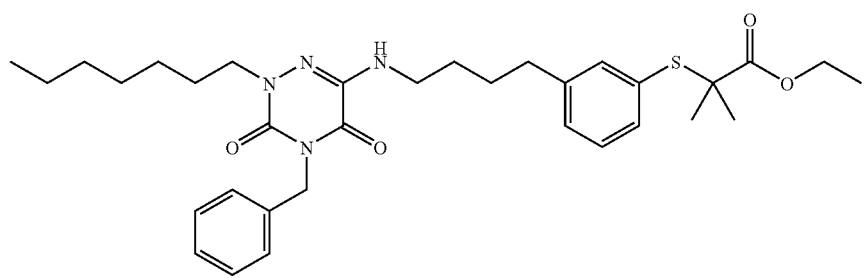

Compound 101 (oil) is prepared from triazine 8b and from intermediate 13f according to synthesis method 1.

TLC silica gel 60 F 254 Merck, petroleum ether:AcOEt 80:20, Rf=0.39.

Example 102

Ethyl 2-methyl-2-(4-{2-[4-methyl-3,5-dioxo-2-(4,4,4-trifluoro-butyl)-2,3,4,5-tetrahydro-[1,2,4]triazin-6-ylamino]-ethyl}-phenoxy)-propionate (102)

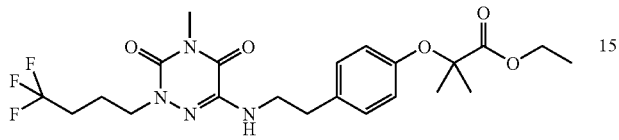

Compound 102 (oil) is prepared from triazine 4a and from intermediate 13a according to synthesis method 1.

TLC silica gel 60 F 254 Merck, petroleum ether:AcOEt 80:20, Rf=0.22.

Example 103

Ethyl 2-{4-[2-(2-heptyl-4-methyl-3,5-dioxo-2,3,4,5-tetrahydro-[1,2,4]triazin-6-ylamino)-ethyl]-phenoxy}-2-methyl-propionate (103)

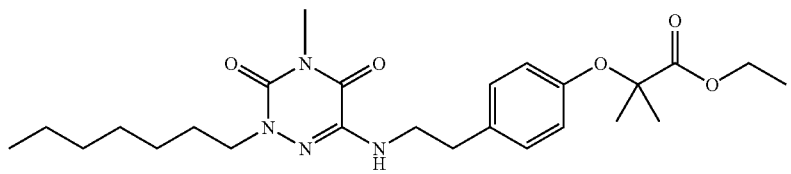

Compound 103 (oil) is prepared from triazine 4b and from intermediate 13a according to synthesis method 1.

TLC silica gel 60 F 254 Merck, $CH_2Cl_2$:AcOEt 90:10, Rf=0.54.

Example 104

Ethyl 4-[6-{2-[4-(1-ethoxycarbonyl-1-methyl-ethoxy)-phenyl]-ethylamino}-3,5-dioxo-4-(4,4,4-trifluoro-butyl)-4,5-dihydro-3H-[1,2,4]triazin-2-yl]-but-2-enoate (104)

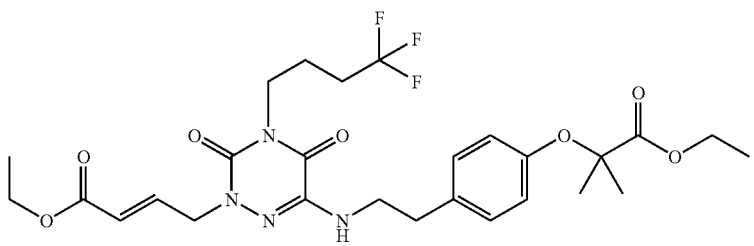

Compound 104 (oil) is prepared from triazine 3b and from intermediate 13a according to synthesis method 6 with ethyl 4-bromo-but-2-enoate used in the alkylation step.

TLC silica gel 60 F 254 Merck, petroleum ether:AcOEt 80:20, Rf=0.34.

Example 105

Ethyl 2-(4-{2-[2-(3-cyclohexyl-propyl)-3,5-dioxo-4-(4,4,4-trifluoro-butyl)-2,3,4,5-tetrahydro-[1,2,4]triazin-6-ylamino]-ethyl}-phenoxy)-2-methyl-propionate (105)

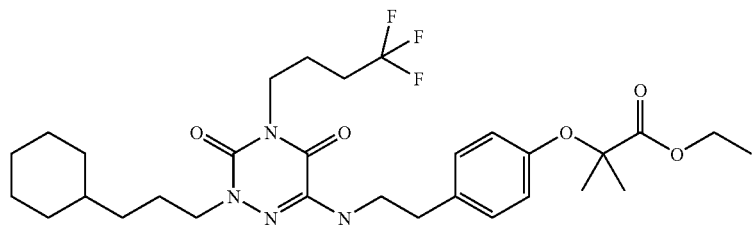

Compound 105 (oil) is prepared from triazine 6c and from intermediate 13a according to synthesis method 1.

TLC silica gel 60 F 254 Merck, petroleum ether:AcOEt 80:20, Rf=0.44.

Example 106

Ethyl 2-{4-[2-(4-heptyl-2-methyl-3,5-dioxo-2,3,4,5-tetrahydro-[1,2,4]triazin-6-ylamino)-ethyl]-phenoxy}-2-methyl-propionate (106)

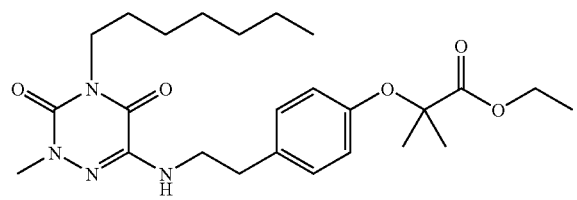

Compound 106 (solid) is prepared from triazine 7a and from intermediate 13a according to synthesis method 1.

TLC silica gel 60 F 254 Merck, petroleum ether:AcOEt 70:30, Rf=0.60. F=54° C.

Example 107

Ethyl 2-(4-{2-[4-heptyl-3,5-dioxo-2-(4,4,4-trifluoro-butyl)-2,3,4,5-tetrahydro-[1,2,4]triazin-6-ylamino]-ethyl}-phenoxy)-2-methyl-propionate (107)

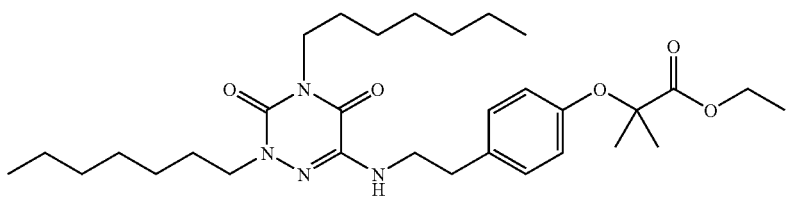

Compound 107 (solid) is prepared from triazine 7b and from intermediate 13a according to synthesis method 1.

TLC silica gel 60 F 254 Merck, petroleum ether:AcOEt 80:20, Rf=0.47. F=63° C.

Example 108

Ethyl 2-{4-[2-(2,4-diheptyl-3,5-dioxo-2,3,4,5-tetrahydro-[1,2,4]triazin-6-ylamino)-ethyl]-phenoxy}-2-methyl-propionate (108)

Compound 108 (oil) is prepared from triazine 1e and from intermediate 13a according to synthesis method 1.

TLC silica gel 60 F 254 Merck, petroleum ether:AcOEt 80:20, Rf=0.57.

Example 109

Ethyl 2-{4-[2-(4 benzyl-2-heptyl-3,5-dioxo-2,3,4,5-tetrahydro-[1,2,4]triazin-6-ylamino)-ethyl]-phenoxy}-2-methyl-propionate (109)

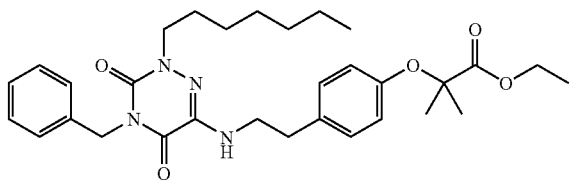

Compound 109 (solid) is prepared from triazine 8b and from intermediate 13a according to synthesis method 1.

TLC silica gel 60 F 254 Merck, petroleum ether:AcOEt 80:20, Rf=0.60. F=65° C.

Example 110

Ethyl 2-{4-[2-(2,4-bis-benzyloxymethyl-3,5-dioxo-2,3,4,5-tetrahydro-[1,2,4]triazin-6-ylamino)ethyl]-phenoxy}-2-methyl-propionate (110)

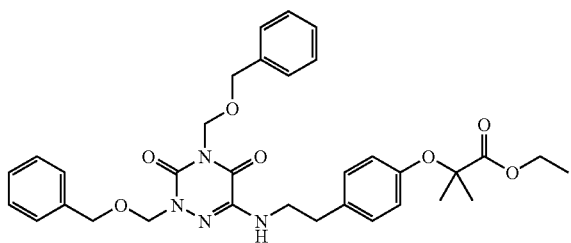

Compound 110 (oil) is prepared from triazine 1g and from intermediate-13a according to synthesis method 1.

TLC silica gel 60 F 254 Merck, petroleum ether:AcOEt 80:20, Rf=0.34.

Example 111

Ethyl 2-(4-{2-[(2,4-dimethyl-3,5-dioxo-2,3,4,5-tetrahydro-[1,2,4]triazin-6-yl)-(4,4,4-trifluoro-butyl)-amino]-ethyl}-phenoxy)-2-methyl-propionate (111)

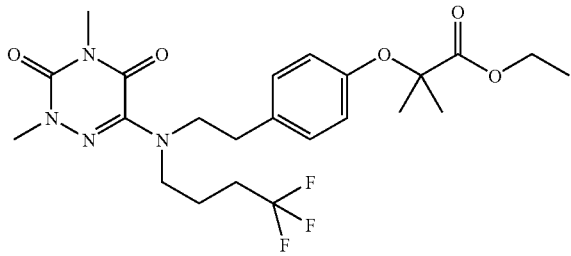

Compound 111 is prepared according to synthesis method 5: 3.2 g (14.7 mmol) of triazine 1b and 5.4 ml (36.8 mmol) of 2-(4-methoxy-phenyl)-ethylamine are placed in 30 ml of nBuOH in the presence of 5.1 ml (36.8 mmol) of triethylamine at 130° C. for 10.5 h. After dry concentration, the residue obtained is taken up in H$_2$O and extracted with AcOEt. The organic phases are dried on MgSO$_4$, then dry concentrated. The oil obtained is purified by flash chromatography on silica (heptane:AcOEt 50:50) and 2.3 g of solid is isolated (yield=54%). 0.48 g (12 mmol) of NaH (60% in paraffin) is placed in suspension in 15 ml of DMF at 0° C. under nitrogen. 2.3 g (7.9 mmol) of the previously isolated solid diluted in 5 ml of DMF are added dropwise. The mixture is stirred for 0.5 h at ambient temperature and then 4.7 g (19.8 mmol) of 1,1,1-trifluoro-4-iodo-butane are added and stirring is continued for 6.5 h. After dry concentration, the residue obtained is taken up in H$_2$O and extracted with AcOEt. The organic phases are dried on MgSO$_4$, then dry concentrated. The oil obtained is purified by flash chromatography on silica (CH$_2$Cl$_2$:AcOEt 95:5) and 0.82 g of oil is isolated (yield=26%). 0.4 g of the latter is then placed in 15 ml of CH$_2$Cl$_2$ at −60° C. under nitrogen, a BBr$_3$ solution (1 M in CH$_2$Cl) (0.24 ml diluted in 2 ml of CH$_2$Cl$_2$) is added dropwise and the reaction medium is stirred for 2 h at ambient temperature It is next placed at 0° C. and neutralized by a 1 N HCl solution. The organic phase is decanted and then washed with 100 ml of water. After drying on MgSO$_4$, it is dry concentrated and 0.38 g of the corresponding phenol is isolated (quantitative yield). It is then placed in 0.5 ml of ethyl bromoisobutyrate in the presence of 0.14 g (1 mmol) of K$_2$CO$_3$ at 150° C. for 5 h. After filtration and dry concentration, the residue obtained is purified by flash chromatography on silica (CH$_2$Cl$_2$:AcOEt 95:5) and 0.25 g of compound 111 is isolated in the form of an oil (yield=51%).

TLC silica gel 60 F 254 Merck, CH$_2$Cl$_2$:AcOEt 90:10, Rf=0.65.

Example 112

Ethyl 2-(4-{2-[(2,4-dimethyl-3,5-dioxo-2,3,4,5-tetrahydro-[1,2,4]triazin-6-yl)-heptyl-amino]-ethyl}-phenoxy)-2-methyl-propionate (112)

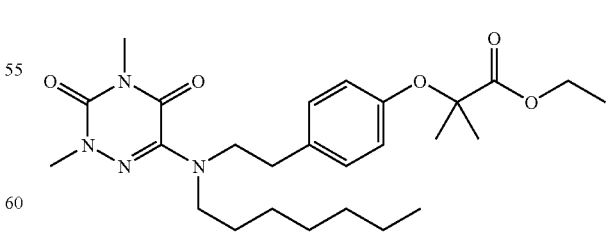

Compound 112 (oil) is prepared from triazine 1b and from intermediate 14a according to synthesis method 1.

TLC silica gel 60 F 254 Merck, CH$_2$Cl$_2$:AcOEt 70:30, Rf=0.70.

Example 113

2-(4-{2-[(2,4-Dimethyl-3,5-dioxo-2,3,4,5-tetrahydro-[1,2,4]triazin-6-yl)-heptyl-amino]-ethyl}-phenoxy)-2-methyl-propionic Acid (113)

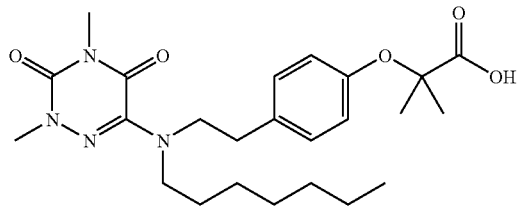

Compound 113 is prepared from triazine 1b and from 2-(4-methoxy-phenyl)-ethylamine according to synthesis method 5 by alkylating nitrogen with 1-bromoheptane and by using tert-butyl bromoisobutyrate. After hydrolysis with trifluoroacetic acid in $CH_2Cl_2$, compound 113 is isolated in the form of oil.

TLC silica gel 60 F 254 Merck, $CH_2Cl_2$:MeOH 90:10, Rf=0.43.

Example 114

Ethyl 2-(4-{2-[(2,4-dimethyl-3,5-dioxo-2,3,4,5-tetrahydro-[1,2,4]triazin-6-yl)-phenethyl-amino]-ethyl}-phenoxy)-2-methyl-propionate (114)

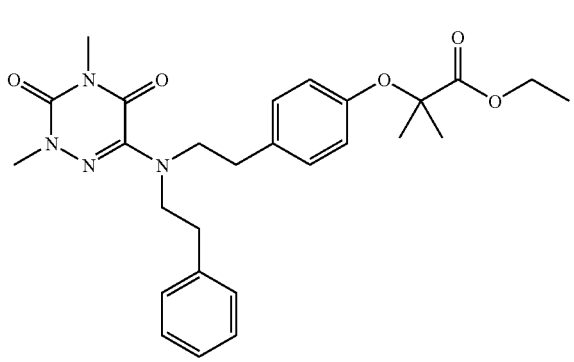

Compound 114 (oil) is prepared from triazine 1b and from intermediate 14b according to synthesis method 1.

TLC silica gel 60 F 254 Merck, $CH_2Cl_2$:AcOEt 90:10, Rf=0.74.

Example 115

Ethyl 2-(4-{2-[(2,4-dimethyl-3,5-dioxo-2,3,4,5-tetrahydro-[1,2,4]triazin-6-yl)-(3-phenylpropyl)-amino]-ethyl}-phenoxy)-2-methyl-propionate (115)

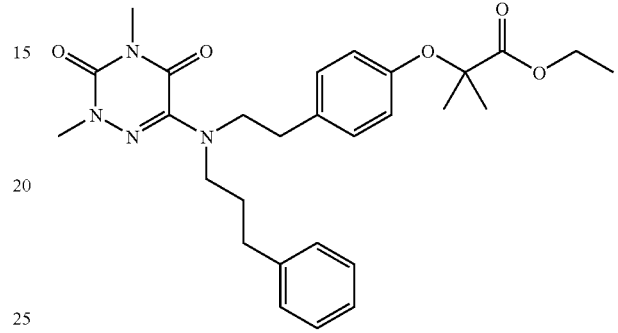

Compound 115 (oil) is prepared from triazine 1b and from intermediate 14c according to synthesis method 1.

TLC silica gel 60 F 254 Merck, $CH_2Cl_2$:AcOEt 90:10, Rf=0.63.

Example 116

Ethyl 2-(4-{2-[(4-heptyl-2-methyl-3,5-dioxo-2,3,4,5-tetrahydro-[1,2,4]triazin-6-yl)-phenethyl-amino]-ethyl}-phenoxy)-2-methyl-propionate (116)

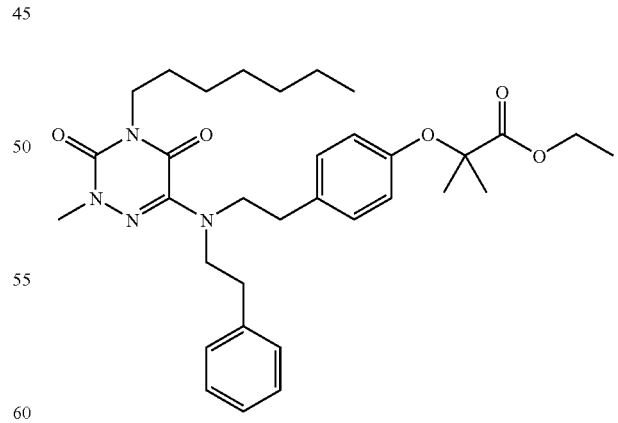

Compound 116 (oil) is prepared from triazine 7a and from intermediate 14b according to synthesis method 1.

TLC silica gel 60 F 254 Merck, $CH_2Cl_2$, Rf=0.52.

Example 117

Ethyl 2-(4-{2-[(4-heptyl-2-methyl-3,5-dioxo-2,3,4,5-tetrahydro-[1,2,4]triazin-6-yl)-(3-phenyl-propyl)-amino]-ethyl}-phenoxy)-2-methyl-propionate (117)

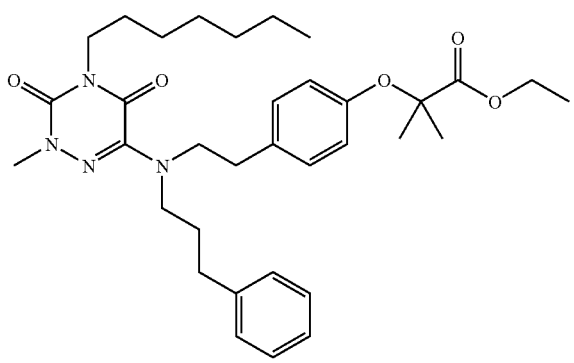

Compound 117 (oil) is prepared from triazine 7a and from intermediate 14c according to synthesis method 1.
TLC silica gel 60 F 254 Merck, CH$_2$Cl$_2$, Rf=0.46.

Example 118

2-Methyl-2-(4-{2-[4-methyl-3,5-dioxo-2-(4,4,4-trifluoro-butyl)-2,3,4,5-tetrahydro-[1,2,4]triazin-6-ylamino]-ethyl}-phenylsulfanyl)-propionic Acid (118)

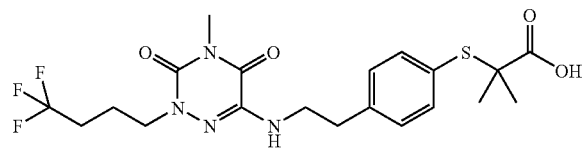

Compound 118 is prepared from triazine 4a and from intermediate 13i according to synthesis method 1. After hydrolysis with trifluoroacetic acid in CH$_2$Cl$_2$, compound 118 is isolated in the form of a solid.
TLC silica gel 60 F 254 Merck, AcOEt, Rf=0.42. F=128° C.

Example 119

Ethyl 2-{4-[2-(2-heptyl-4-methyl-3,5-dioxo-2,3,4,5-tetrahydro-[1,2,4]triazin-6-ylamino)-ethyl]-phenylsulfanyl}-2-methyl-propionate (119)

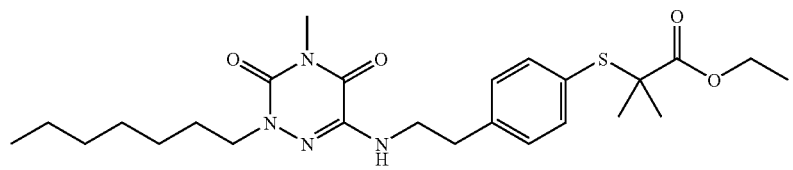

Compound 119 (oil) is prepared from triazine 4b and from intermediate 13g according to synthesis method 1.
TLC silica gel 60 F 254 Merck, petroleum ether:AcOEt 80:20, Rf=0.60.

Example 120

2-{4-[2-(2-Heptyl-4-methyl-3,5-dioxo-2,3,4,5-tetrahydro-[1,2,4]triazin-6-ylamino)-ethyl]-phenylsulfanyl}-2-methyl-propionic Acid (120)

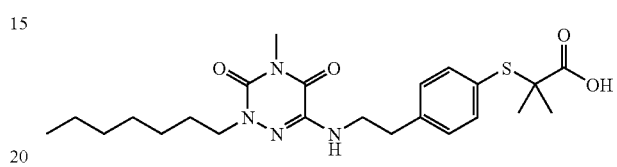

Compound 120 is prepared from triazine 4b and from intermediate 13i according to synthesis method 1. After hydrolysis with trifluoroacetic acid in CH$_2$Cl$_2$, compound 120 is isolated in the form of a solid.
TLC silica gel 60 F 254 Merck, CH$_2$Cl$_2$:MeOH 90:10, Rf=0.34. F=70° C.

Example 121

2-{4-[2-(4-Butyl-2-heptyl-3,5-dioxo-2,3,4,5-tetrahydro-[1,2,4]triazin-6-ylamino)-ethyl]-phenylsulfanyl}-2-methyl-propionic Acid (121)

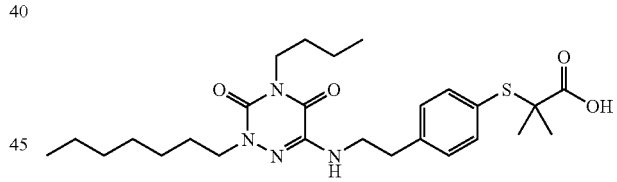

Compound 121 is prepared from triazine 5c and from intermediate 13i according to synthesis method 1. After hydrolysis with trifluoroacetic acid in CH$_2$Cl$_2$, compound 121 is isolated in the form of oil.
TLC silica gel 60 F 254 Merck, CH$_2$Cl$_2$:MeOH 98:2, Rf=0.46.

Example 122

Ethyl 2-{4-[2-(4-heptyl-2-methyl-3,5-dioxo-2,3,4,5-tetrahydro-[1,2,4]triazin-6-ylamino)-ethyl]-phenyl-sulfanyl}-2-methyl-propionate (122)

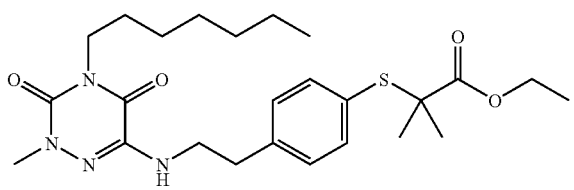

Compound 122 (solid) is prepared from triazine 7a and from intermediate 13g according to synthesis method 1.

TLC silica gel 60 F 254 Merck, petroleum ether:AcOEt 80:20, Rf=0.67. F=49° C.

Example 123

2-(4-{2-[4-Heptyl-3,5-dioxo-2-(4,4,4-trifluoro-butyl)-2,3,4,5-tetrahydro-[1,2,4]triazin-6-ylamino]-ethyl}-phenylsulfanyl)-2-methyl-propionic Acid (123)

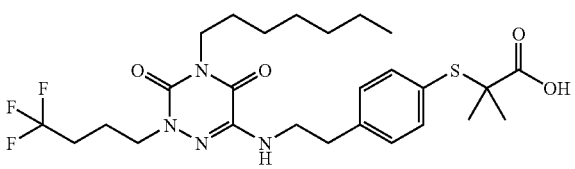

Compound 123 is prepared from triazine 7b and from intermediate 13i according to synthesis method 1. After hydrolysis with trifluoroacetic acid in $CH_2Cl_2$, compound 123 is isolated in the form of a solid.

TLC silica gel 60 F 254 Merck, petroleum ether:AcOEt 80:20, Rf=0.19. F=86° C.

Example 124

Ethyl 2-{4-[3-(2-heptyl-4-methyl-3,5-dioxo-2,3,4,5-tetrahydro-[1,2,4]triazin-6-ylamino)propyl]-phenyl-sulfanyl}-2-methyl-propionate (124)

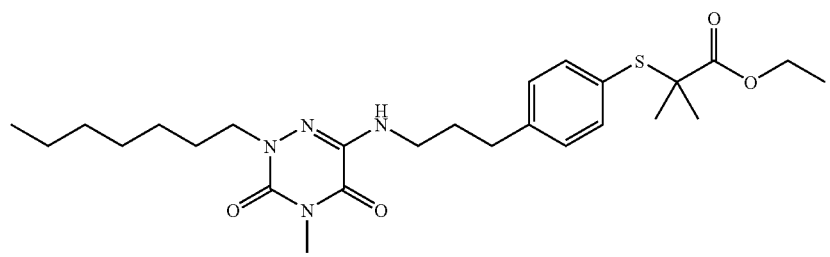

Compound 125 (oil) is prepared from triazine 4b and from intermediate 13h according to synthesis method 1.

TLC silica gel 60 F 254 Merck, petroleum ether:AcOEt 80:20, Rf=0.20.

Pharmacological Evaluation

In Vitro

Activation of transcription (transactivation) of the reporter gene controlled by specific response elements after binding of the ligand to the receptor (reporter gene assay).

These experiments were carried out according to J. M. Lehmann et al. (J. Biol. Chem. 1995, 270:12953-12956) with several modifications. Subconfluent Cos-7 cells (ATCC, CRL-1651) were transfected with (i) chimeric receptors containing the binding domain for human PPARα or PPARγ or PPARδ ligand bound to the DNA binding domain of yeast galactosidase (Gal-4), and (ii) the reporter plasmid containing five copies of the Gal-4 response element upstream of the thymidine kinase promoter adjacent to the luciferase gene (p5xUAS-tk-Luc). After 24 hours, these cells were treated for the following 24 hours by compounds and their vehicle and luciferase activity were evaluated after cellular extraction according to the manufacturer's (Promega) recommendations.

The results are reported in table 17 below, in which the designation "hit" indicates a compound whose transactivation level is significant but for which definition of an $EC_{50}$ is not possible, and in which the designation "nd" indicates that no data was collected.

TABLE 17

| reporter gene transactivation by various human PPAR subtypes | | | |
|---|---|---|---|
| Examples | hPPAR-GAL4 alpha $EC_{50}$ (μM) | hPPAR-GAL4 gamma $EC_{50}$ (μM) | hPPAR-GAL4 delta $EC_{50}$ (μM) |
| Fenofibric acid | 16.9 | 65.2 | >100 |
| Rosiglitazone | 0 | 1.12 | 0 |
| Pioglitazone | >10 | 4.77 | 0 |
| 1 | 3-10 | 0 | 0 |
| 2 | >10 | ~10 | 0 |
| 3 | ~3 | 0 | 0 |
| 4 | >10 | 0 | 0 |
| 5 | ~3 | ~10 | 0 |
| 6 | ~0.3 | 0 | 0 |
| 7 | 0.3-1 | 1-3 | 0 |
| 8 | ~0.3 | 3-10 | 0 |
| 9 | 3-10 | ~10 | 0 |
| 10 | 0.3-1 | ~1 | 0 |
| 11 | 0.3-1 | 1-3 | 0 |
| 12 | ~0.03 | 1-3 | hit |

TABLE 17-continued reporter gene transactivation by various human PPAR subtypes

| Examples | hPPAR-GAL4 alpha $EC_{50}$ (μM) | hPPAR-GAL4 gamma $EC_{50}$ (μM) | hPPAR-GAL4 delta $EC_{50}$ (μM) |
|---|---|---|---|
| 13 | 0.01-0.03 | 0.1-0.3 | ~3 |
| 14 | 0.01-0.03 | ~1 | ~10 |
| 15 | 0.001-0.003 | 0.1-0.3 | hit |
| 16 | ~0.1 | 3-10 | 0 |
| 17 | 0.3-1 | ~0.3 | 0 |
| 18 | 0.03-0.1 | ~1 | 0 |
| 19 | ~3 | 3-10 | 0 |
| 20 | hit | hit | 0 |
| 21 | 3-10 | 0 | 0 |
| 22 | 10 | hit | 0 |
| 23 | 1 | hit | 0 |
| 24 | >10 | 0 | 0 |
| 25 | hit | >10 | hit |
| 26 | >10 | 0 | 0 |
| 27 | ~3 | 3-10 | 3-10 |
| 28 | ~10 | hit | 0 |
| 29 | 3-10 | 3-10 | 3-10 |
| 30 | 0.03-0.1 | >10 | hit |
| 31 | ~0.1 | ~1 | 3-10 |
| 32 | 1-3 | hit | 0 |
| 33 | ~3 | ~3 | 0 |
| 34 | >10 | >10 | 0 |
| 35 | 0.03-0.1 | 3-10 | ~10 |
| 36 | 0.3-1 | 3-10 | hit |
| 37 | >10 | ~10 | 0 |
| 38 | >10 | >10 | 0 |
| 39 | 0.1-0.3 | 3-10 | ~3 |
| 40 | 3-10 | ~10 | >10 |
| 41 | ~0.1 | ~10 | 1-3 |
| 42 | ~1 | >10 | 1-3 |
| 43 | ~3 | hit | 0 |
| 44 | >10 | 3-10 | 0 |
| 45 | 1-3 | ~3 | hit |
| 46 | 0.3-1 | 0 | 0 |
| 47 | ~0.3 | ~0.3 | hit |
| 48 | 0.3-1 | 0.3-1 | ~3 |
| 49 | >10 | >10 | 0 |
| 50 | >10 | ~10 | 0 |
| 51 | 3-10 | >10 | 0 |
| 52 | hit | 0 | 0 |
| 53 | 1-3 | 0 | 0 |
| 54 | >10 | 0 | 0 |
| 55 | >10 | 0 | 0 |
| 56 | hit | hit | 0 |
| 57 | ~3 | 1-3 | hit |
| 58 | >10 | 0 | 0 |
| 59 | 1-3 | nd | 0 |
| 60 | >10 | hit | 0 |
| 61 | ~3 | nd | 0 |
| 62 | >10 | 0 | 0 |
| 63 | 0 | hit | 0 |
| 64 | >10 | 3-10 | hit |
| 65 | 0.1-0.3 | >10 | 0 |
| 66 | 0.03-0.1 | >10 | ~10 |
| 67 | ~1 | nd | 0 |
| 68 | 0.1-0.3 | 3-10 | 0 |
| 69 | 1-3 | ~10 | 0 |
| 70 | ~1 | ~10 | 0 |
| 71 | ~1 | hit | 0 |
| 72 | 3-10 | 3-10 | 0 |
| 73 | 0.1-0.3 | nd | 0 |
| 74 | ~1 | 3-10 | 0 |
| 75 | 3-10 | 3-10 | 0 |
| 76 | 0.01-0.03 | 1-3 | 3-10 |
| 77 | ~0.3 | 3-10 | 0 |
| 78 | >10 | 0 | 0 |
| 79 | ~0.03 | 3-10 | 0 |
| 80 | 0.01-0.03 | 0.3-1 | >10 |
| 81 | 0.3-1 | >10 | 0 |
| 82 | ~0.01 | 0.1-0.3 | hit |
| 83 | >10 | 0 | 0 |
| 84 | 0.003-0.01 | ~0.3 | 1-3 |
| 85 | ~0.03 | 1-3 | hit |
| 86 | >10 | ~1 | hit |
| 87 | ~0.3 | 0.1-0.3 | hit |
| 88 | ~0.3 | ~10 | 0 |
| 89 | >10 | 1-3 | 3-10 |
| 90 | ~0.1 | ~10 | 0 |
| 91 | 0.3-1 | 3-10 | 0 |
| 92 | 0.003-0.01 | 3-10 | 0 |
| 93 | >10 | hit | 0 |
| 94 | 3-10 | 3-10 | 0 |
| 95 | 1-3 | >10 | 0 |
| 96 | 0.03-0.1 | ~10 | >10 |
| 97 | 1-3 | hit | 0 |
| 98 | >10 | 0 | 0 |
| 99 | >10 | 3-10 | 0 |
| 100 | 1-3 | >10 | 0 |
| 101 | 1-3 | 0 | 0 |
| 102 | >10 | hit | 0 |
| 104 | 1-3 | >10 | 0 |
| 105 | 1-3 | ~10 | 0 |
| 106 | ~1 | nd | >10 |
| 107 | ~1 | hit | 0 |
| 108 | >10 | hit | 0 |
| 109 | ~1 | nd | 3-10 |
| 110 | 1-3 | hit | >10 |
| 111 | 0 | hit | 0 |
| 112 | 1-3 | ~10 | 1-3 |
| 113 | 0.3-1 | 3-10 | 0.3-1 |
| 114 | ~10 | nd | 0 |
| 115 | ~3 | nd | >10 |
| 116 | ~10 | nd | 0 |
| 117 | ~10 | nd | 0 |
| 118 | 1-3 | ~10 | 0 |
| 119 | 0.3 | 0.3 | hit |
| 120 | 0.3-1 | 1-3 | hit |
| 121 | 0.03-0.1 | 1-3 | hit |
| 122 | ~0.3 | nd | >10 |
| 123 | 0.1-0.3 | ~10 | 0 |
| 124 | 0.3-1 | >10 | 0 |

In Vivo

Normalization of metabolic parameters (cholesterol, plasma triglycerides) in an insulin-resistant male rat (Ico: ZUCKER-fa/fa), unfed for 16-18 hours, after treatment by oral route, once per day for four days, with the compounds to be evaluated or their administration vehicle.

These metabolic parameters are measured by spectrophotometry at the beginning and the end of each animal's treatment.

TABLE 18

Normalization of metabolic parameters

| Examples | Plasma triglycerides | Plasma cholesterol |
|---|---|---|
| 11 | inactive at 2.5 mg/kg<br>−37% at 10 mg/kg | −25% at 2.5 mg/kg<br>−25% at 10 mg/kg |
| 13 | inactive at 2.5 mg/kg<br>−28% at 10 mg/kg | −8% at 2.5 mg/kg<br>−12% at 10 mg/kg |
| 15 | −22% at 2.5 mg/kg<br>−63% at 10 mg/kg | −4% at 2.5 mg/kg<br>−8% at 10 mg/kg |
| 16 | inactive at 2.5 mg/kg<br>−15% at 10 mg/kg | −14% at 2.5 mg/kg<br>−25% at 10 mg/kg |
| 17 | −37% at 10 mg/kg | active at 10 mg/kg |

TABLE 18-continued

Normalization of metabolic parameters

| Examples | Plasma triglycerides | Plasma cholesterol |
|---|---|---|
| 41 | inactive at 10 mg/kg | −28% at 10 mg/kg |
| 45 | inactive at 10 mg/kg | −16% at 10 mg/kg |
| 46 | −32% at 10 mg/kg | −13% at 10 mg/kg |
| 47 | −45% at 10 mg/kg | −25% at 10 mg/kg |
| 53 | inactive at 10 mg/kg | −7% at 2.5 mg/kg<br>−28% at 10 mg/kg |
| 59 | −13% at 2.5 mg/kg | −37% at 2.5 mg/kg |
| 65 | inactive at 2.5 mg/kg<br>−13% at 10 mg/kg | −13% at 2.5 mg/kg<br>−23% at 10 mg/kg |
| 66 | inactive at 10 mg/kg | −9% at 10 mg/kg |
| 67 | −23% at 10 mg/kg | −14% at 10 mg/kg |
| 68 | active at 10 mg/kg | −21% at 10 mg/kg |
| 72 | inactive at 10 mg/kg | −21% at 10 mg/kg |
| 73 | inactive at 10 mg/kg | −14% at 10 mg/kg |
| 74 | inactive at 2.5 mg/kg<br>−26% at 10 mg/kg | −18% at 2.5 mg/kg<br>−29% at 10 mg/kg |
| 75 | active at 10 mg/kg | −19% at 2.5 mg/kg<br>−13% at 10 mg/kg |
| 76 | −7% at 10 mg/kg | −16% at 2.5 mg/kg<br>−22% at 10 mg/kg |
| 77 | active at 10 mg/kg | −29% at 2.5 mg/kg<br>−35% at 10 mg/kg |
| 79 | −55% at 2.5 mg/kg | −32% at 2.5 mg/kg |
| 80 | inactive at 10 mg/kg | −16% at 10 mg/kg |
| 81 | −17% at 10 mg/kg | −12% at 10 mg/kg |
| 82 | active at 10 mg/kg | −13% at 10 mg/kg |
| 84 | inactive at 2.5 mg/kg<br>−7% at 10 mg/kg | inactive at 2.5 mg/kg<br>−13% at 10 mg/kg |
| 85 | active at 10 mg/kg | −21% at 10 mg/kg |
| 92 | inactive at 10 mg/kg | −18% at 10 mg/kg |
| 95 | inactive at .10 mg/kg | −18% at 2.5 mg/kg<br>−40% at 10 mg/kg |
| 96 | −26% at 2.5 mg/kg<br>−60% at 10 mg/kg | −28% at 2.5 mg/kg<br>−21% at 10 mg/kg |
| 112 | −31% at 10 mg/kg | −43% at 10 mg/kg |
| 113 | inactive at 2.5 mg/kg<br>−26% at 10 mg/kg | −30% at 2.5 mg/kg<br>−40% at 10 mg/kg |
| 119 | active at 2.5 mg/kg<br>−29% at 10 mg/kg | −21% at 2.5 mg/kg<br>−32% at 10 mg/kg |
| 120 | −27% at 2.5 mg/kg<br>−73% at 10 mg/kg | −32% at 2.5 mg/kg<br>−33% at 10 mg/kg |
| 121 | −24% at 2.5 mg/kg | −7% at 2.5 mg/kg |
| 122 | −35% at 10 mg/kg | −22% at 10 mg/kg |
| 123 | −6% at 2.5 mg/kg<br>−20% at 10 mg/kg | −8% at 2.5 mg/kg<br>−14% at 10 mg/kg |

Thus, the present invention relates to the compounds of formula I previously defined as novel medicines of use in the treatment of diseases requiring PPAR alpha and/or PPAR gamma receptor agonists. These compounds are of use in the prevention and the treatment of diseases such as diabetic dyslipidemia, hypertriglyceridemia, hypercholesterolemia, hyperinsulinemia, hyperglycemia, metabolic syndrome, obesity, atherosclerosis, and in dermatology in pathologies with an inflammatory component or resulting from abnormal cell differentiation as well as in the treatment of diseases such as psoriasis, acne, atopic dermatitis, cutaneous aging and photoaging.

Lastly, the invention relates to pharmaceutical compounds containing as an active ingredient at least one compound of formula I previously defined, preferably in association with a suitable excipient.

The invention claimed is:

1. 3,5-Dioxo-(2H,4H)-1,2,4-triazine compounds of formula I

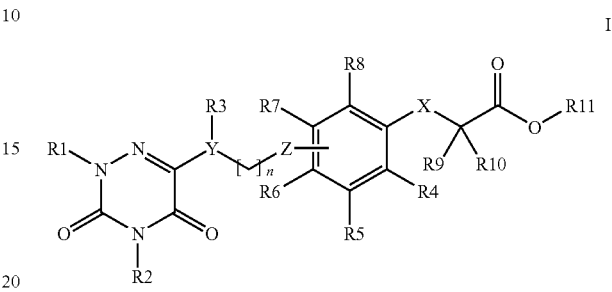

in which $R_1$ and $R_2$ can be identical or different and represent an alkyl or alkenyl radical, linear or branched, at $C_1$-$C_7$, an alkyl radical at $C_1$-$C_6$ substituted by trifluoromethyl, cycloalkyl at $C_5$-$C_6$, nitrile, alkoxycarbonylvinyl at $C_1$-$C_4$, hydroxycarbonylvinyl, alkoxycarbonyl at $C_1$-$C_4$, carboxylate, benzyloxy or phenyl, wherein the core phenyl is optionally substituted by one or more alkyl at $C_1$-$C_4$, alkoxy at $C_1$-$C_4$, nitro, halogen or trifluoromethyl, $YR_3$ represents oxygen or $NR_3$ in which $R_3$ represents hydrogen, an alkyl or alkenyl radical, linear or branched at $C_1$-$C_7$, an alkyl radical at $C_1$-$C_6$ substituted by trifluoromethyl or phenyl, wherein the core phenyl is optionally substituted by one or more alkyl at $C_1$-$C_4$, alkoxy at $C_1$-$C_4$, nitro, halogen or trifluoromethyl, Z represents an oxygen atom or a methylene group which can be bound in ortho, meta or para position on the phenyl group of formula I n can range from 0 to 5 when Z=C or from 2 to 4 when Z=O, X represents oxygen or sulfur, $R_4$, $R_5$, $R_6$, $R_7$ and $R_8$ represent hydrogen or fluorine, $R_9$, $R_{10}$ and $R_{11}$ represent hydrogen or an alkyl group, linear or branched, at $C_1$-$C_5$, or additive salt with pharmaceutically acceptable base thereof.

2. 3,5-Dioxo-(2H,4H)-1,2,4-triazine compounds of formula I according to claim 1 in which:

$R_1$ and $R_2$ represent, independently one from the other, an alkyl or alkenyl radical, linear or branched, at $C_1$-$C_7$, an alkyl radical at $C_1$-$C_6$ substituted by trifluoromethyl, cycloalkyl at $C_6$, nitrile, or phenyl, wherein the core phenyl is optionally substituted by one or more alkyl at $C_1$-$C_4$, alkoxy at $C_1$-$C_4$, nitro, halogen or trifluoromethyl, $YR_3$ represents oxygen or $NR_3$ in which $R_3$ represents hydrogen, an alkyl or alkenyl radical, linear or branched, at $C_1$-$C_7$, an alkyl radical at $C_1$-$C_6$ substituted by trifluoromethyl or phenyl, Z represents an oxygen atom or a methylene group which can be bound in ortho, meta or para position on the phenyl group of formula I n can range from 0 to 5 when Z=C or from 2 to 4 when Z=O, X represents oxygen or sulfur, $R_4$, $R_5$, $R_6$, $R_7$ and $R_8$ represent hydrogen or fluorine, $R_9$, $R_{10}$ and $R_{11}$ represent hydrogen or an alkyl group, linear or branched, at $C_1$-$C_5$, or additive salt with pharmaceutically acceptable base thereof.

3. 3,5-Dioxo-(2H,4H)-1,2,4-triazine compounds of formula I according to one of the claims 1 and 2 in which:

$R_1$ and $R_2$ represent independently one from the other, an alkyl or alkenyl radical, linear or branched, at $C_1$-$C_7$, an alkyl radical at $C_1$-$C_6$ substituted by trifluoromethyl or nitrile, $YR_3$ represents oxygen or $NR_3$ in which $R_3$ represents hydrogen or a linear or branched alkyl radical at $C_1$-$C_7$, Z represents a methylene group which can be bound in ortho, meta or para position on the phenyl group of formula I, n can range from 0 to 5, X represents oxygen or sulfur, $R_4$, $R_5$, $R_6$, $R_7$ and $R_8$ represent hydrogen or fluorine, $R_9$, $R_{10}$ and $R_{11}$ represents hydrogen or a linear or branched alkyl group at $C_1$-$C_5$, or additive salt with pharmaceutically acceptable base thereof.

4. 3,5-Dioxo-(2H,4H)-1,2,4-triazine compounds of formula I according to one of the claims 1 and 3 in which:

$R_1$ and $R_2$ represent independently one from the other, an alkyl or alkenyl radical, linear or branched, at $C_1$-$C_7$, optionally substituted at the end of the chain by a trifluoromethyl group, $YR_3$ represents oxygen or $NR_3$ in which $R_3$ represents hydrogen or a linear or branched alkyl radical at $C_1$-$C_7$, Z represents a methylene group which can be bound in meta or para position on the phenyl group of formula I, n can range from 1 to 5, X represents oxygen or sulfur, $R_4$ to $R_8$ represent hydrogen, $R_9$ and $R_{10}$ represent a methyl radical represents hydrogen or an ethyl radical, or additive salt with pharmaceutically acceptable base thereof.

5. Compounds of formula I according to claim 1 wherein they are selected among:

1. Ethyl 2-{2-[2-(4-butyl-2-methyl-3,5-dioxo-2,3,4,5-tetrahydro-[1,2,4]triazin-6-yloxy)-ethyl]-phenoxy}-2-methyl-propionate
2. Ethyl 2-{3-[2-(2-heptyl-4-methyl-3,5-dioxo-2,3,4,5-tetrahydro-[1,2,4]triazin-6-yloxy)-ethyl]-phenoxy}-2-methyl-propionate
3. Ethyl 2-methyl-2-(3-{2-[2-methyl-3,5-dioxo-4-(4,4,4-trifluoro-butyl)-2,3,4,5-tetrahydro-[1,2,4]triazin-6-yloxy]-ethyl}phenoxy)-propionate
4. Ethyl 2-methyl-2-(3-{3-[4-methyl-3,5-dioxo-2-(4,4,4-trifluoro-butyl)-2,3,4,5-tetrahydro-[1,2,4]triazin-6-yloxy]-ethyl}-phenoxy)-propionate
5. Ethyl 2-{3-[3-(2-heptyl-4-methyl-3,5-dioxo-2,3,4,5-tetrahydro-[1,2,4]triazin-6-yloxy)-propyl]-phenoxy}-2-methyl-propionate
6. Ethyl 2-methyl-2-(3-{3-[2-methyl-3,5-dioxo-4-(4,4,4-trifluoro-butyl)-2,3,4,5-tetrahydro-[1,2,4]triazin-6-yloxy]-ethyl}-phenoxy)-propionate
7. Ethyl 2-{3-[3-(4-heptyl-2-methyl-3,5-dioxo-2,3,4,5-tetrahydro-[1,2,4]triazin-6-yloxy)-propyl]-phenoxy}-2-methyl-propionate
8. Ethyl 2-(3-{3-[4 heptyl-3,5-dioxo-2-(4,4,4-trifluoro-butyl)-2,3,4,5-tetrahydro-[1,2,4]triazin-6-yloxy]-propyl}-phenoxy)-2-methyl-propionate
9. Ethyl 2-methyl-2-(3-{5-[4-methyl-3,5-dioxo-2-(4,4,4-trifluoro-butyl)-2,3,4,5-tetrahydro-[1,2,4]triazin-6-yloxy]-pentyl}-phenoxy)-propionate
10. Ethyl 2-{3-[5-(2-heptyl-4-methyl-3,5-dioxo-2,3,4,5-tetrahydro-[1,2,4]triazin-6-yloxy)-pentyl]-phenoxy}-2-methyl-propionate
11. Ethyl 2-{3-[5-(4-butyl-2-methyl-3,5-dioxo-2,3,4,5-tetrahydro-[1,2,4]triazin-6-yloxy)-pentyl]-phenoxy}-2-methyl-propionate
12. 2-{3-[5-(4-Butyl-2-methyl-3,5-dioxo-2,3,4,5-tetrahydro-[1,2,4]triazin-6-yloxy)-pentyl]-phenoxy}-2-methyl-propionic acid
13. Ethyl 2-{3-[5-(2,4-dibutyl-3,5-dioxo-2,3,4,5-tetrahydro-[1,2,4]triazin-6-yloxy)-pentyl]-phenoxy}-2-methyl-propionate
14. Ethyl 2-(3-{5-[4-butyl-3,5-dioxo-2-(4,4,4-trifluoro-butyl)-2,3,4,5-tetrahydro-[1,2,4]triazin-6-yloxy]-pentyl}-phenoxy)-2-methyl-propionate
15. Ethyl 2-{3-[5-(4-butyl-2-heptyl-3,5-dioxo-2,3,4,5-tetrahydro-[1,2,4]triazin-6-yloxy)-pentyl]-phenoxy}-2-methyl-propionate
16. Ethyl 2-methyl-2-(3-{5-[2-methyl-3,5-dioxo-4-(4,4,4-trifluoro-butyl)-2,3,4,5-tetrahydro-[1,2,4]triazin-6-yloxy]-pentyl}-phenoxy)-propionate
17. Ethyl 2-{3-[5-(4-heptyl-2-methyl-3,5-dioxo-2,3,4,5-tetrahydro-[1,2,4]triazin-6-yloxy)-pentyl]-phenoxy}-2-methyl propionate
18. Ethyl 2-(3-{5-[4-heptyl-3,5-dioxo-2-(4,4,4-trifluoro-butyl)-2,3,4,5-tetrahydro-[1,2,4]triazin-6-yloxy]-pentyl}-phenoxy)-2-methyl-propionate
19. Ethyl 2-{3-[5-(2-benzyl-4-heptyl-3,5-dioxo-2,3,4,5-tetrahydro-[1,2,4]triazin-6-yloxy)-pentyl]-phenoxy}-2-methyl-propionate
20. Ethyl 2-[4-(2-heptyl-4-methyl-3,5-dioxo-2,3,4,5-tetrahydro-[1,2,4]triazin-6-yloxymethyl)-phenoxy]-2-methyl-propionate
21. Ethyl 2-methyl-2-{4-[2-methyl-3,5-dioxo-4-(4,4,4-trifluoro-butyl)-2,3,4,5-tetrahydro-[1,2,4]triazin-6-yloxymethyl]-phenoxy}-propionate
22. Ethyl 2-[4-(4-heptyl-2-methyl-3,5-dioxo-2,3,4,5-tetrahydro-[1,2,4]triazin-6-yloxymethyl)-phenoxy]-2-methyl-propionate
23. Ethyl 2-{4-[4-heptyl-3,5-dioxo-2-(4,4,4-trifluoro-butyl)-2,3,4,5-tetrahydro-[1,2,4]triazin-6-yloxymethyl]-phenoxy}-2-methyl-propionate
24. Ethyl 2-methyl-2-(4-{2-[4-methyl-3,5-dioxo-2-(4,4,4-trifluorobutyl)-2,3,4,5-tetrahydro-[1,2,4]triazin-6-yloxy]-ethyl}-phenoxy)-propionate
25. Ethyl 2-{4-[2-(2-heptyl-4-methyl-3,5-dioxo-2,3,4,5-tetrahydro-[1,2,4]triazin-6-yloxy)-ethyl]-phenoxy}-2-methyl-propionate
26. Ethyl 2-{4-[2-(4-heptyl-2-methyl-3,5-dioxo-2,3,4,5-tetrahydro-[1,2,4]triazin-6-yloxy)-ethyl]-phenoxy}-2-methyl-propionate
27. Ethyl 2-{4-[3-(2-heptyl-4-methyl-3,5-dioxo-2,3,4,5-tetrahydro-[1,2,4]triazin-6-yloxy)-propyl]-phenoxy}-2-methyl-propionate
28. Ethyl 2-methyl-2-(4-{4-[4-methyl-3,5-dioxo-2-(4,4,4-trifluoro-butyl)-2,3,4,5-tetrahydro-[1,2,4]triazin-6-yloxy]-ethyl}-phenoxy)-propionate
29. Ethyl 2-{4-[4-(2-heptyl-4-methyl-3,5-dioxo-2,3,4,5-tetrahydro-[1,2,4]triazin-6-yloxy)-ethyl]-phenoxy}-2-methyl-propionate
30. Ethyl 2-methyl-2-(4-{4-[2-methyl-3,5-dioxo-4-(4,4,4-trifluoro-butyl)-2,3,4,5-tetrahydro-[1,2,4]triazin-6-yloxy]-ethyl}-phenoxy)-propionate 31. Ethyl 2-(4-{4-[4-heptyl-3,5-dioxo-2-(4,4,4-trifluoro-butyl)-2,3,4,5-tetrahydro-[1,2,4]triazin-6-yloxy]-butyl}-phenoxy)-2-methyl-propionate
32. Ethyl 2-{3-[3-(2-heptyl-4-methyl-3,5-dioxo-2,3,4,5-tetrahydro-[1,2,4]triazin-6-yloxy)-propyl]-phenylsulfanyl}-2-methyl-propionate
33. Ethyl 2-{3-[3-(2-heptyl-4-methyl-3,5-dioxo-2,3,4,5-tetrahydro-[1,2,4]triazin-6-yloxy)-propoxy]-phenoxy}-2-methyl-propionate
34. Ethyl 2-{3-[3-(2-heptyl-4-methyl-3,5-dioxo-2,3,4,5-tetrahydro-[1,2,4]triazin-6-yloxy)-propoxy]-phenylsulfanyl}-2-methyl-propionate
35. Ethyl 2-(3-{3-[3,5-dioxo-2,4-bis-(4,4,4-trifluoro-butyl)-2,3,4,5-tetrahydro-[1,2,4]triazin-6-yloxy]-propoxy}-phenoxy)-2-methyl-propionate
36. Ethyl 2-{3-[4-(2-heptyl-4-methyl-3,5-dioxo-2,3,4,5-tetrahydro-[1,2,4]triazin-6-yloxy)-butoxy]-phenoxy}-2-methyl-propionate
37. Ethyl 2-{3-[4-(2-heptyl-4-methyl-3,5-dioxo-2,3,4,5-tetrahydro-[1,2,4]triazin-6-yloxy)-butoxy]-phenylsulfanyl}-2-methyl-propionate
38. Ethyl 2-{4-[2-(2-heptyl-4-methyl-3,5-dioxo-2,3,4,5-tetrahydro-[1,2,4]triazin-G-yloxy)-ethoxy]-phenylsulfanyl}-2-methyl-propionate
39. Ethyl 2-(4-{3-[3,5-dioxo-2,4-bis-(4,4,4-trifluoro-butyl)-2,3,4,5-tetrahydro-[1,2,4]triazin-6-yloxy]-propoxy}-phenoxy)-2-methyl-propionate
40. Ethyl 2-{4-[2-(2-heptyl-4-methyl-3,5-dioxo-2,3,4,5-tetrahydro-[1,2,4]triazin-6-ylamino)-ethoxy]-phenoxy}-2-methyl-propionate
41. Ethyl 2-(4-{2-[3,5-dioxo-2,4-bis-(4,4,4-trifluoro-butyl)-2,3,4,5-tetrahydro-[1,2,4]triazin-6-ylamino]-ethoxy}-phenoxy)-2-methyl-propionate
42. Ethyl 2-{4-[2-(2,4-diheptyl-3,5-dioxo-2,3,4,5-tetrahydro-[1,2,4]triazin-6-ylamino)-ethoxy]-phenoxy}-2-methyl-propionate
43. Ethyl 2-(4-{2-[2,4-bis-(3-cyclohexyl-propyl)-3,5-dioxo-2,3,4,5-tetrahydro-[1,2,4]triazin-6-ylamino]-ethoxy}-phenoxy)-2-methyl-propionate
44. Ethyl 2-methyl-2-(4-{3-[4-methyl-3,5-dioxo-2-(4,4,4-trifluoro-butyl)-2,3,4,5-tetrahydro-[1,2,4]triazin-6-ylamino]-propoxy}-phenoxy)-propionate
45. Ethyl 2-{4-[3-(2-heptyl-4-methyl-3,5-dioxo-2,3,4,5-tetrahydro-[1,2,4]triazin-6-ylamino)-propoxy]-phenoxy}-2-methyl-propionate
46. Ethyl 2-methyl-2-(4-{3-[2-methyl-3,5-dioxo-4-(4,4,4-trifluoro-butyl)-2,3,4,5-tetrahydro-[1,2,4]triazin-6-ylamino]-propoxy}-phenoxy)-propionate
47. Ethyl 2-{4-[3-(4-heptyl-2-methyl-3,5-dioxo-2,3,4,5-tetrahydro-[1,2,4]triazin-6-ylamino)-propoxy]-phenoxy}-2-methyl-propionate
48. Ethyl 2-(4-{3-[4-heptyl-3,5-dioxo-2-(4,4,4-trifluoro-butyl)-2,3,4,5-tetrahydro-[1,2,4]triazin-6-ylamino]-propoxy}-phenoxy)-2-methyl-propionate
49. Ethyl 2-{4-[3-(4-heptyl-2-methyl-3,5-dioxo-2,3,4,5-tetrahydro-[1,2,4]triazin-6-ylamino)-propoxy]-phenylsulfanyl}-2-methyl-propionate
50. Ethyl 2-{4-[4-(4-heptyl-2-methyl-3,5-dioxo-2,3,4,5-tetrahydro-[1,2,4]triazin-6-ylamino)-butoxy]-phenoxy}-2-methyl-propionate
51. Ethyl 2-(3-{3-[(2-heptyl-4-methyl-3,5-dioxo-2,3,4,5-tetrahydro-[1,2,4]triazin-6-yl)-(4,4,4-trifluoro-butyl)-amino]-propoxy}-phenoxy)-2-methyl-propionate
52. Ethyl 2-(3-{3-[(2,4-dimethyl-3,5-dioxo-2,3,4,5-tetrahydro-[1,2,4]triazin-6-yl)-heptyl-amino]-propoxy}-phenylsulfanyl)-2-methyl-propionate
53. Ethyl 2-(4-{3-[(2,4-dimethyl-3,5-dioxo-2,3,4,5-tetrahydro-[1,2,4]triazin-6-yl)-heptyl-amino]-propoxy}-phenylsulfanyl)-2-methyl-propionate
54. Ethyl 2-(3-{4-[(2,4-dimethyl-3,5-dioxo-2,3,4,5-tetrahydro-[1,2,4]triazin-6-yl)-heptyl-amino]-butoxy}-phenylsulfanyl)-2-methyl-propionate
55. Ethyl 2-(2-{2-[3,5-dioxo-2,4-bis-(4,4,4-trifluoro-butyl)-2,3,4,5-tetrahydro-[1,2,4]triazin-6-ylamino]-ethyl}-phenoxy)-2-methyl-propionate
56. Ethyl 2-methyl-2-(3-{2-[4-methyl-3,5-dioxo-2-(4,4,4-trifluoro-butyl)-2,3,4,5-tetrahydro-[1,2,4]triazin-6-ylamino]-ethyl}-phenoxy)-propionate
57. Ethyl 2-{3-[2-(2-heptyl-4-methyl-3,5-dioxo-2,3,4,5-tetrahydro-[1,2,4]triazin-6-ylamino)-ethyl]-phenoxy}-2-methyl-propionate
58. Ethyl 2-methyl-2-(3-{2-[2-methyl-3,5-dioxo-4-(4,4,4-trifluoro-butyl)-2,3,4,5-tetrahydro-[1,2,4]triazin-6-ylamino]-ethyl}-phenoxy)-propionate
59. Ethyl 2-{3-[2-(4-heptyl-2-methyl-3,5-dioxo-2,3,4,5-tetrahydro-[1,2,4]triazin-6-ylamino)-ethyl]-phenoxy}-2-methyl-propionate
60. Ethyl 2-(3-{2-[4-heptyl-3,5-dioxo-2-(4,4,4-trifluoro-butyl)-2,3,4,5-tetrahydro-[1,2,4]triazin-6-ylamino]-ethyl}-phenoxy)-2-methyl-propionate
61. Ethyl 2-{3-[2-(4-heptyl-2-methyl-3,5-dioxo-2,3,4,5-tetrahydro-[1,2,4]triazin-6-ylamino)-ethyl]-phenylsulfanyl}-2-methyl-propionate
62. Ethyl 2-methyl-2-(3-{3-[4-methyl-3,5-dioxo-2-(4,4,4-trifluoro-butyl)-2,3,4,5-tetrahydro-[1,2,4]triazin-6-ylamino]-ethyl}-phenoxy)-propionate
63. Ethyl 2-(3-{3-[3-(2-cyano-ethyl)-4-methyl-3,5-dioxo-2,3,4,5-tetrahydro-[1,2,4]triazin-6-ylamino]-propyl}-phenoxy)-2-methyl-propionate
64. Ethyl 2-{3-[3-(2-heptyl-4-methyl-3,5-dioxo-2,3,4,5-tetrahydro-[1,2,4]triazin-6-ylamino)-propyl]-phenoxy}-2-methyl-propionate
65. Ethyl 2-methyl-2-(3-{3-[2-methyl-3,5-dioxo-4-(4,4,4-trifluoro-butyl)-2,3,4,5-tetrahydro-[1,2,4]triazin-6-ylamino]-ethyl}-phenoxy)-propionate
66. Ethyl 2-(3-{3-[3,5-dioxo-2,4-bis-(4,4,4-trifluoro-butyl)-2,3,4,5-tetrahydro-[1,2,4]triazin-6-ylamino]-propyl}-phenoxy)-2-methyl-propionate
67. Ethyl 2-{3-[3-(4-heptyl-2-methyl-3,5-dioxo-2,3,4,5-tetrahydro-[1,2,4]triazin-6-ylamino)-propyl]-phenoxy}-2-methyl-propionate
68. Ethyl 2-(3-{3-[4-heptyl-3,5-dioxo-2-(4,4,4-trifluoro-butyl)-2,3,4,5-tetrahydro-[1,2,4]triazin-6-ylamino]-propyl}-phenoxy)-2-methyl-propionate
69. Ethyl 2-{3-[3-(2,4-diheptyl-3,5-dioxo-2,3,4,5-tetrahydro-[1,2,4]triazin-6-ylamino)-propyl]-phenoxy}-2-methyl-propionate
70. Ethyl 2-{3-[3-(2-benzyl-4-heptyl-3,5-dioxo-2,3,4,5-tetrahydro-[1,2,4]triazin-6-ylamino)-propyl]-phenoxy}-2-methyl-propionate
71. Ethyl 2-(3-{3-[4-benzyl-3,5-dioxo-2-(4,4,4-trifluoro-butyl)-2,3,4,5-tetrahydro-[1,2,4]triazin-6-ylamino]-propyl}-phenoxy)-2-methyl-propionate
72. Ethyl 2-{3-[3-(4-benzyl-2-heptyl-3,5-dioxo-2,3,4,5-tetrahydro-[1,2,4]triazin-6-ylamino)-propyl]-phenoxy}-2-methyl-propionate
73. Ethyl 2-{3-[3-(4-heptyl-2-methyl-3,5-dioxo-2,3,4,5-tetrahydro-[1,2,4]triazin-6-ylamino)-propyl]-phenylsulfanyl}-2-methyl-propionate
74. Ethyl 2-methyl-2-(3-{4-[4-methyl-3,5-dioxo-2-(4,4,4-trifluoro-butyl)-2,3,4,5-tetrahydro-[1,2,4]triazin-6-ylamino]-butyl}-phenoxy)-propionate 75. Ethyl 2-{3-[4-(2-heptyl-4-methyl-3,5-dioxo-2,3,4,5-tetrahydro-[1,2,4]triazin-6-ylamino)-butyl]-phenoxy}-2-methyl-propionate
76. Ethyl 2-methyl-2-(3-{4-[4-(3-methyl-but-2-enyl)-3,5-dioxo-2-(4,4,4-trifluoro-butyl)-2,3,4,5-tetrahydro-[1,2,4]triazin-6-ylamino]-butyl}-phenoxy)-propionate
77. Ethyl 2-methyl-2-(3-{4-[2-methyl-3,5-dioxo-4-(4,4,4-trifluoro-butyl)-2,3,4,5-tetrahydro-[1,2,4]triazin-6-ylamino]-butyl}-phenoxy)-propionate
78. Tert-butyl 2-methyl-2-(3-{4-[2-methyl-3,5-dioxo-4-(4,4,4-trifluoro-butyl)-2,3,4,5-tetrahydro-[1,2,4]triazin-6-ylamino]-butyl}-phenoxy)-propionate
79. 2-Methyl-2-(3-{4-[2-methyl-3,5-dioxo-4-(4,4,4-trifluoro-butyl)-2,3,4,5-tetrahydro-[1,2,4]triazin-6-ylamino]-butyl}-phenoxy)-propionic acid
80. Ethyl 2-(3-{4-[3,5-dioxo-2,4-bis-(4,4,4-trifluoro-butyl)-2,3,4,5-tetrahydro-[1,2,4]triazin-6-ylamino]-butyl}-phenoxy)-2-methyl-propionate
81. Ethyl 2-(3-{4-[2-(2-cyano-ethyl)-3,5-dioxo-4-(4,4,4-trifluoro-butyl)-2,3,4,5-tetrahydro-[1,2,4]triazin-6-ylamino]-butyl}-phenoxy)-2-methyl-propionate
82. Ethyl 2-(3-{4-[2-heptyl-3,5-dioxo-4-(4,4,4-trifluoro-butyl)-2,3,4,5-tetrahydro-[1,2,4]triazin-6-ylamino]-butyl}-phenoxy)-2-methyl-propionate
83. Tert-butyl 2-(3-{4-[2-heptyl-3,5-dioxo-4-(4,4,4-trifluoro-butyl)-2,3,4,5-tetrahydro-[1,2,4]triazin-6-ylamino]-butyl}-phenoxy)-2-methyl-propionate
84. 2-(3-{4-[2-Heptyl-3,5-dioxo-4-(4,4,4-trifluoro-butyl)-2,3,4,5-tetrahydro-[1,2,4]triazin-6-ylamino]-butyl}-phenoxy)-2-methyl-propionic acid
85. Ethyl 2-(3-{4-[4-heptyl-3,5-dioxo-2-(4,4,4-trifluoro-butyl)-2,3,4,5-tetrahydro-[1,2,4]triazin-6-ylamino]-butyl}-phenoxy)-2-methyl-propionate
86. Ethyl 2-(3-{4-[2-(2-cyano-ethyl)-4-heptyl-3,5-dioxo-2,3,4,5-tetrahydro-[1,2,4]triazin-6-ylamino]-butyl}-phenoxy)-2-methyl-propionate
87. Ethyl 4-(6-{4-[3-(1-ethoxycarbonyl-1-methyl-ethoxy)-phenyl-]-butylamino}-4-heptyl-3,5-dioxo-4,5-dihydro-3H-[1,2,4]triazin-2-yl)-but-2-enonate
88. Ethyl 2-{3-[4-(2,4-diheptyl-3,5-dioxo-2,3,4,5-tetrahydro-[1,2,4]triazin-6-ylamino)-butyl]-phenoxy}-2-methyl-propionate
89. Ethyl 2-{3-[4-(2-benzyl-4-heptyl-3,5-dioxo-2,3,4,5-tetrahydro-[1,2,4]triazin-6-ylamino)-butyl]-phenoxy}-2-methyl-propionate
90. Ethyl 2-(3-{4-[4-benzyl-3,5-dioxo-2-(4,4,4-trifluoro-butyl)-2,3,4,5-tetrahydro-[1,2,4]triazin-6-ylamino]-butyl}-phenoxy)-2-methyl-propionate
91. Ethyl 2-{3-[4-(4-benzyl-2-heptyl-3,5-dioxo-2,3,4,5-tetrahydro-[1,2,4]triazin-6-ylamino)-butyl]-phenoxy}-2-methyl-propionate
92. Ethyl 2-(3-{5-[3,5-dioxo-2,4-bis-(4,4,4-trifluoro-butyl)-2,3,4,5-tetrahydro-[1,2,4]triazin-6-ylamino]-pentyl}-phenoxy)-2-methyl-propionate
93. Ethyl 2-methyl-2-(3-{4-[4-methyl-3,5-dioxo-2-(4,4,4-trifluoro-butyl)-2,3,4,5-tetrahydro-[1,2,4]triazin-6-ylamino]-butyl}-phenylsulfanyl)-propionate
94. Ethyl 2-{3-[4-(2-heptyl-4-methyl-3,5-dioxo-2,3,4,5-tetrahydro-[1,2,4]triazin-6-ylamino)-butyl]-phenylsulfanyl}-2-methyl-propionate
95. Ethyl 2-methyl-2-(3-{4-[2-methyl-3,5-dioxo-4-(4,4,4-trifluoro-butyl)-2,3,4,5-tetrahydro-[1,2,4]triazin-6-ylamino]-butyl}-phenylsulfanyl)-propionate
96. 2-Methyl-2-(3-{4-[2-methyl-3,5-dioxo-4-(4,4,4-trifluoro butyl)-2,3,4,5-tetrahydro-[1,2,4]triazin-6-ylamino]-butyl}-phenylsulfanyl)-propionic acid
97. Ethyl 2-(3-{4-[4-heptyl-3,5-dioxo-2-(4,4,4-trifluoro-butyl)-2,3,4,5-tetrahydro-[1,2,4]triazin-6-ylamino]-butyl}-phenylsulfanyl)-2-methyl-propionate
98. Ethyl 2-{3-[4-(2,4-diheptyl-3,5-dioxo-2,3,4,5-tetrahydro-[1,2,4]triazin-6-ylamino)-butyl]-phenylsulfanyl}-2-methyl-propionate
99. Ethyl 2-{3-[4-(2-benzyl-4-heptyl-3,5-dioxo-2,3,4,5-tetrahydro-[1,2,4]triazin-6-ylamino)-butyl]-phenylsulfanyl}-2-methyl-propionate
100. Ethyl 2-(3-{4-[4-benzyl-3,5-dioxo-2-(4,4,4-trifluoro-butyl)-2,3,4,5-tetrahydro-[1,2,4]triazin-6-ylamino]-butyl}-phenylsulfanyl)-2-methyl-propionate
101. Ethyl 2-{3-[4-(4-benzyl-2-heptyl-3,5-dioxo-2,3,4,5-tetrahydro-[1,2,4]triazin-6-ylamino)-butyl]-phenylsulfanyl}-2-methyl-propionate
102. Ethyl 2-methyl-2-(4-{2-[4-methyl-3,5-dioxo-2-(4,4,4-trifluoro-butyl)-2,3,4,5-tetrahydro-[1,2,4]triazin-6-ylamino]-ethyl}-phenoxy)-propionate
103. Ethyl 2-{4-[2-(2-heptyl-4-methyl-3,5-dioxo-2,3,4,5-tetrahydro-[1,2,4]triazin-6-ylamino)-ethyl]-phenoxy}-2-methyl-propionate
104. Ethyl 4-[6-{2-[4-(1-ethoxycarbonyl-1-methyl-ethoxy)-phenyl]-ethylamino}-3,5-dioxo-4-(4,4,4-trifluoro-butyl)-4,5-dihydro-3H-[1,2,4]triazin-2-yl]-but-2-enoate
105. Ethyl 2-(4-{2-[2-(3-cyclohexyl-propyl)-3,5-dioxo-4-(4,4,4-trifluoro-butyl)-2,3,4,5-tetrahydro-[1,2,4]triazin-6-ylamino]-ethyl}-phenoxy)-2-methyl-propionate
106. Ethyl 2-{4-[2-(4-heptyl-2-methyl-3,5-dioxo-2,3,4,5-tetrahydro-[1,2,4]triazin-6-ylamino)-ethyl]-phenoxy}-2-methyl-propionate
107. Ethyl 2-(4-{2-[4-heptyl-3,5-dioxo-2-(4,4,4-trifluoro-butyl)-2,3,4,5-tetrahydro-[1,2,4]triazin-6-ylamino]-ethyl}-phenoxy)-2-methyl-propionate
108. Ethyl 2-{4-[2-(2,4-diheptyl-3,5-dioxo-2,3,4,5-tetrahydro-[1,2,4]triazin-6-ylamino)-ethyl]-phenoxy}-2-methyl-propionate
109. Ethyl 2-{4-[2-(4-benzyl-2-heptyl-3,5-dioxo-2,3,4,5-tetrahydro-[1,2,4]triazin-6-ylamino)-ethyl]-phenoxy}-2-methyl-propionate
110. Ethyl 2-{4-[2-(2,4-bis-benzyloxymethyl-3,5-dioxo-2,3,4,5-tetrahydro-[1,2,4]triazin-6-ylamino)-ethyl]-phenoxy}-2-methyl-propionate
111. Ethyl 2-(4-{2-[(2,4-dimethyl-3,5-dioxo-2,3,4,5-tetrahydro-[1,2,4]triazin-6-yl)-(4,4,4-trifluoro-butyl)-amino]-ethyl}-phenoxy)-2-methyl-propionate
112. Ethyl 2-(4-{2-[(2,4-dimethyl-3,5-dioxo-2,3,4,5-tetrahydro-[1,2,4]triazin-6-yl)-heptyl-amino]-ethyl}-phenoxy)-2-methyl-propionate
113. 2-(4-{2-[(2,4-Dimethyl-3,5-dioxo-2,3,4,5-tetrahydro-[1,2,4]triazin-6-yl)-heptyl-amino]-ethyl}-phenoxy)-2-methyl-propionic acid
114. Ethyl 2-(4-{2-[(2,4-dimethyl-3,5-dioxo-2,3,4,5-tetrahydro-[1,2,4]triazin-6-yl)-phenethyl-amino]-ethyl}-phenoxy)-2-methyl-propionate
115. Ethyl 2-(4-{2-[(2,4-dimethyl-3,5-dioxo-2,3,4,5-tetrahydro-[1,2,4]triazin-6-yl)-(3-phenyl-propyl)-amino]-ethyl}-phenoxy)-2-methyl-propionate
116. Ethyl 2-(4-{2-[(4-heptyl-2-methyl-3,5-dioxo-2,3,4,5-tetrahydro-[1,2,4]triazin-6-yl)-phenethyl-amino]-ethyl}-phenoxy)-2-methyl-propionate
117. Ethyl 2-(4-{2-[(4-heptyl-2-methyl-3,5-dioxo-2,3,4,5-tetrahydro-[1,2,4]triazin-6-yl)-(3-phenyl-propyl)-amino]-ethyl}-phenoxy)-2-methyl-propionate
118. 2-Methyl-2-(4-{2-[4-methyl-3,5-dioxo-2-(4,4,4-trifluoro-butyl)-2,3,4,5-tetrahydro-[1,2,4]triazin-6-ylamino]-ethyl}-phenylsulfanyl)-propionic acid 119. Ethyl 2-{4-[2-(2-heptyl-4-methyl-3,5-dioxo-2,3,4,5-tetrahydro-[1,2,4]triazin-6-ylamino)-ethyl]-phenylsulfanyl}-2-methyl-propionate 120. 2-{4-[2-(2-Heptyl-4-methyl-3,5-dioxo-2,3,4,5-tetrahydro-[1,2,4]triazin-6-ylamino)-ethyl]-phenylsulfanyl}-2-methyl-propionic acid 121. 2-{4-[2-(4-Butyl-2-heptyl-3,5-dioxo-2,3,4,5-tetrahydro-[1,2,4]triazin-6-ylamino)-ethyl]-phenylsulfanyl}-2-methyl-propionic acid 122. Ethyl 2-{4-[2-(4-heptyl-2-methyl-3,5-dioxo-2,3,4,5-tetrahydro-[1,2,4]triazin-6-ylamino)-ethyl]-phenylsulfanyl}-2-methyl-propionate 123. 2-(4-{2-[4-Heptyl-3,5-dioxo-2-(4,4,4-trifluoro-butyl)-2,3,4,5-tetrahydro-[1,2,4]triazin-6-ylamino]-ethyl}-phenylsulfanyl)-2-methyl-propionic acid and 124. Ethyl 2-{4-[3-(2-heptyl-4-methyl-3,5-dioxo-2,3,4,5-tetrahydro-[1,2,4]triazin-6-ylamino)-propyl]-phenylsulfanyl}-2-methyl-propionate, or additive salt with pharmaceutically acceptable base thereof.

6. Method of preparation of 3,5-Dioxo-(2H,4H)-1,2,4-triazine compounds of formula I

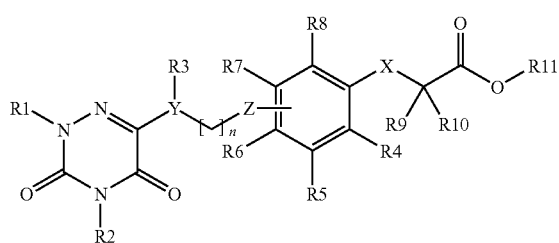

in which

R$_1$ and R$_2$ can be identical or different and represent an alkyl or alkenyl radical, linear or branched, at C$_1$-C$_7$, an alkyl radical at C$_1$-C$_6$ substituted by trifluoromethyl, cycloalkyl at C$_5$-C$_6$, nitrile, alkoxycarbonylvinyl at C$_1$-C$_4$, hydroxycarbonylvinyl, alkoxycarbonyl at C$_1$-C$_4$, carboxylate, benzyloxy or phenyl, wherein the core phenyl is optionally substituted by one or more alkyl at C$_1$-C$_4$, alkoxy at C$_1$-C$_4$, nitro, halogen or trifluoromethyl, YR$_3$ represents oxygen or NR$_3$ in which R$_3$ represents hydrogen, an alkyl or alkenyl radical, linear or branched at C$_1$-C$_7$, an alkyl radical at C$_1$-C$_6$ substituted by trifluoromethyl or phenyl, wherein the core phenyl is optionally substituted by one or more alkyl at C$_1$-C$_4$, alkoxy at C$_1$-C$_4$, nitro, halogen or trifluoromethyl, Z represents an oxygen atom or a methylene group which can be bound in ortho, meta or para position on the phenyl group of formula I n can range from 0 to 5 when Z=C or from 2 to 4 when Z=O, X represents oxygen or sulfur, R$_4$, R$_5$, R$_6$, R$_7$ and R$_8$ represent hydrogen or fluorine, R$_9$, R$_{10}$ and R$_{11}$ represent hydrogen or an alkyl group, linear or branched, at C$_1$-C$_5$, wherein:
a compound of formula II is condensed

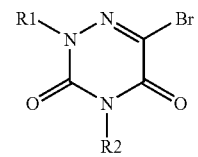

in which R$_1$ and R$_2$ represent the groups defined above in formula I with a compounds of formula III

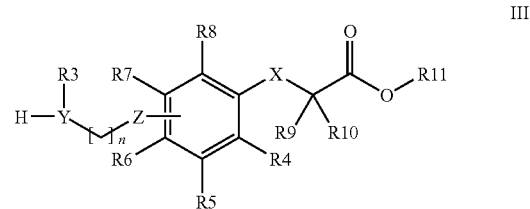

where YR$_3$, n, Z, X, R$_4$, R$_5$, R$_6$, R$_7$, R$_8$, R$_9$, R$_{10}$ and R$_{11}$ are defined above in formula I, in the presence of a base.

7. Method of preparation of 3,5-Dioxo-(2H,4H)-1,2,4-triazine compounds of formula I

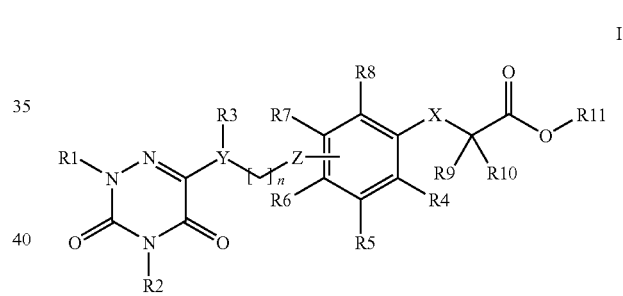

in which

R$_1$ and R$_2$ can be identical or different and represent an alkyl or alkenyl radical, linear or branched, at C$_1$-C$_7$, an alkyl radical at C$_1$-C$_6$ substituted by trifluoromethyl, cycloalkyl at C$_5$-C$_6$, nitrile, alkoxycarbonylvinyl at C$_1$-C$_4$, hydroxycarbonylvinyl, alkoxycarbonyl at C$_1$-C$_4$, carboxylate, benzyloxy or phenyl, wherein the core phenyl is optionally substituted by one or more alkyl at C$_1$-C$_4$, alkoxy at C$_1$-C$_4$, nitro, halogen or trifluoromethyl, YR$_3$ represents oxygen or NR$_3$ in which R$_3$ represents hydrogen, an alkyl or alkenyl radical, linear or branched at C$_1$-C$_7$, an alkyl radical at C$_1$-C$_6$ substituted by trifluoromethyl or phenyl, wherein the core phenyl is optionally substituted by one or more alkyl at C$_1$-C$_4$, alkoxy at C$_1$-C$_4$, nitro, halogen or trifluoromethyl, Z represents an oxygen atom which can be bound in ortho, meta or para position on the phenyl group of formula I n can range from 2 to 4, X represents oxygen or sulfur, R$_4$, R$_5$, R$_6$, R$_7$ and R$_8$ represent hydrogen or fluorine, R$_9$, R$_{10}$ and R$_{11}$ represent hydrogen or an alkyl group, linear or branched, at C$_1$-C$_5$, wherein:
a) a compound of formula II is condensed

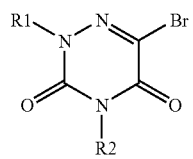

II in which $R_1$ and $R_2$ represent the groups defined above in formula I with a compound of formula IV

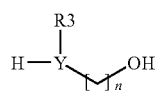

IV in which $R_3Y$ can be equal to NH or O and n is defined in formula I, in the absence of solvent without adding base if $R_3Y=NH$, or in the presence of a base if $R_3Y=O$;
b) the compound obtained V is condensed

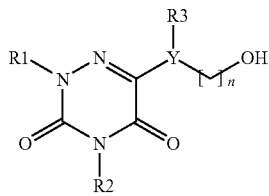

V with a compound of formula VI

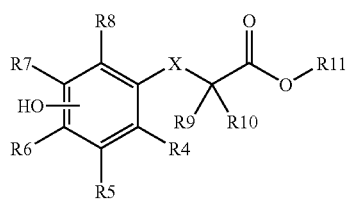

VI where X, $R_4$, $R_5$, $R_6$, $R_7$, $R_8$, $R_9$, $R_{10}$ and $R_{11}$ are defined above in formula I.

8. Method of preparation of 3,5-Dioxo-(2H,4H)-1,2,4-triazine compounds of formula I

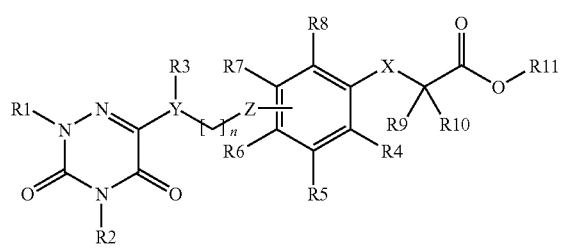

I in which
$R_1$ and $R_2$ can be identical or different and represent an alkyl or alkenyl radical, linear or branched, at $C_1$-$C_7$, an alkyl radical at $C_1$-$C_6$ substituted by trifluoromethyl, cycloalkyl at $C_5$-$C_6$, nitrile, alkoxycarbonylvinyl at $C_1$-$C_4$, hydroxycarbonylvinyl, alkoxycarbonyl at $C_1$-$C_4$, carboxylate, benzyloxy or phenyl, wherein the core phenyl is optionally substituted by one or more alkyl at $C_1$-$C_4$, alkoxy at $C_1$-$C_4$, nitro, halogen or trifluoromethyl, $YR_3$ represents oxygen or $NR_3$ in which $R_3$ represents hydrogen, an alkyl or alkenyl radical, linear or branched at $C_1$-$C_7$, an alkyl radical at $C_1$-$C_6$ substituted by trifluoromethyl or phenyl, wherein the core phenyl is optionally substituted by one or more alkyl at $C_1$-$C_4$, alkoxy at $C_1$-$C_4$, nitro, halogen or trifluoromethyl, Z represents an oxygen atom which can be bound in ortho, meta or para position on the phenyl group of formula I
n can range from 2 to 4,
X represents oxygen or sulfur,
$R_4$, $R_5$, $R_6$, $R_7$ and $R_8$ represent hydrogen or fluorine,
$R_9$, $R_{10}$ and $R_{11}$ represent hydrogen or an alkyl group, linear or branched, at $C_1$-$C_5$,
wherein:
a) the alcohol function of a compound of formula VII is protected

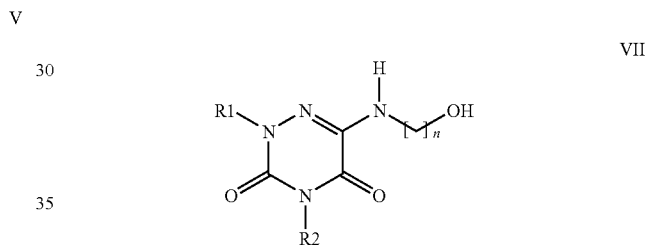

VII in which $R_1$, $R_2$ and n are such as described previously in formula I by a protection group

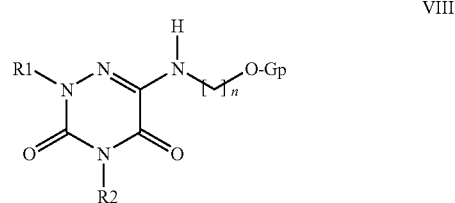

VIII b) the nitrogen of compound VIII previously obtained is alkylated by a halogenated compound $R_3Hal$ in which the Hal group represents a halogen and $R_3$ is as described previously in formula I;

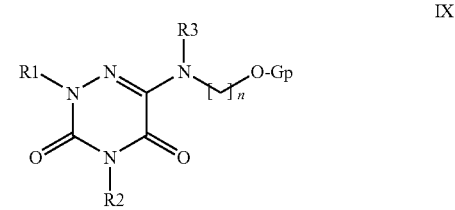

IX c) the compound IX thus obtained is deprotected
d) the compound obtained X is condensed

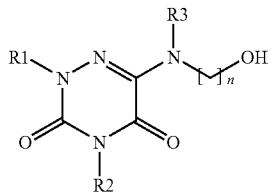

with a compound of formula VI

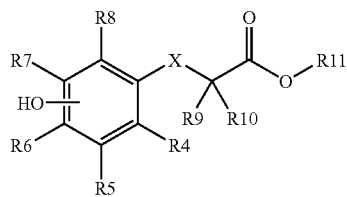

where X, $R_4$, $R_5$, $R_6$, $R_7$, $R_8$, $R_9$, $R_{10}$ and $R_{11}$ are as described previously in formula I.

9. Method of preparation of 3,5-Dioxo-(2H,4H)-1,2,4-triazine compounds of formula I

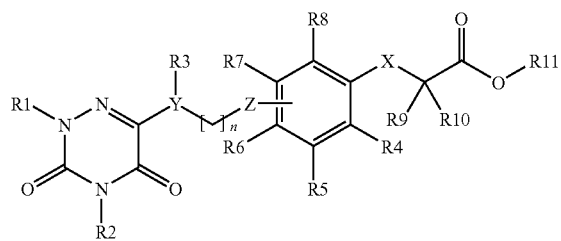

in which
  $R_1$ and $R_2$ can be identical or different and represent an alkyl or alkenyl radical, linear or branched, at $C_1$-$C_7$, an alkyl radical at $C_1$-$C_6$ substituted by trifluoromethyl, cycloalkyl at $C_5$-$C_6$, nitrile, alkoxycarbonylvinyl at $C_1$-$C_4$, hydroxycarbonylvinyl, alkoxycarbonyl at $C_1$-$C_4$, carboxylate, benzyloxy or phenyl, wherein the core phenyl is optionally substituted by one or more alkyl at $C_1$-$C_4$, alkoxy at $C_1$-$C_4$, nitro, halogen or trifluoromethyl,
  $YR_3$ represents $NR_3$ in which $R_3$ represents hydrogen, an alkyl or alkenyl radical, linear or branched at $C_1$-$C_7$, an alkyl radical at $C_1$-$C_6$ substituted by trifluoromethyl or phenyl, wherein the core phenyl is optionally substituted by one or more alkyl at $C_1$-$C_4$, alkoxy at $C_1$-$C_4$, nitro, halogen or trifluoromethyl,
  Z represents a methylene group which can be bound in ortho, meta or para position on the phenyl group of formula I
  n can range from 0 to 5
  X represents oxygen or sulfur,
  $R_4$, $R_5$, $R_6$, $R_7$ and $R_8$ represent hydrogen or fluorine,
  $R_9$, $R_{10}$ and $R_{11}$ represent hydrogen or an alkyl group, linear or branched, at $C_1$-$C_5$,
  wherein:
    a) a compound of formula II is condensed

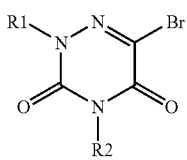

in which $R_1$ and $R_2$ represent the groups as previously described in formula I with a compound of formula XI

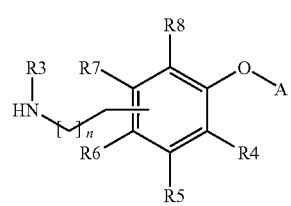

in which n, $R_3$ $R_4$, $R_5$, $R_6$, $R_7$ and $R_8$ are defined above in formula I and A can be hydrogen or a methyl group, in the presence of a base;
    b) after demethylation, the phenol function of compound XII is alkylated

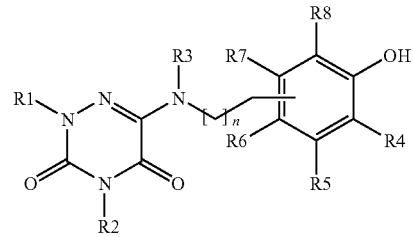

by a halogenated compound of formula XIII in the presence of a base

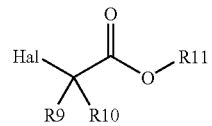

in which the Hal group represents a halogen, and $R_9$, $R_{10}$ and $R_{11}$ are defined above in formula I.

10. Method of preparation of 3,5-Dioxo-(2H,4H)-1,2,4-triazine compounds of formula I

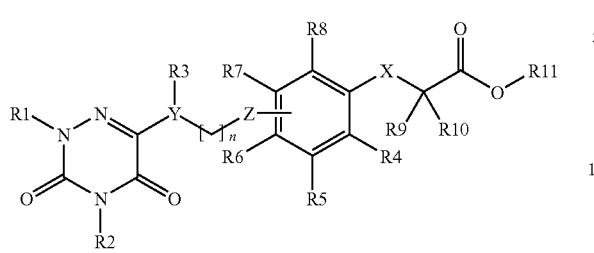

in which
- $R_1$ and $R_2$ can be identical or different and represent an alkyl or alkenyl radical, linear or branched, at $C_1$-$C_7$, an alkyl radical at $C_1$-$C_6$ substituted by trifluoromethyl, cycloalkyl at $C_5$-$C_6$, nitrile, alkoxycarbonylvinyl at $C_1$-$C_4$, hydroxycarbonylvinyl, alkoxycarbonyl at $C_1$-$C_4$, carboxylate, benzyloxy or phenyl, wherein the core phenyl is optionally substituted by one or more alkyl at $C_1$-$C_4$, alkoxy at $C_1$-$C_4$, nitro, halogen or trifluoromethyl,
- $YR_3$ represents $NR_3$ in which $R_3$ represents hydrogen, an alkyl or alkenyl radical, linear or branched at $C_1$-$C_7$, an alkyl radical at $C_1$-$C_6$ substituted by trifluoromethyl or phenyl, wherein the core phenyl is optionally substituted by one or more alkyl at $C_1$-$C_4$, alkoxy at $C_1$-$C_4$, nitro, halogen or trifluoromethyl,
- Z represents a methylene group which can be bound in ortho, meta or para position on the phenyl group of formula I
- n can range from 0 to 5,
- X represents oxygen or sulfur,
- $R_4$, $R_5$, $R_6$, $R_7$ and $R_8$ represent hydrogen or fluorine,
- $R_9$, $R_{10}$ and $R_{11}$ represent hydrogen or an alkyl group, linear or branched, at $C_1$-$C_5$,
  wherein:
    a) a compound of formula XIV is alkylated

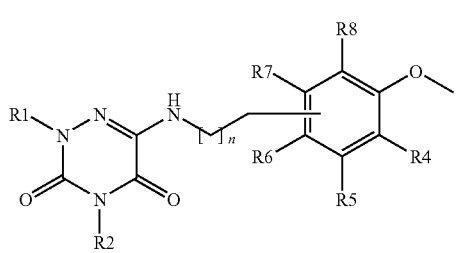

in which $R_1$, $R_2$, $R_4$, $R_5$, $R_6$, $R_7$, $R_8$ et n are defined above in formula I with a compound of formula $R_3$Hal in which the Hal group represents a halogen and $R_3$ is defined above in formula I;

b) after demethylation, the phenol function of the compound XII thus obtained is alkylated

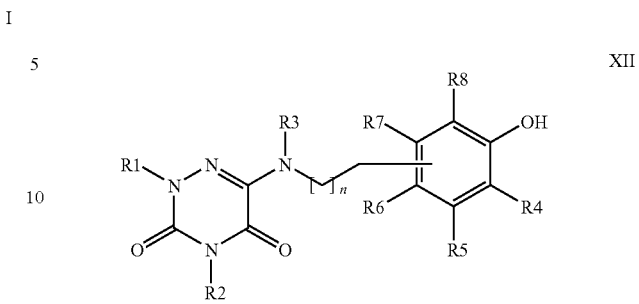

by a halogenated compound of formula XIII in the presence of a base

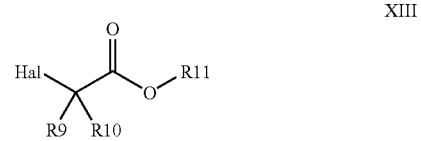

in which the Hal group represents a halogen, and $R_9$, $R_{10}$ and $R_{11}$ are defined above in formula I.

11. Method of preparation of 3,5-Dioxo-(2H,4H)-1,2,4-triazine compounds of formula I

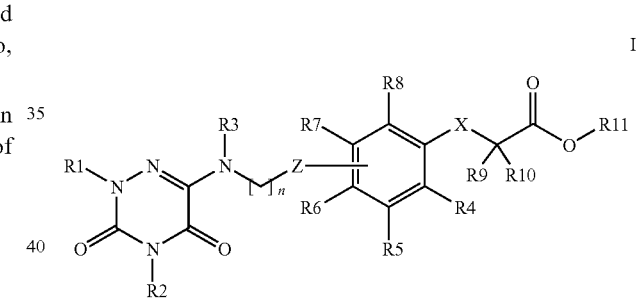

in which
- $R_1$ and $R_2$ can be identical or different and represent an alkyl or alkenyl radical, linear or branched, at $C_1$-$C_7$, an alkyl radical at $C_1$-$C_6$ substituted by trifluoromethyl, cycloalkyl at $C_5$-$C_6$, nitrile, alkoxycarbonylvinyl at $C_1$-$C_4$, hydroxycarbonylvinyl, alkoxycarbonyl at $C_1$-$C_4$, carboxylate, benzyloxy or phenyl, wherein the core phenyl is optionally substituted by one or more alkyl at $C_1$-$C_4$, alkoxy at $C_1$-$C_4$, nitro, halogen or trifluoromethyl,
- $YR_3$ represents oxygen or $NR_3$ in which $R_3$ represents hydrogen, an alkyl or alkenyl radical, linear or branched at $C_1$-$C_7$, an alkyl radical at $C_1$-$C_6$ substituted by trifluoromethyl or phenyl, wherein the core phenyl is optionally substituted by one or more alkyl at $C_1$-$C_4$, alkoxy at $C_1$-$C_4$, nitro, halogen or trifluoromethyl,
- Z represents an oxygen atom or a methylene group which can be bound in ortho, meta or para position on the phenyl group of formula I
- n can range from 0 to 5 when Z=C or from 2 to 4 when Z=O,
- X represents oxygen or sulfur,
- $R_4$, $R_5$, $R_6$, $R_7$ and $R_8$ represent hydrogen or fluorine,
- $R_9$, $R_{10}$ and $R_{11}$ represent hydrogen or an alkyl group, linear or branched, at $C_1$-$C_5$, wherein:
a) a compound of formula I is placed

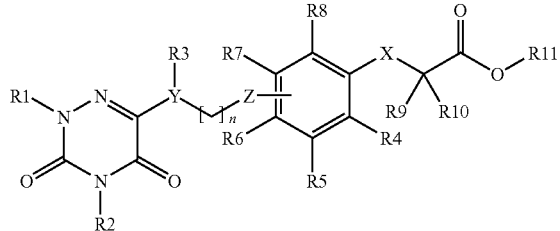

I in which $R_1=(CH_2)_2CN$ and $R_2, R_3, n, Z, X, R_4, R_5, R_6, R_7, R_8, R_9, R_{10}$ and $R_{11}$ are defined above in formula I or $R_2=(CH_2)_2CN$ and $R_1, R_3, n, Z, X, R_4, R_5, R_6, R_7, R_8, R_9, R_{10}$ and $R_{11}$ are defined above in formula I under operating conditions in the presence of a base;
b) the nitrogen of the triazine of compound XIVa or XIVb thus obtained is then alkylated

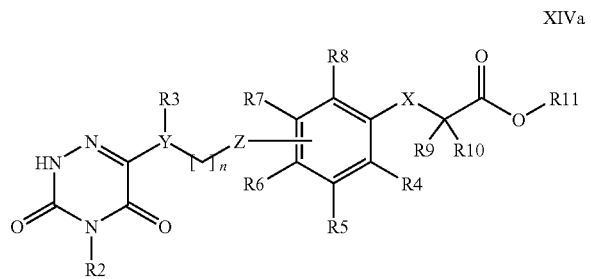

XIVa

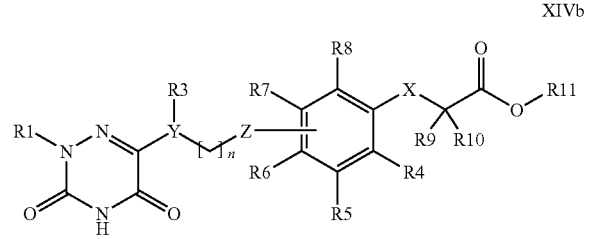

XIVb by a halogenated compound of formula $R_1Hal$ in the case of the intermediate XIVa and of formula $R_2Hal$ in the case of the intermediate XIVb in which the Hal group represents a halogen and $R_1$ and $R_2$ are as defined above in formula I.

12. A method for treating diseases selected from the group consisting of diabetic dyslipidemia, hypertriglyceridemia, hypercholesterolemia, hyperinsulinemia, hyperglycemia, obesity and atherosclerosis, which comprises administering to a person in need thereof a therapeutically effective amount of a compound defined according to claim 1.

13. Pharmaceutical composition comprising as an active ingredient a compound defined according to one of the claims 1 to 5 in association with a suitable excipient.

14. A method for treating obesity, which comprises administering to a person in need thereof a therapeutically effective amount of a compound according to claim 1.

15. The method according to claim 6, wherein the condensation of compounds of formulas II and III is conducted in the presence of triethylamine in n-butanol if $YR_3$ is $NR_3$ or in the presence of potassium carbonate in dimethylformamide if $YR_3$ is oxygen.

16. The method according to claim 7, wherein the condensation of compounds of formulas V and VI is conducted under conditions of the Mitsunobu reaction in the presence of triphenylphosphine and diethylazodicarboxylate in THF.

17. The method according to claim 8, wherein the protection group for step (a) is tertbutyldimethylsilane and the protection group is added in the presence of THF using chlorotertbutyldimethylsilane and imidazole; wherein the halogen in step (b) is Cl, Br or I and alkylation is conducted in the presence of NaH or tBuOK in DMF; wherein deprotection step (c) is conducted using tetrabutylammonium fluoride in THF; and wherein the conditions of the condensation step (d) are those of the Mitsunobu reaction in the presence of triphenylphosphine and diethylazodicarboxylate in THF.

18. The method according to claim 9, wherein condensation step (a) is conducted in the presence of triethylamine in n-butanol; wherein the alkylation in step (b) is conducted in the presence of potassium carbonate; and wherein Hal I step (b) is Cl, Br or I.

19. The method according to claim 10, wherein the alkylation step (a) is conducted in the presence of NaH or tBuOK in DMF; wherein Hal in step (a) is Cl, Br or I; and wherein the alkylation in step (b) is conducted in the presence of potassium carbonate.

20. The method according to claim 11, wherein step (a) is conducted in the presence of NaH in DMF; wherein Hal in step (b) is Cl, Br or I; and wherein the alkylation in step (b) is conducted in the presence of NaH or tBuOK in DMF.

* * * * *